(12) United States Patent
Banks et al.

(10) Patent No.: US 8,466,118 B2
(45) Date of Patent: Jun. 18, 2013

(54) MODULATION OF BLOOD BRAIN BARRIER PROTEIN EXPRESSION

(75) Inventors: William A. Banks, Saint Louis, MO (US); Vijaya B. Kumar, Saint Louis, MO (US); Thomas Darling, Saint Louis, MO (US); Robert Clayton, Foristell, MO (US)

(73) Assignee: Saint Louis University, St. Louis, MO (US)

( * ) Notice: Subject to any disclaimer, the term of this patent is extended or adjusted under 35 U.S.C. 154(b) by 235 days.

(21) Appl. No.: 12/597,458

(22) PCT Filed: Apr. 23, 2008

(86) PCT No.: PCT/US2008/061316
§ 371 (c)(1),
(2), (4) Date: Apr. 22, 2010

(87) PCT Pub. No.: WO2008/131431
PCT Pub. Date: Oct. 30, 2008

(65) Prior Publication Data
US 2010/0196393 A1 Aug. 5, 2010

Related U.S. Application Data

(60) Provisional application No. 60/925,820, filed on Apr. 23, 2007.

(51) Int. Cl.
*A01N 43/04* (2006.01)
*C12Q 1/68* (2006.01)
*C12N 15/63* (2006.01)
*C07H 21/02* (2006.01)
*C07H 21/04* (2006.01)

(52) U.S. Cl.
USPC ............. 514/44; 435/6; 435/91.1; 435/91.31; 435/455; 514/1; 514/2; 536/23.1; 536/24.3; 536/24.5

(58) Field of Classification Search
USPC ............. 435/6, 91.1, 375, 455, 91.31; 514/1, 514/2, 44; 536/23.1, 24.5, 24.3
See application file for complete search history.

(56) References Cited

U.S. PATENT DOCUMENTS

| | | | |
|---|---|---|---|
| 5,220,013 A | 6/1993 | Ponte et al. | 536/23.5 |
| 5,455,169 A | 10/1995 | Mullan | 435/325 |
| 5,837,449 A | 11/1998 | Monia et al. | 435/6.16 |
| 5,853,985 A | 12/1998 | Salbaum et al. | 435/6.16 |
| 5,877,015 A | 3/1999 | Hardy et al. | 435/325 |
| 6,310,048 B1 | 10/2001 | Kumar | 514/44 A |
| 2004/0224907 A1 | 11/2004 | Pasternak et al. | 514/34 |
| 2005/0153914 A1 | 7/2005 | McSwiggen et al. | 514/44 A |
| 2009/0304676 A1 | 12/2009 | Kumar et al. | 424/130.1 |
| 2010/0010065 A1* | 1/2010 | Smith | 514/44 A |
| 2010/0028292 A1 | 2/2010 | Kabanov et al. | 424/78.37 |
| 2011/0166197 A1 | 7/2011 | Darling et al. | 514/44 A |

FOREIGN PATENT DOCUMENTS

| | | |
|---|---|---|
| WO | WO 88/03951 | 6/1988 |
| WO | WO 01/42266 | 6/2001 |
| WO | WO 2007/059435 | 5/2007 |
| WO | WO 2009/105572 | 8/2009 |

OTHER PUBLICATIONS

Crooke, S., Ann. Rev. Medicine, vol. 55, pp. 61-95 (2004).*
Peracchi et al., Rev. Med. Virol., vol. 14, pp. 47-64 (2004).*
Agrawal et al., Molecular Med. Today, vol. 6, pp. 72-81 (2000).*
Su et al., Expert Opin. Drug Deliv., vol. 3, No. 3, pp. 419-435 (2006).*
Chirila et al., Biomaterials, vol. 23, pp. 321-342 (2002).*
Opalinska et al., Nature Rev., vol. 1, pp. 503-514 (2002).*
Holen et al., Nucleic Acids Res., vol. 30, No. 8, pp. 1757-1766 (2002).*
Banks et al., "Delivery across the Blood-Brain Barrier of Antisense Directed against Amyloid β: Reversal of Learning and Memory Deficits in Mice Overexpressing Amyloid Precursor Protein," *J. Pharm Exper. Therap.*, 297(3): 1113-1121, 2001.
Boules et al., "Down-regulation of amyloid precursor protein by peptide nucleic acid in vivo," *J. Mol. Neurosci.*, 24: 123-128, 2004.
Chauhan et al., "Antisense inhibition at the beta-secretase-site of beta-amyloid precursor protein reduces cerebral amyloid and acetyl cholinesterase activity in Tg2576," *Neuroscience*, 146:143-145, 2007.
Coulson et al., "Down-regulation of the amyloid protein precursor of Alzheimer's disease by antisense oligonucleotides reduces neuronal adhesion to specific substrata," *Brain Res.*, 770:72-80, 1997.
Dovey et al., "Functional gamma-secretase inhibitors reduce beta-amyloid peptide levels in brain," *J Neurochem.*, 76:173-181, 2001.
Fukuyama et al., "Nerve growth factor-induced neuronal differentiation is accompanied by differential induction and localization of the amyloid precursor protein (APP) in PC12 cells and variant PC12S cells," *Brain Res. Mol Brai Res.*, 17:17-22, 1993.
Hoffman et al., "A possible role for the Alzheimer amyloid precursor protein in the regulation of epidermal basal cell proliferation," *Eur. J. Cell Biol.*, 79(12):905-914, 2000.
International Search Report issued in PCT/US06/60782, dated Sep. 11, 2007.
International Search Report and Written Opinion issued in PCT/US2008/061316, dated Feb. 24, 2009.
International Search Report and Written Opinion issued in PCT/US2009/034561, dated Aug. 26, 2009.
King et al., "Transport of opioids from the brain to the periphery by P-glycoprotein: peripheral actions of central drugs," *Nature Neuroscience*, 4(3): 268-274, 2001.
Kumar et al., "Site-directed antisense oligonucleotide decreases the expression of amyloid precursor protein and reverses deficits in learning and memory in aged SAMP8 mice," *Peptides*, 21:1769-1775, 2000.

(Continued)

*Primary Examiner* — Jane Zara
(74) *Attorney, Agent, or Firm* — Parker Highlander PLLC

(57) ABSTRACT

There are disclosed agents that inhibit Blood Brain Barrier Proteins (BBBP). Such agents are useful in controlling agents entering and exiting the CNS. This allows for drugs to be more effective and/or allowing side effects of the drugs to be lowered.

3 Claims, 16 Drawing Sheets

OTHER PUBLICATIONS

Figure 1A:
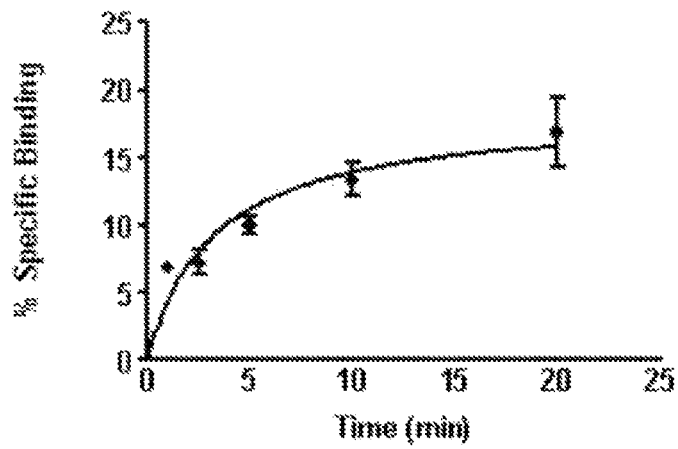

Loscher et al., "Role of drug efflux transporters in the brain for drug disposition and treatment of brain diseases" *Progress in Neurobiology*, 76:22-76, 2005.

Mills et al., "Regulation of amyloid precursor protein cleavage.," *J. Neurochem.*, 72:443-460, 1999.

Poon et al., "Proteomic identification of less oxidized brain proteins in aged senescence-accelerated mice following administration of antisense oligonucleotide directed at the Abeta region of amyloid precursor protein," *Brain Res Mol Brain Res.*, 13:8-16, 2005.

Sandbrink et al., "Beta A4-amyloid protein precursor mRNA isoforms without exon 15 are ubiquitously expressed in rat tissues including brain, but not in neurons," *J. Biol. Chem.*, 269:1510-1517, 1994.

Senechal et al., "Amyloid precursor protein knockdown by siRNA impairs spontaneous alternation in adult mice," *J Neurochem*, 102:1928-1940, 2007.

Su et al., "Drug delivery across the blood-brain barrier: why is it difficult? how to measure and improve it?" *Expert Opin Drug Deliv.*, 3(3):419-35, 2006.

Suzuki et al., "An increased percentage of long amyloid beta protein secreted by familial amyloid beta protein precursor (beta APP717) mutants," *Science*, 264:1336-1340, 1994.

Thuerauf and Fromm et al., "The role of the transporter P-glycoprotein for disposition and effects of centrally acting drugs and for the pathogenesis of CNS diseases," *Eur Arch Psychiatry Clin Neurosci.*, 256(5):281-6, 2006.

Yamatsuji et al., "Expression of V642 APP mutant causes cellular apoptosis as Alzheimer trait-linked phenotype," *EMBO J.*, 15:498-509, 1996.

Yamatsuji et al., "G protein-mediated neuronal DNA fragmentation induced by familial Alzheimer's disease-associated mutants of APP," *Science*, 272:1349-1352, 1996.

Yoshikai et al., "Genomic organization of the human amyloid beta-protein precursor gene," 87:257-263, 1990.

Ali et al., "Nitric oxide activity and isoenzyme expression in the senescence-accelerated mouse p8 model of Alzheimer's disease: effects of anti-amyloid antibody and antisense treatments," *J Gerontol A Biol Sci Med Sci.*, 64(10): 1025-1030, 2009.

Banks et al., "Impairments in brain-to-blood transport of amyloid-β and reabsorption of cerebrospinal fluid in an animal model of Alzheimer's disease are reversed by antisense directed against amyloid-β protein precursor," *J Alzheimers Dis.*, 23(4):599-605, 2011.

Banks et al., "Preproenkephalin targeted antisenses cross the blood-brain barrier to reduce brain methionine enkephalin levels and increase voluntary ethanol drinking," *Peptides*, 27(4):784-796, 2006.

Banks, "Developing drugs that can cross the blood-brain barrier: applications to Alzheimer's disease," *BMC Neuroscience*, 9(Suppl 3): S2, 2008.

Banks, "Measurement of phosphorothioate oligodeoxynucleotide antisense transport across the blood-brain barrier," *Methods Mol. Biol.*, 789:337-342, 2011.

Erickson et al., "Peripheral administration of antisense oligonucleotides targeting the amyloid-β protein precursor reverses AβPP and LRP-1 overexpression in the aged SAMP8 mouse brain," *J. Alzheimers Dis.*, 28(4): 951-960, 2012.

Jaeger et al, "Testing the neurovascular hypothesis of Alzheimer's disease: LRP-1 antisense reduces blood-brain barrier clearance, increases brain levels of amyloid-beta protein, and impairs cognition," *J. Alzheimers Dis.*, 17(3):553-570, 2009.

Neuhas et al., "Blood-brain barrier cell line PBMEC/C1-2 posesses functionally active P-glycoprotein," *Neuroscie Lett.*, 469(2): 224-228, 2010.

\* cited by examiner

FIG. 5A-F
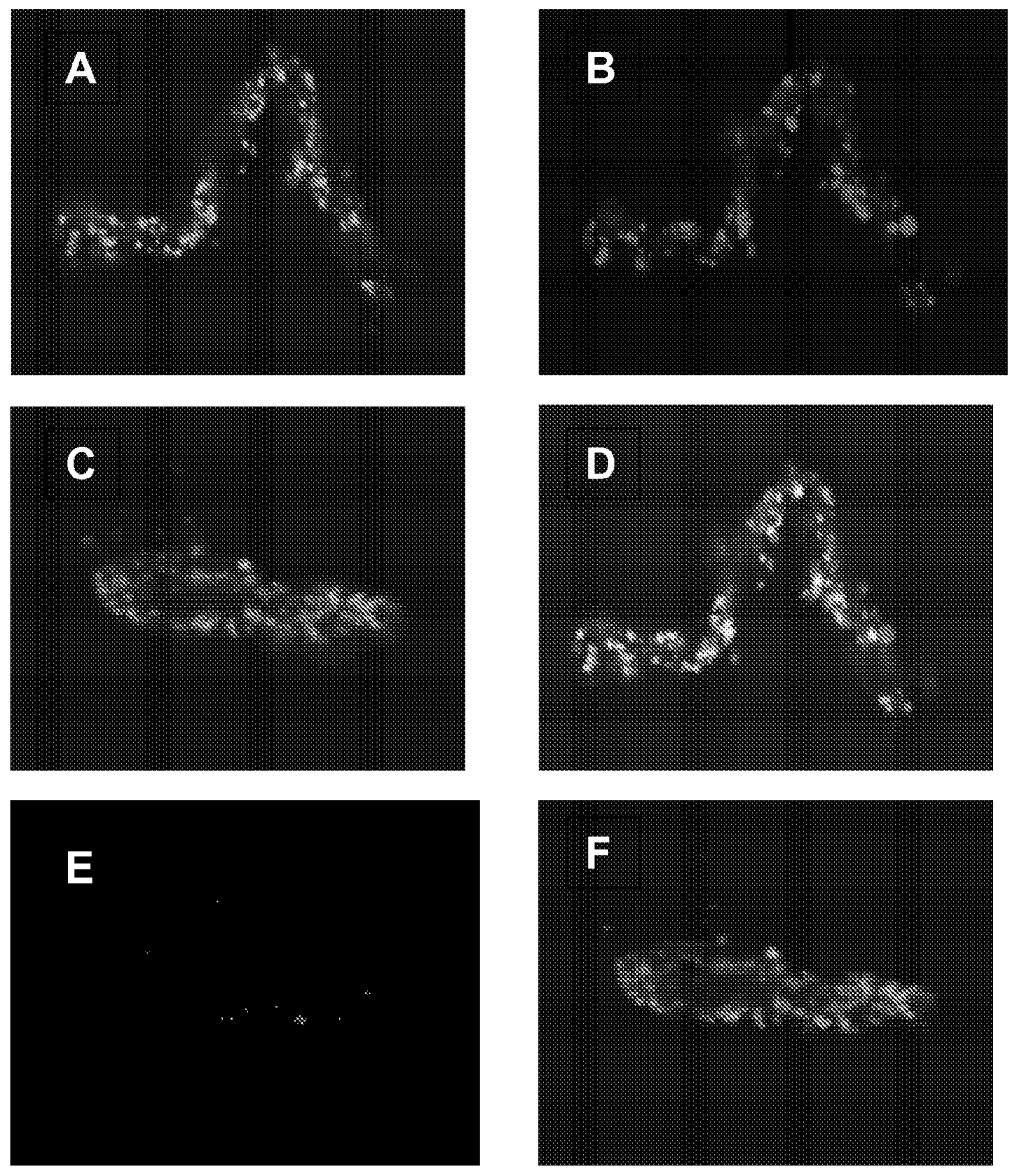

Figure 6I:
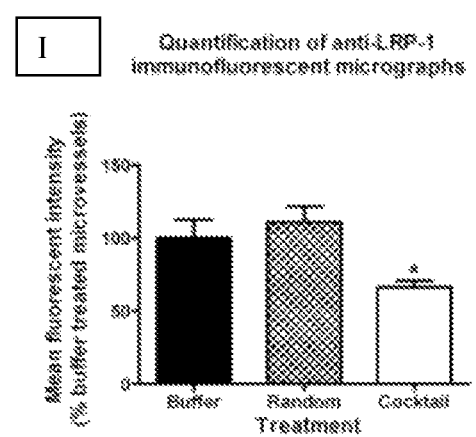

FIG. 6A-B
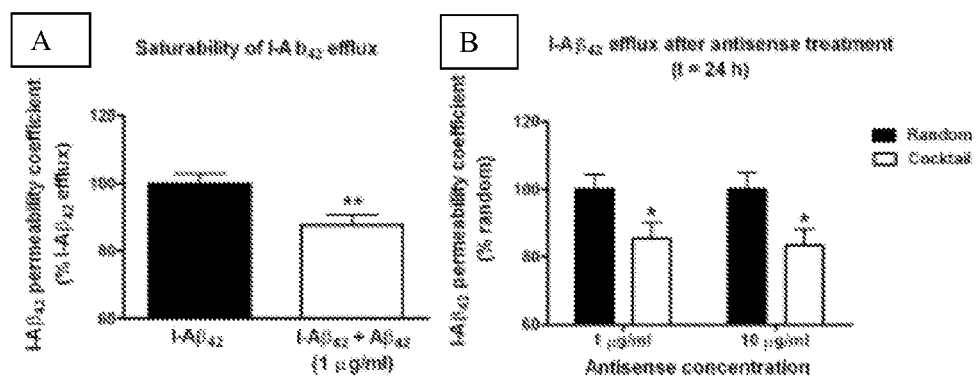

FIG. 6C-H
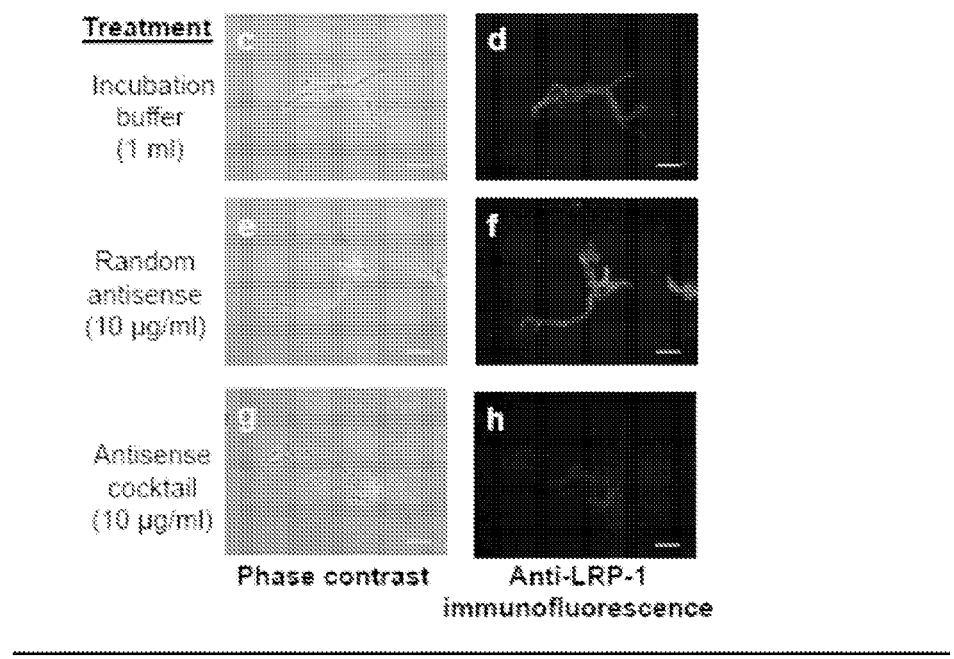

Fig 7A-H
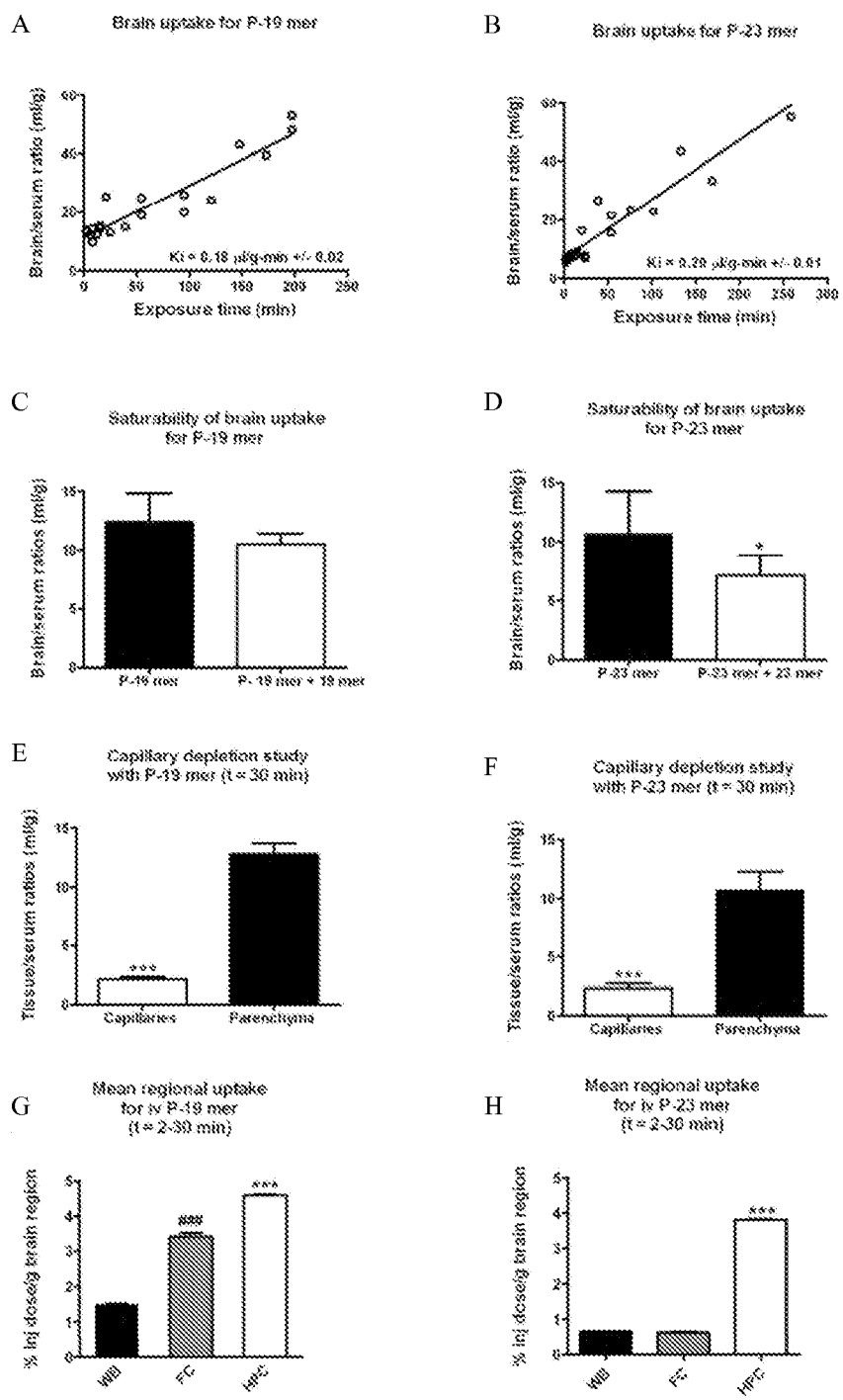

FIG. 8A-E
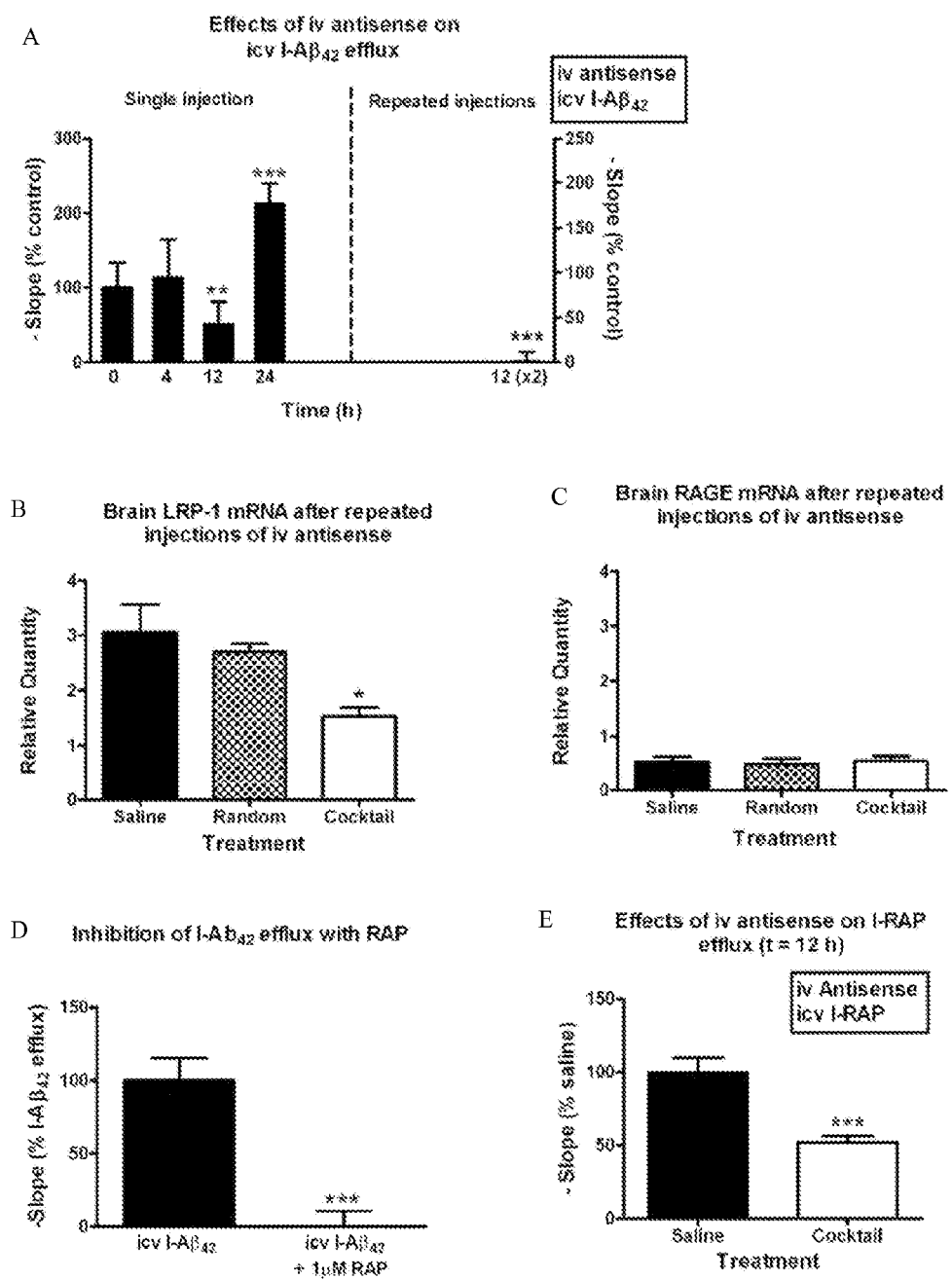

FIG. 10A-F
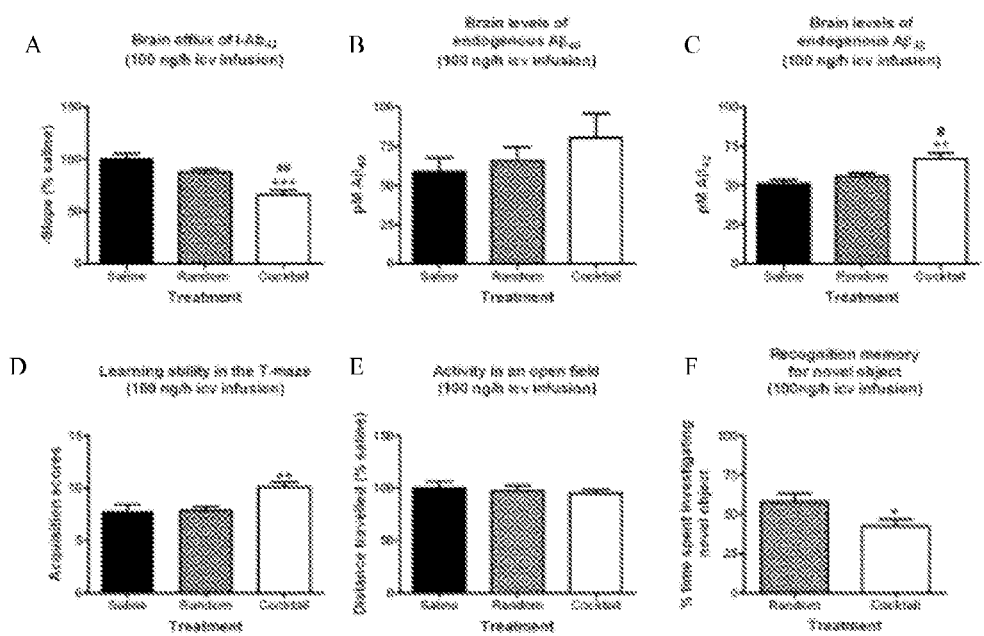

FIG.10G-H
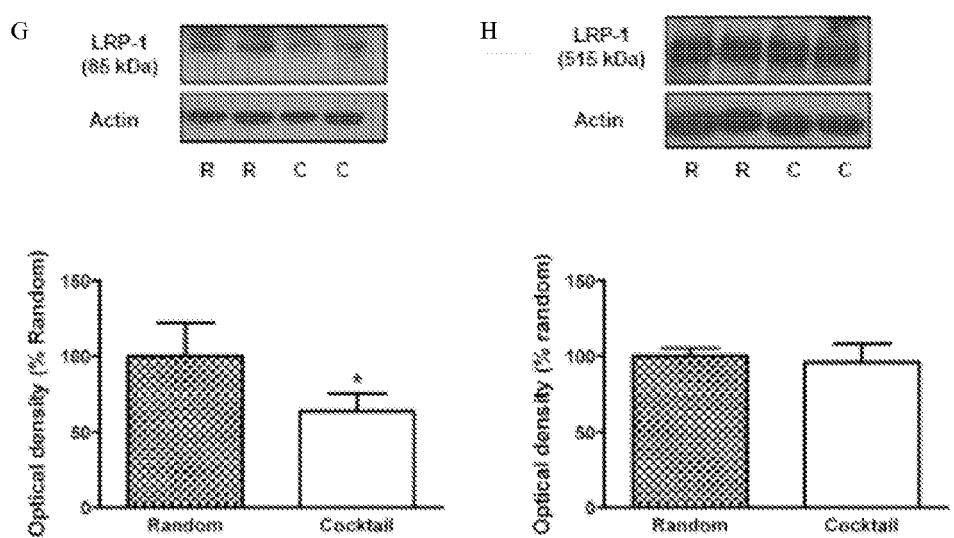

FIG. 11A-B
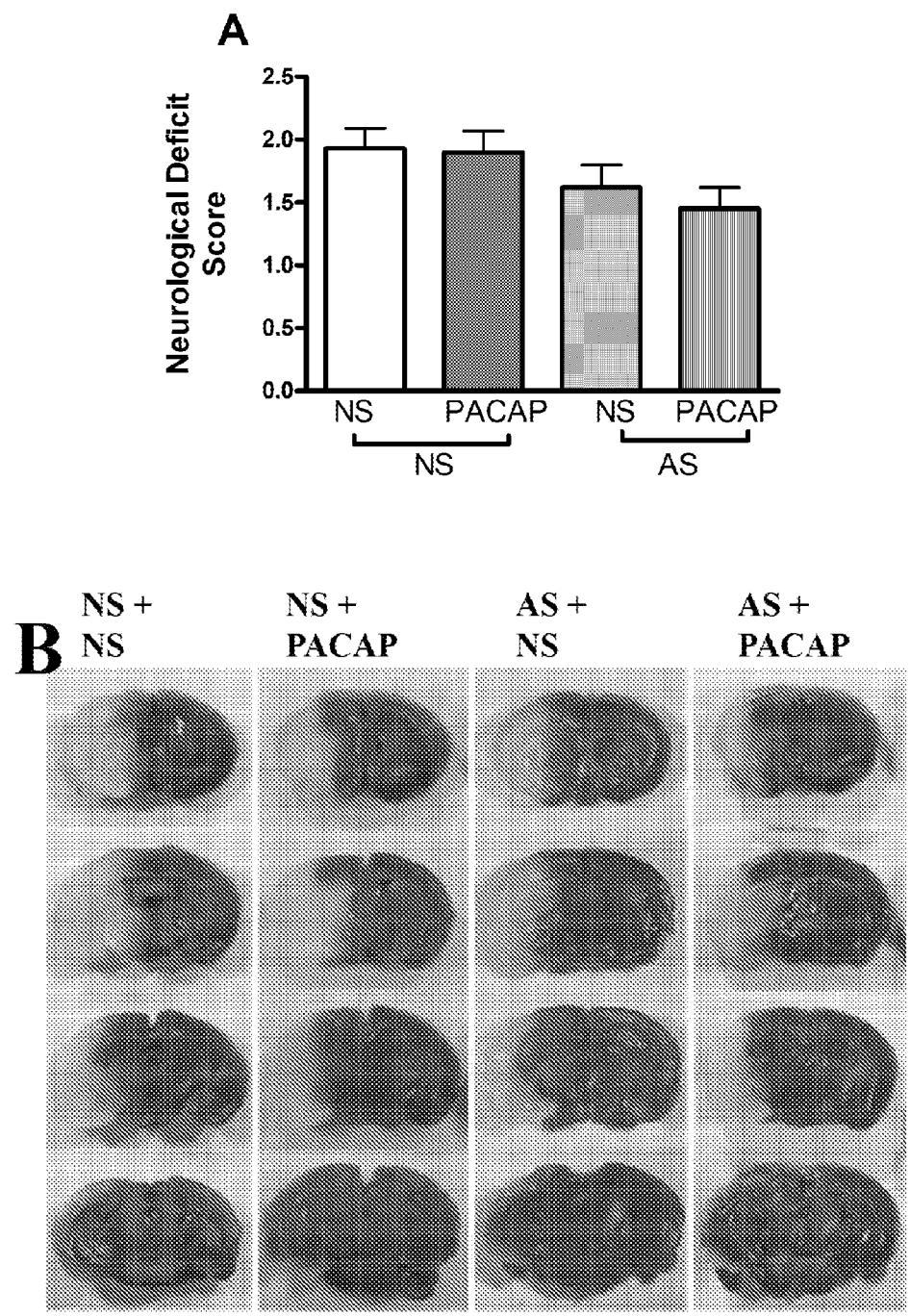

FIG. 11C-D
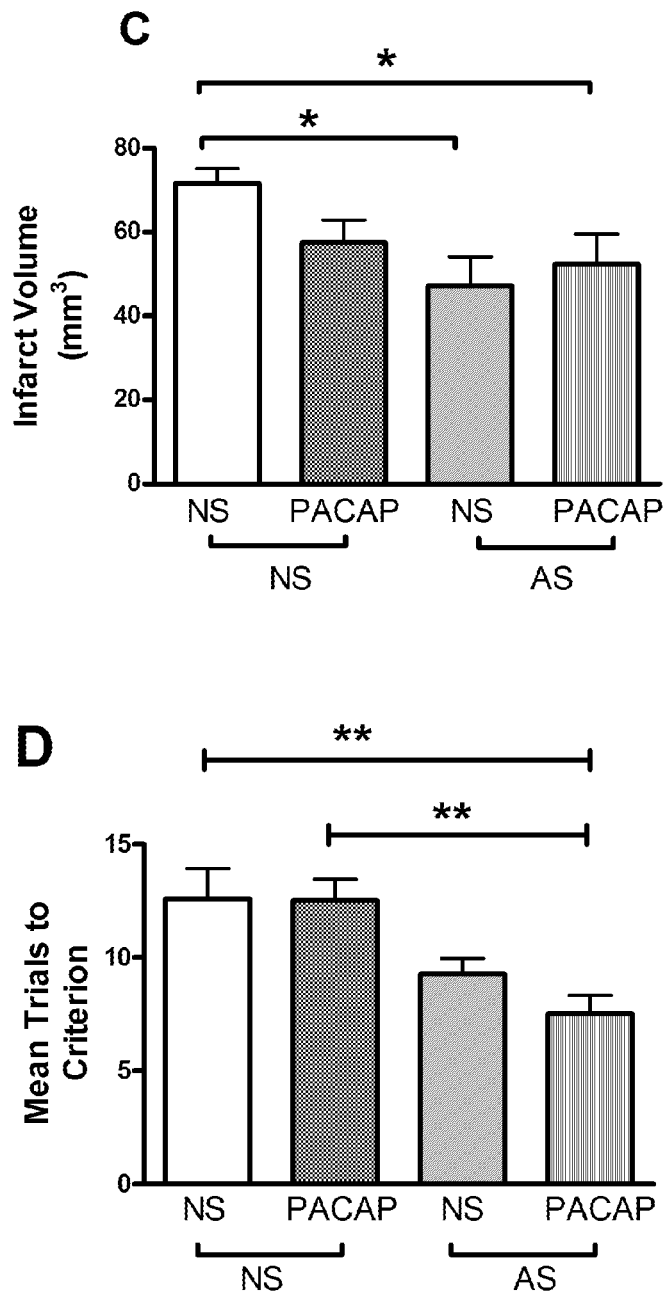

SEQUENCE LISTING

```
<160> NUMBER OF SEQ ID NOS: 40

<210> SEQ ID NO 1
<211> LENGTH: 18
<212> TYPE: DNA
<213> ORGANISM: Mus musculus

<400> SEQUENCE: 1
tccaatgaca ttcatgat                                                  18

<210> SEQ ID NO 2
<211> LENGTH: 15
<212> TYPE: DNA
<213> ORGANISM: Mus musculus

<400> SEQUENCE: 2
ctggtagcct acagc                                                     15

<210> SEQ ID NO 3
<211> LENGTH: 17
<212> TYPE: DNA
<213> ORGANISM: Mus musculus

<400> SEQUENCE: 3
atcgatccct tcttggt                                                   17

<210> SEQ ID NO 4
<211> LENGTH: 10
<212> TYPE: DNA
<213> ORGANISM: Mus musculus

<400> SEQUENCE: 4
tcatgaagcc                                                           10

<210> SEQ ID NO 5
<211> LENGTH: 42
<212> TYPE: DNA
<213> ORGANISM: Mus musculus

<400> SEQUENCE: 5
ggcgcctttg ttcgaaccca catcttcagc aaagaacacc ag                       42
```

```
<210> SEQ ID NO 6
<211> LENGTH: 40
<212> TYPE: DNA
<213> ORGANISM: Mus musculus

<400> SEQUENCE: 6
gatcacgtac acatcgacac cagtcgccat gactgagctt                               40

<210> SEQ ID NO 7
<211> LENGTH: 19
<212> TYPE: DNA
<213> ORGANISM: Mus musculus

<400> SEQUENCE: 7
tgatttggtc tctgcaggc                                                     19

<210> SEQ ID NO 8
<211> LENGTH: 23
<212> TYPE: DNA
<213> ORGANISM: Mus musculus

<400> SEQUENCE: 8
gtgtgggccg atgcaaacag cag                                                23

<210> SEQ ID NO 9
<211> LENGTH: 21
<212> TYPE: DNA
<213> ORGANISM: Mus musculus

<400> SEQUENCE: 9
gagaaggttg tgtgatcttc a                                                  21

<210> SEQ ID NO 10
<211> LENGTH: 20
<212> TYPE: DNA
<213> ORGANISM: Mus musculus

<400> SEQUENCE: 10
ccctgagacg ggactcttta                                                    20

<210> SEQ ID NO 11
<211> LENGTH: 20
<212> TYPE: DNA
<213> ORGANISM: Mus musculus

<400> SEQUENCE: 11
gttggatagg ggctgtgttc                                                    20

<210> SEQ ID NO 12
<211> LENGTH: 20
<212> TYPE: DNA
<213> ORGANISM: Mus musculus

<400> SEQUENCE: 12
agtccacatg ttccctaccg                                                    20

<210> SEQ ID NO 13
<211> LENGTH: 19
<212> TYPE: DNA
<213> ORGANISM: Mus musculus

<400> SEQUENCE: 13
agagccaagg aaggaaagc                                                     19
```

```
<210> SEQ ID NO 14
<211> LENGTH: 18
<212> TYPE: DNA
<213> ORGANISM: Mus musculus

<400> SEQUENCE: 14
ttcctccctg gagaagag                                                  18

<210> SEQ ID NO 15
<211> LENGTH: 18
<212> TYPE: DNA
<213> ORGANISM: Mus musculus

<400> SEQUENCE: 15
tgccacagga ttccatac                                                  18

<210> SEQ ID NO 16
<211> LENGTH: 26
<212> TYPE: DNA
<213> ORGANISM: Rattus norvegicus

<400> SEQUENCE: 16
ggactaaatg ctttcctttg tgacag                                         26

<210> SEQ ID NO 17
<211> LENGTH: 26
<212> TYPE: DNA
<213> ORGANISM: Homo sapiens

<400> SEQUENCE: 17
agcatttagt tagtttcaga gtcttc                                         26

<210> SEQ ID NO 18
<211> LENGTH: 26
<212> TYPE: DNA
<213> ORGANISM: Homo sapiens

<400> SEQUENCE: 18
agcatttagt ctattttaga gtcttc                                         26

<210> SEQ ID NO 19
<211> LENGTH: 26
<212> TYPE: DNA
<213> ORGANISM: Homo sapiens

<400> SEQUENCE: 19
agcatttagt caattttaga gtcttc                                         26

<210> SEQ ID NO 20
<211> LENGTH: 26
<212> TYPE: DNA
<213> ORGANISM: Homo sapiens

<400> SEQUENCE: 20
agcatttagt ccgttttaga gtcttc                                         26

<210> SEQ ID NO 21
<211> LENGTH: 26
<212> TYPE: DNA
<213> ORGANISM: Homo sapiens

<400> SEQUENCE: 21
agcatttagt ctgttttaga gtcttc                                         26
```

```
<210> SEQ ID NO 22
<211> LENGTH: 26
<212> TYPE: DNA
<213> ORGANISM: Homo sapiens

<400> SEQUENCE: 22
agcatttagt cagttttaga gtcttc                                              26

<210> SEQ ID NO 23
<211> LENGTH: 26
<212> TYPE: DNA
<213> ORGANISM: Homo sapiens

<400> SEQUENCE: 23
agcatttagt ccatttcaga gtcttc                                              26

<210> SEQ ID NO 24
<211> LENGTH: 26
<212> TYPE: DNA
<213> ORGANISM: Homo sapiens

<400> SEQUENCE: 24
agcatttagt ctatttcaga gtcttc                                              26

<210> SEQ ID NO 25
<211> LENGTH: 26
<212> TYPE: DNA
<213> ORGANISM: Homo sapiens

<400> SEQUENCE: 25
agcatttagt caatttcaga gtcttc                                              26

<210> SEQ ID NO 26
<211> LENGTH: 26
<212> TYPE: DNA
<213> ORGANISM: Homo sapiens

<400> SEQUENCE: 26
agcatttagt ccgtttcaga gtcttc                                              26

<210> SEQ ID NO 27
<211> LENGTH: 26
<212> TYPE: DNA
<213> ORGANISM: Homo sapiens

<400> SEQUENCE: 27
agcatttagt ctgtttcaga gtcttc                                              26

<210> SEQ ID NO 28
<211> LENGTH: 26
<212> TYPE: DNA
<213> ORGANISM: Homo sapiens

<400> SEQUENCE: 28
agcatttagt cagtttcaga gtcttc                                              26

<210> SEQ ID NO 29
<211> LENGTH: 26
<212> TYPE: DNA
<213> ORGANISM: Homo sapiens

<400> SEQUENCE: 29
agcatttagt tcattttaga gtcttc                                              26
```

```
<210> SEQ ID NO 30
<211> LENGTH: 26
<212> TYPE: DNA
<213> ORGANISM: Homo sapiens

<400> SEQUENCE: 30
agcatttagt ttattttaga gtcttc                                              26

<210> SEQ ID NO 31
<211> LENGTH: 26
<212> TYPE: DNA
<213> ORGANISM: Homo sapiens

<400> SEQUENCE: 31
agcatttagt taattttaga gtcttc                                              26

<210> SEQ ID NO 32
<211> LENGTH: 26
<212> TYPE: DNA
<213> ORGANISM: Homo sapiens

<400> SEQUENCE: 32
agcatttagt tcgttttaga gtcttc                                              26

<210> SEQ ID NO 33
<211> LENGTH: 26
<212> TYPE: DNA
<213> ORGANISM: Homo sapiens

<400> SEQUENCE: 33
agcatttagt ttgttttaga gtcttc                                              26

<210> SEQ ID NO 34
<211> LENGTH: 26
<212> TYPE: DNA
<213> ORGANISM: Homo sapiens

<400> SEQUENCE: 34
agcatttagt tagttttaga gtcttc                                              26

<210> SEQ ID NO 35
<211> LENGTH: 26
<212> TYPE: DNA
<213> ORGANISM: Homo sapiens

<400> SEQUENCE: 35
agcatttagt tcatttcaga gtcttc                                              26

<210> SEQ ID NO 36
<211> LENGTH: 26
<212> TYPE: DNA
<213> ORGANISM: Homo sapiens

<400> SEQUENCE: 36
agcatttagt ttatttcaga gtcttc                                              26

<210> SEQ ID NO 37
<211> LENGTH: 26
<212> TYPE: DNA
<213> ORGANISM: Homo sapiens

<400> SEQUENCE: 37
agcatttagt taatttcaga gtcttc                                              26
```

```
<210> SEQ ID NO 38
<211> LENGTH: 26
<212> TYPE: DNA
<213> ORGANISM: Homo sapiens

<400> SEQUENCE: 38
agcatttagt tcgtttcaga gtcttc                                          26

<210> SEQ ID NO 39
<211> LENGTH: 26
<212> TYPE: DNA
<213> ORGANISM: Homo sapiens

<400> SEQUENCE: 39
agcatttagt ttgtttcaga gtcttc                                          26

<210> SEQ ID NO 40
<211> LENGTH: 26
<212> TYPE: DNA
<213> ORGANISM: Homo sapiens

<400> SEQUENCE: 40
agcatttagt tagtttcaga gtcttc                                          26
```

MODULATION OF BLOOD BRAIN BARRIER PROTEIN EXPRESSION

This application claims the benefit of priority of U.S. Provisional Application No. 60/925,820 filed Apr. 23, 2007 and PCT Application No. PCT/US2008/061316 filed Apr. 23, 2008 the disclosure of which is hereby incorporated by reference as if written herein in its entirety.

This invention was made with Government support under Grant Number: R01 AA12743 awarded by the National Institute on Alcohol Abuse and Alcoholism, Grant Number: R01 NS41863 awarded by the International Institute on Neurological Disorders and Stroke, and R21 DA019396 from the National Instutute on Drug Abuse. The Government has certain right in this invention.

This invention relates generally to the fields of molecular biology, neurobiology, and the use of antisense compounds. More specifically, the invention relates to the identification and modulation of blood brain barrier (BBB) proteins useful for therapies for diseases and injuries of the central nervous system (CNS), diagnostics, and research reagents.

The concept of the blood-brain barrier (BBB) has broadened to reflect new scientific findings: the blood-brain barrier and associated cells (including astrocytes, pericytes, perivascular cells, microglia, and neurons), proteins, and other structures and molecules, this last collectively termed the Neurovascular Unit (NVU), is now seen to comprise the blood-brain barrier. The blood-brain barrier controls the access of drugs to the central nervous system (CNS) by a variety of mechanisms, all of which at some level depend on proteins. The major mechanisms by which the BBB controls access of drugs to the CNS involve (1) influx transporter proteins that conduct the drug from blood to CNS, thus increasing drug concentration in the CNS; (2) efflux transporter proteins that conduct the drug from the CNS to the blood, thus decreasing drug concentration in the CNS; (3) enzymes that destroy the drug as it transits across the BBB; (4) proteins that control the tightness of the BBB; and (5) proteins that control the lipid composition of the membranes that form the BBB, thus altering membrane permeability and function. Manipulation of proteins involved in these mechanisms can also be used to alter access to the CNS of endogenous substances, thus more effectively using the body's endogenous substances as therapeutics. An additional mechanism is possible for endogenous substances as well, involving proteins that are secreted by the BBB into the blood or into the CNS that alter the production of other endogenous substances, and thus access of the CNS to the substance. As proteins are involved in the synthesis and degradation of all non-protein components of the body, it is understood that a substance, including a protein, can be indirectly targeted by targeting the proteins that are involved in the substance's synthesis or catabolism.

It is also understood that the BBB and its functions are controlled by endogenous and exogenous substances through a process by which those substances bind to receptors. Receptor activation then controls the subcellular machinery, functions and secretions of the BBB cells. These receptors are made of proteins and so can be manipulated by the methods outlined here. One mechanism of BBB control involves BBB transporter proteins that conduct drugs from the CNS to the blood, thus decreasing drug accumulation and concentration in the CNS. Because the subcellular machinery synthesizing and catabolizing the transporter also has manipulable protein components, the level of the transporter can be either increased or decreased by targeting the proteins which on balance determine the transporter concentration. This mechanism could be utilized to increase a drug's concentration in the CNS, thus increasing its effectiveness. Such an increase could be achieved by inhibition of a BBB protein that transports a drug out of the CNS. This mechanism could also be utilized to reduce the systemic side effects of a drug that works in the CNS by inhibiting a BBB protein that transports such a drug out of the CNS, thus allowing a lower systemic drug dose to be administered to, and a greater percent of the drug to be retained by, the brain.

Another mechanism of BBB control involves BBB influx transporter proteins that conduct drugs from the blood to the CNS, thus increasing drug concentration in the CNS. A decrease in such a transporter protein would subsequently decrease the amount of a drug entering the CNS. Examples of possible applications of this mechanism include: (a) decreasing an influx transporter protein so that a drug toxic to the CNS can now be administered in higher amounts to treat non-CNS diseases; (b) decreasing an influx transporter protein so that CNS side effects associated with certain drugs are lessened; and (c) increasing an influx transporter protein so that a drug which cannot enter the CNS effectively can now be used to target the CNS.

Another mechanism of BBB control involves inhibiting the proteins which lead to the normal turnover or catabolism of BBB transporters. Inhibition of these proteins would allow the BBB transporters to increase in number. Hence inhibition of influx transporter turnover would allow more drug to enter the brain and inhibition of efflux transporter turnover would allow more drug to leave the brain.

Control of drug access to the CNS also involves proteins that control the tightness of the BBB. The BBB prevents the unrestricted leakage of substances from blood into the CNS by the formation of tight junctions between the endothelial, epithelial, and tanycytic cells that form the BBB. The tight junctions are composed of proteins, and proteins control the rate of transcytosis and cellular characteristics such as the presence, absence, or concentration of fenestrae. Therefore, targeting the proteins that control the tightness of the BBB can increase or decrease the ability of substances to cross the BBB. The tightness of the BBB can be controlled not only as to the rate at which a substance can cross, but can also be regulated as to the size of the molecule which can cross. More aggressive opening usually allows bigger proteins to enter the CNS. Opening the BBB lets in circulating substances as well as the drug and so can be toxic to the CNS. Therefore, the approaches most likely to be useful for this mechanism are first, in those cases where delivery of a drug is for a limited time and for a life-threatening disease, so that treatment is cost-effective compared to CNS toxicity, and second, to prevent, reverse, or control BBB opening induced by disease.

Pituitary adenylate cyclase-activating polypeptide (PACAP) is the newest member of the secretin/glucagon/vasoactive intestinal polypeptide (VIP) family of regulatory peptides. PACAP was originally isolated from ovine hypothalamus (Miyata et al Biochem. Biophys. Res. Commun. 170, 643-648, 1990). There are two biologically active forms, PACAP38 and a C-terminally truncated PACAP27, that are widely expressed both in the central and peripheral nervous systems, and have potent activity in stimulating cAMP production in rat anterior pituitary cells (Arimura et al., Endocrinology 129, 2787-2789, 1991); Moller et al., 57, 725-732, 1993; Mulder et al., Regul. Pept. 59, 121-128, 1995)). Like other neuropeptides, PACAP possesses various physiological functions including neuroprotection, neurotransmission, vasodilatation, and endocrine effects. These effects are mediated through three different PACAP receptor subtypes: $PAC_1$, $VPAC_1$ and $VPAC_2$ (Vaudry et al., Pharmacological Reviews 52, 269-324, 2000); Shioda, Acta Anatomy Nippon 75, 487-

507, 2000). The $PAC_1$ receptor has several splice variants and is specific for PACAP, whereas the other two receptors also bind VIP (Hasimoto et al., Neuron 11, 333-342, 1993); Spengler et al., Nature 365, 170-175, 1993).

The highest concentrations of PACAP are found in the brain and hypothalamus, where PACAP serves as a neurotransmitter. The presence in the central nervous system of receptors that bind PACAP with high affinity and VIP with low affinity has been extensively documented (Cauvin et al., Pept. 35, 161-173, 1991; Gottschall et al., FASEB J. 5, 194-199, 1991; Ohtaki et al., Biochem. Biophys. Res. Commun. 171, 838-844, 1990; Suda et al., Neurosci. Lett. 137, 19-23, 1992. In peripheral tissues, PACAP is present in moderate concentrations in the adrenal gland and testis. Lesser concentrations of PACAP are found in the gastrointestinal tract, lung, epididymis, and ovary (Schivers et al., Endocrinology 128, 3055-3065, 1991)).

One of the most exciting aspects of PACAP is its neuroprotective effects. PACAP38 can protect CAI hippocampal neurons even when given intravenously in nanomolar amounts 24 h after an ischemic event (Uchida et al., Brain Res. 736, 280-286, 1996). The reason such low amounts can be given intravenously is because PACAP38 is transported into brain across the blood-brain barrier (BBB) by a saturable transport system termed peptide transport system-6 (PTS-6) (Banks et al., J. Pharmacol. Exp. Ther. 267, 690-696, 1993. The pharmacokinetic profiling of PTS-6 is complex, having both influx and efflux components (Banks et al., 1993). PACAP38, but not PACAP27, is transported in the blood-to-brain direction by a saturable mechanism, whereas both PACAP38 and PACAP27 are transported in the brain-to-blood direction. The evidence also suggests that separate efflux systems may exist for PACAP38 and PACAP27 because only the efflux of PACAP38 is stimulated by LHRH (Banks et al.1993).

Blood-brain barrier proteins play an important role in regulating the transport of molecules across the BBB. As such, BBB proteins represent an attractive target for modulating the concentration of molecules in the CNS. Thus, it would be of great benefit if methods and compositions could be developed that would modulate the activity or expression of BBB proteins. In particular, modulation of the activity or expression of BBB proteins may be useful in conjunction with the use of therapeutic drugs for the treatment of diseases such as ischemic injury, Alzheimer's disease, neuro-AIDS, seizures and cancer.

The following drawings form part of the present specification and are included to further demonstrate certain aspects of the present invention. The invention may be better understood by reference to one or more of these drawings in combination with the detailed description of specific embodiments presented herein.

Figure 1B:
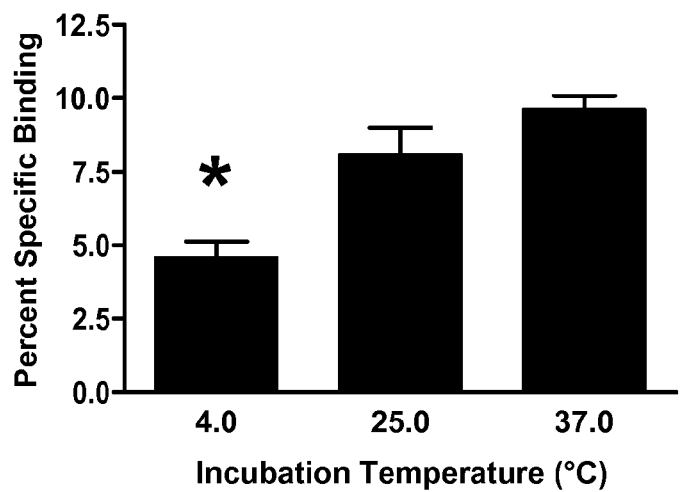
Figure 1C:
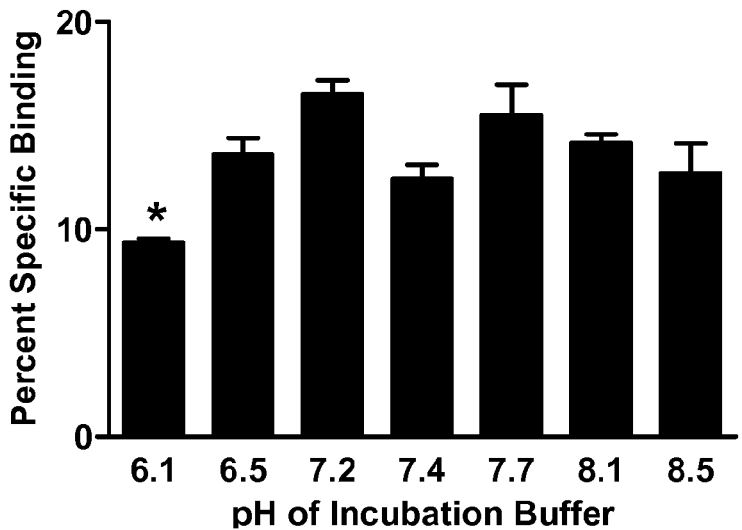

FIGS. 1A-C. Characterization of PACAP27 binding to brain microvessels. FIG. 1A. The effect of incubation time on binding of PACAP27 to mouse brain microvessels. Binding assays were performed as described in the text with 53 pM PACAP27 at room temperature. Each point represented the mean of triplicates. FIG. 1B. The effect of incubation temperature on binding of PACAP27 to mouse brain microvessels. Binding assays were performed as described in the text with 53 pM PACAP27 for 2.5 min. Each point represented the mean of triplicates. * 4° C. is statistically different from 25° C. and 37° C. at p<0.05 probability level. FIG. 1C. The effect of incubation buffer pH on binding of PACAP27 to mouse brain microvessels. Binding assays were performed as described in the text with 53 pM PACAP27 for 2.5 min and at room temperature. Each point represented the mean of triplicates. * pH 6.1 is statistically different from pH values 7.2, 7.7, and 8.1 at p<0.05

Figure 2A:
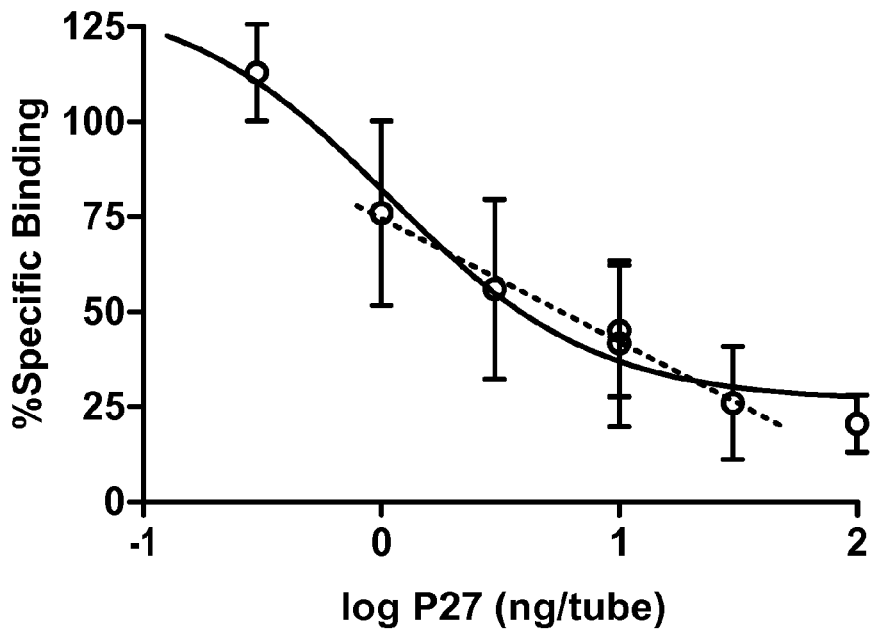
Figure 2B:
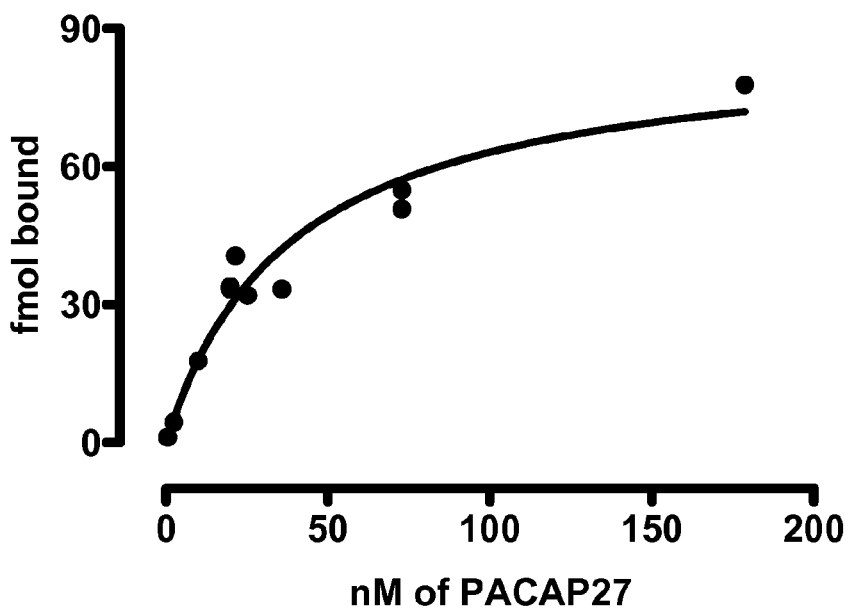

FIGS. 2A-B. Kinetics of PACAP27 binding to brain microvessels. FIG. 2A. Competitive inhibition of PACAP27 binding to mouse brain microvessels. Microvessels were incubated with $^{131}$I-PACAP27 (hereafter referred to as I-PACAP27) and increasing concentrations of unlabeled PACAP27 (1-100 ng/tube) for 2.5 min at room temperature as described in Materials and Methods. An inverse linear relation existed between the log dose of PACAP and specific binding. FIG. 2B. The values for PACAP27 were 87.48∀8.69 fmol for Bmax and 38.56∀8.94 nM for Kd (r=0.9708, n=11). Kinetics analysis was consistent with a single binding site.

Figure 3:
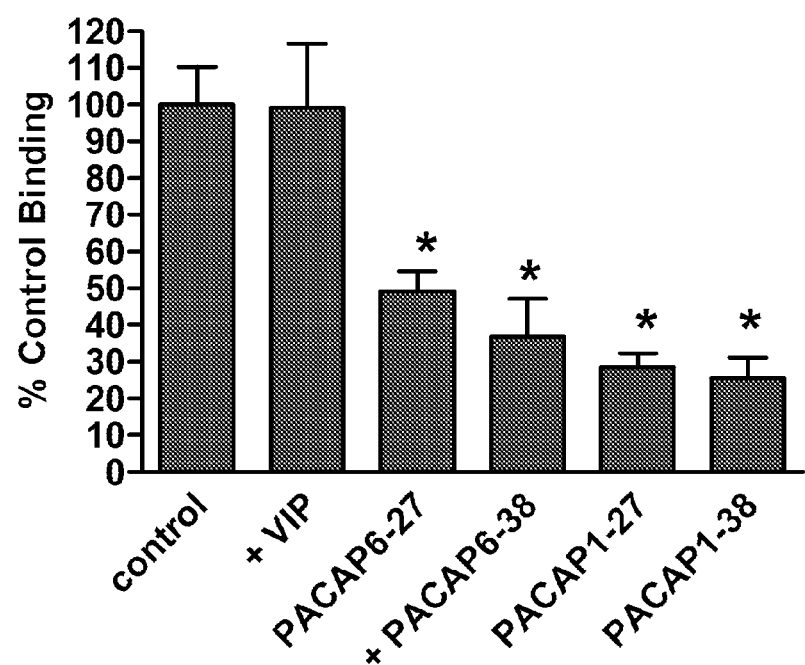

FIG. 3. Displacement of 1-PACAP27 binding by unlabeled PACAP27, PACAP38, PACAP6-27, PACAP6-38 and VIP. The figure also demonstrates the specificity of 1-PACAP27 binding with VIP and PACAP antagonists. Brain microvessels (30 µg protein) were incubated with I-PACAP27 with 50 nM of unlabeled peptides at room temperature for 2.5 min. Results are expressed as a percentage of PACAP27 binding in the absence of unlabeled hormone. * is statistically different from control (p<0.05).

Figure 4A:
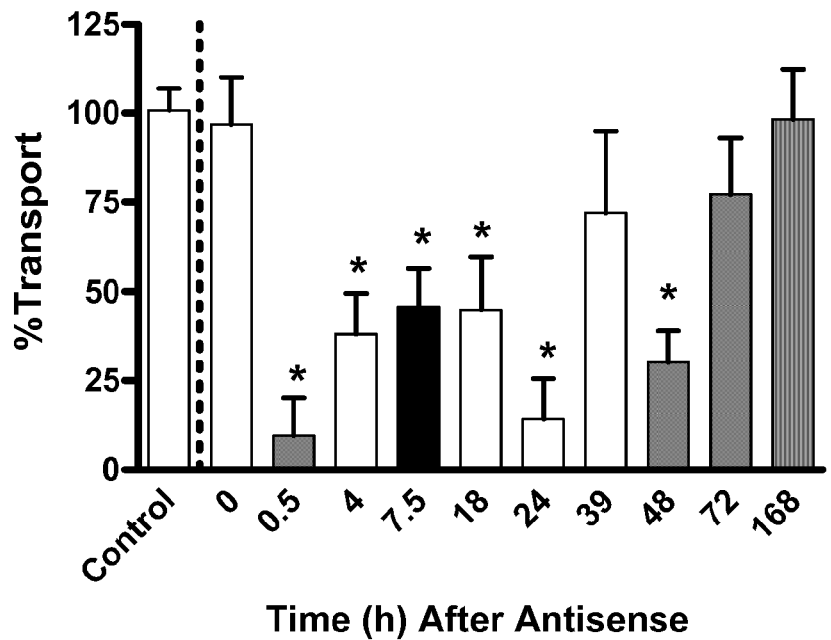
Figure 4B:
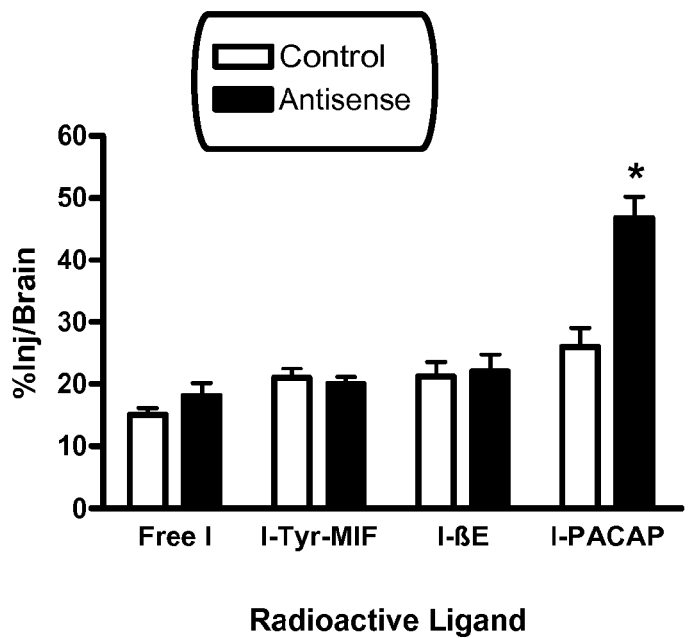
Figure 4C:
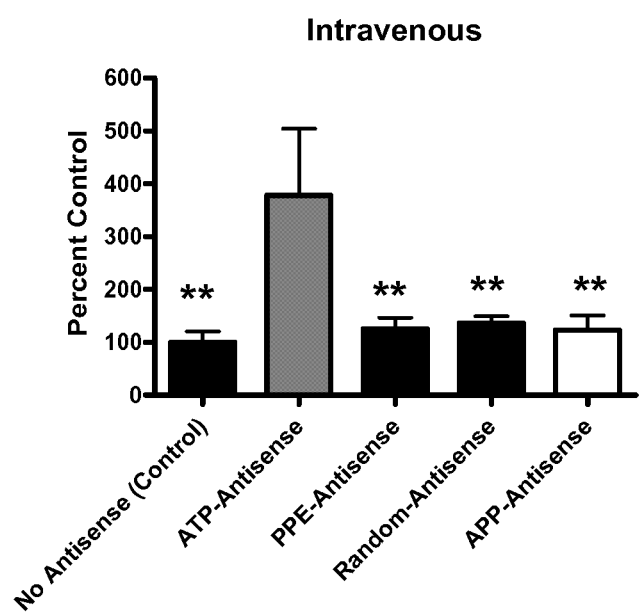

FIGS. 4A-C. Antisense and PACAP. FIG. 4A. Effects of antisense cocktail directed against beat-F1 ATPase on efflux from brain. Cocktail was injected into the lateral ventricle of the brain at t=0 and PACAP27 was injected later at the indicated time. Inhibition of PTS-6 activity was evident 30 min after injection with the effect lasting 24-48 h. FIG. 4B. Antisense cocktail injected into the lateral ventricle of the brain at t=0 had an effect 24 h later on the efflux of I-PACAP27 (I-P27) but not on three other molecules which are transported out of the brain nor on radioactively labeled PACAP38 (I-P38). FIG. 4C. Effects of various antisenses on the blood-to-brain uptake of PACAP27. Antisense to beta-F1 ATPase increased brain retention of I-PACAP27 (I-P27) but not I-PACAP38 (I-P38) consistent with inhibition of PTS-6 efflux activity. Antisenses directed against preproenkephalin (PPE) and against amyloid precursor peptide (APP) and a random antisense had no effect on efflux.

FIGS. 5A-F. Co-localization of beta-F1 ATPase and PACAP in mouse brain microvessels is shown by the yellow spots in FIG. 5C. Isolated micro-vessels were immunostained for beta-F1 ATPase in the presence (FIGS. 5A-C) or in the absence (FIGS. 5D-F) of exogenously added PACAP protein. FIGS. 5A and 5D show beta-F1 ATPase labeling in green. FIGS. 5B and 5E show PACAP labeling in red. FIGS. 5C and 5F show the merged images. Images were taken using a BioRad confocal scanning microscope and merged using the Confocal Assistant software program. Bar=100 µm.

FIG. 6. Effects of antisense cocktail treatment in vitro: BMEC monolayers and isolated mouse brain microvessels. (a) Saturability of I-Aβ42 transport in primary BMEC monolayers. Addition of 1 µg of unlabelled Aβ42 significantly impaired abluminal to luminal efflux of I-Aβ42. (b) Effects of antisense cocktail treatment on primary BMEC monolayers. Treatment with antisense cocktail (at a dose of 1 µg/ml or 10 µg/ml) significantly impaired efflux of I-Aβ42. (n=13-15/group for a, n=8-17/group for b). (c-h) Effect of antisense cocktail on LRP-1 expression in isolated mouse brain microvessels (MBMs). Representative phase contrast (c, e and g) and immunofluorescent (d, f and h) micrographs of the microvessels after 24 h treatment of 1 mL incubation buffer (c and d), random antisense (e and f) or antisense cocktail (10 g/mL) (g and h). Bar=50 m. Quantification of immunofluorescent micrographs (i) shows that cocktail treated microvessels exhibit significantly less mean fluorescent intensity than microvessels treated with random antisense or incubation buffer (n=5-6 slides/group). Data shown as mean+/−s.e.m. *=p<0.05. **=p<0.01.

FIG. 7. CNS pharmacokinetics of iv cocktail PS-ODNS in vivo. (a-b) Brain uptake of iv P-19 mer and (b) P-23 mer cocktail PS-ODNs. The linear relationship between the brain/serum ratios and their relative exposure times (Expt) represents the rate of brain influx (Ki) which is 0.18 μL/g-min+/−0.02 and 0.20 μL/g-min+/−0.01 for the P-19 mer and P-23 mer, respectively. (c-d) Saturability of brain uptake for P-19 mer (c) and P-23 mer (d) cocktail PS-ODNs. Co-administration of 10 μg of unlabeled 23 mer antisense significantly decreased uptake of P-23 mer. Uptake of P-19 mer, however, was not significantly decreased. *=p<0.05. Data shown as mean+/−s.d. (n=8-9/group). (e-f) Distribution of iv P-19 mer (e) and P-23 mer (f) cocktail PS-ODNs between capillary and parenchymal tissues. Both P-Olgs, demonstrated considerable uptake into the target, the brain capillaries. *=p<0.001. (n=4-9/tissue). (g-h) Regional distribution of iv P-19 mer (g) and P-23 mer (h) in the frontal cortex (FC) and hippocampus (HPC). For the P-23mer, mean uptake into the HPC was significantly greater than mean uptake into FC and whole brain (WB). Uptake of the P-19 mer in the HPC was greater than the uptake into the WB, however, it was not significantly different than the uptake per gram of FC. Data shown as mean+/−s.e.m. (n=14-23/brain region). *=p<0.001 versus FC and WB and ### p<0.001 versus WB.

FIG. 8. Effects of acute peripheral cocktail administration in vivo. (a) Effects of acute iv antisense cocktail (4, 12 and 24 h) or saline (0 h) treatment on brain efflux of icv I-Aβ42 in vivo. A single iv injection of 7 μg antisense cocktail significantly impaired brain efflux of I-Aβ42 at t=12 h. Efflux at t=24 h, however, had significantly rebounded in the antisense cocktail treated mice. (n=11-14/group). Mice that received two iv injections of antisense cocktail (right side of graph) showed a nearly total impairment in I-Aβ42 efflux at t=12 h and quantification of brain mRNA (b) revealed that this impairment correlated with a significant decrease in LRP-1 mRNA. (c) Levels of mRNA for another BBB transporter, RAGE, were not affected by this treatment (n=4/group for b-c). (d) Effects of acute iv cocktail treatment on efflux of intrahippocampal I-Aβ42. Administration of 7 μg iv antisense cocktail significantly impaired efflux of intrahippocampally administered I-Aβ42 at t=12 h. (e) Effects of iv antisense cocktail on I-RAP efflux at t=12. Treatment with antisense cocktail was associated with significantly impaired brain clearance of I-RAP (n=13/group). For all figures, data shown as mean+/−s.d. *=p<0.05, =p<0.01, *=p<0.001.

Figure 9:
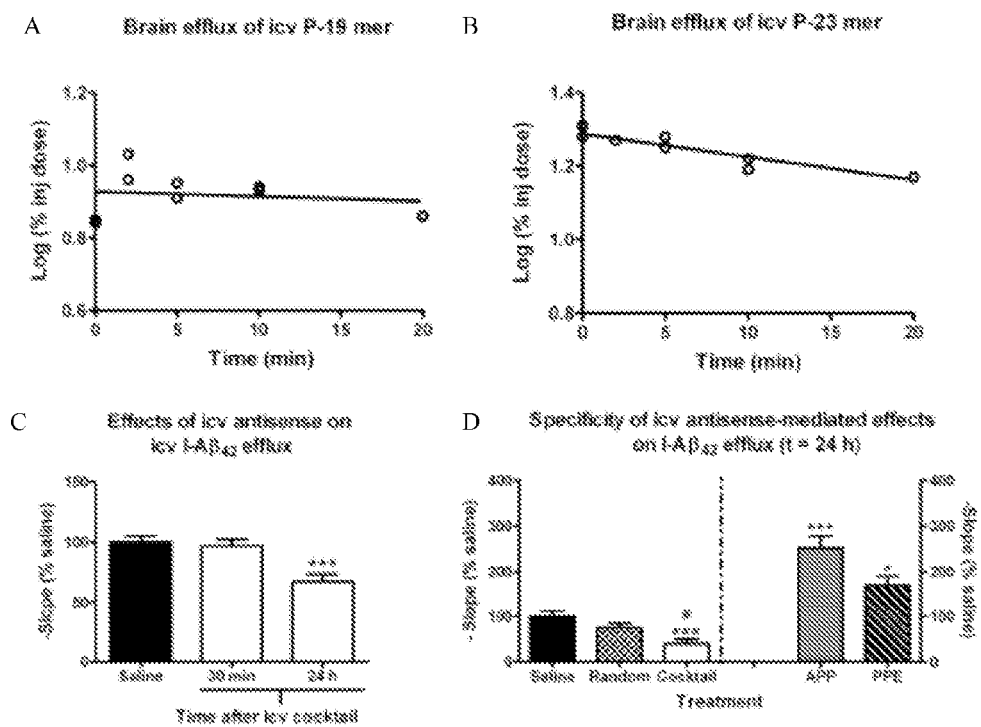

FIG. 9. Effects of acute central cocktail administration of antisense in vivo. (a-b) Brain efflux of icv P-19 mer (a) and P-23 mer (b) antisense cocktail PS-ODNs. The slope of the line represents the rate of brain efflux which was 0.0013% and 0.0063% of the injected dose/min for the P-19 mer and P-23 mer, respectively. (n=2-3 mice/time point). (c) Effects of acute icv antisense cocktail (200 ng dose) on brain efflux of icv I-Aβ42. Treatment with antisense cocktail significantly impaired I-Aβ42 efflux at t=24 h, but not at t=30 min. (n=12-15/group). *=p<0.001. (d) Specificity of cocktail-mediated effects of I-Aβ42 efflux. Treatment with icv antisense cocktail produced a significant decrease in I-Aβ42 efflux compared to saline (*=p<0.0001) and random (#=p<0.05) antisense treated mice. Treatment with icv APP antisense or PPE antisense, however, produced a significant increase in I-Aβ42 efflux compared to saline treated mice. *=p<0.05, ***=p<0.001. Data shown as mean+/−s.d. (n=12-15/group).

FIG. 10. Effects of chronic central cocktail infusion on I-Aβ42 efflux, brain levels of Aβ40 and Aβ42, learning ability, recognition memory and brain levels of LRP-1 protein in mice. (a) Compared to random treated mice, mice receiving a 1 week icv infusion of 100 ng/h cocktail demonstrated significantly decreased brain efflux of I-Aβ42. (n=12-16/group). ##=p<0.01 vs. cocktail, *=p<0.0001 vs. saline. (b-c) Brain levels of either Aβ40 or Aβ42 were quantified by ELISA after the 1 week infusion. Assessment of Aβ40 (b) did not reveal a significant difference between the three treatment groups, however, mice treated with antisense cocktail did demonstrate significantly higher levels of Aβ42 (c) compared to both saline and random treated mice. (for b-c, n=5-6/group). #=p<0.05 vs. random, =p<0.01 vs. saline. (d-f) Behavioral analysis for learning ability and memory in mice treated with 100 ng/h infusion. (d) Mice treated with icv antisense cocktail for one week demonstrated significantly increased mean acquisition scores in the T-Maze compared to saline and cocktail treated mice. (n=12-15/group). **=p<0.01. (e) Assessment of locomotor activity in an open field showed that the icv infusion did not affect overall activity level in any of the treatment groups. (f) Analysis of amount of time spent investigating a novel object revealed that mice treated with a 2 week icv infusion of antisense cocktail (100 ng/h) demonstrated a significant deficit in recognition memory compared to random treated mice. (n=11-17/group). p<0.05. (g-h) Western blot analysis of LRP-1 levels in brain homogenates isolated from mice treated with the 1 week icv infusion of either cocktail or random antisense (100 ng/h). (g) Western blot for small (85 kDa) subunit of LRP-1 shows that mice treated with antisense cocktail ("C") demonstrate significantly less band intensity compared to random ("R") infused mice. (*=p<0.05). (h) Analysis of the large (515 kDa) subunit, however, did not reveal a significant difference between the two treatment groups. (for g-h, n=1 mouse/band). Data shown as mean+/−s.e.m. in b-c and g-h. Data shown as mean+/−s.d. in all other figures.

FIG. 11. Effects of antisense cocktail directed against beta-F1 ATPase on models of brain insult. Antisenses (AS) or saline (NS) were injected into the jugular vein at 24 hours before ischemia. (A) Neurological deficient scores 2 hours after pMCAO. ANOVA showed a statistically significant effect for antisense treatment, but Newman-Keuls post-test found no differences among the individual groups. (B) Representative images of TTC-stained brain sections 24 h after pMCAO ischemia. (C) Infarct volumes 24 h after pMCAO in the PACAP+Antisense treated groups are less than those in the saline-saline treated group (p<0.05). (D) Effects of PACAP27 and Antisense on acquisition in the SAMP8, a mouse model of Alzheimer's disease. PACAP+Antisense improved learning in comparison to NS treated mice (p<0.01) and mice treated only with PACAP (p<0.01).

This invention relates to the identification and modulation of blood-brain barrier (BBB) proteins. The invention also contemplates modulation of BBB proteins in conjunction with additional therapeutic treatments. One aspect of this invention relates to antisense compound interactions with certain messenger ribonucleic acids (mRNAs) or deoxyribonucleic acids (DNAs) involved in the synthesis of BBB proteins. In certain embodiments, antisense oligonucleotides designed to hybridize to the mRNA encoding certain BBB proteins are provided. These oligonucleotides have been found to modulate the activity of BBB protein-encoding RNAs or DNAs, and thus to modulate the synthesis of such proteins. This invention also contemplates oligonucleotides useful in assays and diagnostics.

One specific aspect of this invention concerns the identification of and/or modulation of BBB efflux pumps. Efflux pumps are a group of proteins that transport molecules out of the CNS to the blood. Inhibition of such efflux pumps could increase the effectiveness of certain treatments that are hindered by an inability to deliver certain drugs to the CNS. For example, many antibiotics accumulate in the CNS poorly because they are transported in the CNS-to-blood direction by many different efflux pumps. The common antibiotic penicillin accumulates in the CNS poorly because of an organic efflux pump. Currently, blockers such as probenecid must be given in conjunction with penicillin to prevent CNS to blood transport. Unfortunately, for many efflux pumps there are no known or non-toxic inhibitors or the inhibitors are ineffectual or unreliable. Inhibition of efflux pump expression would allow the antibiotic to accumulate in the CNS without having to rely on the existence or activities of blockers.

AIDS virus in the CNS is very difficult to treat because of poor accumulation of AIDS fighting drugs in the CNS. One class of drugs used to fight the AIDS virus comprises the protease inhibitors. Some of these drugs have poor penetration into the CNS because they are ligands for P-glycoprotein (Pgp), a pump located at the BBB that transports its ligands in the CNS to blood direction. Inhibition of Pgp would allow increased penetration of protease inhibitors into the CNS, and so increase the effectiveness of treating the AIDS virus in the CNS. Another drug used to fight the AIDS virus is azidothymidine. It also has poor penetration into the CNS because it is a ligand for the organic ion carrier, another pump located at the BBB that transports its ligands in the CNS-to-blood direction. Inhibition of the organic ion carrier would allow increased penetration of azidothymidine into the CNS and so increase effectiveness of treating the AIDS virus in the CNS.

One third of patients suffering from epilepsy are resistant to most anti-epileptic drugs. These anti-epileptic drugs are ligands for P-glycoprotein (Pgp), a pump located at the BBB that transports its ligands in the CNS-to-blood direction. It is thought that patients resistant to anti-epileptic drugs overexpress P-glycoprotein. Inhibition of Pgp expression would allow increased penetration of anti-epileptic drugs into the brain and so increase the effectiveness of treating seizures. Further, patients usually require life-time administration of anti-epileptic drugs and may eventually develop side effects of non-brain tissues such as weakening of the bones. Inhibition of Pgp would allow a higher percent of a dose of anti-epileptic drug to accumulate in brain tissue by preventing transport of the drug from the CNS to the blood, and a lower efficacious dose to be administered to prevent or treat seizures. Blood levels of anti-epileptic drugs would be lower, and side effects on non-brain tissues would be reduced.

Studies have shown that Pgp can transport a wide range of structurally diverse and pharmacologically active compounds from the CNS to systemic circulation. For example, Pgp was originally identified in studies exploring the resistance of cancers to chemotherapeutic drugs. Thus, inhibition of Pgp expression would allow increased accumulation of chemotherapeutic drugs in the CNS and so increase the effectiveness of treating CNS tumors. One skilled in the art would recognize that such an approach could be used to enhance the effectiveness of a wide range of compounds that are currently hindered by Pgp-mediated transport out of the CNS. Such enhanced effectiveness could include being able to use lower concentrations of therapeutic compounds and the lessening of systemic side effects.

Another aspect of the invention contemplates the modulation of BBB efflux proteins to alter the concentration of endogenous substances in the CNS. Inhibition of an efflux transporter protein would allow specific endogenous substances to accumulate in the CNS. An example of a natural substance so affected is methionine enkephalin (Met-enk). The level of Met-enk in the brain correlates with the amount of ethanol an animal will voluntarily consume so that a low level of Met-enk in the brain results in increased alcohol consumption. Met-enk also has anti-seizure activity, with the consequence that if Met-enk levels drop too low, seizures can occur. The level of Met-enk is partly controlled by peptide transport system-1 (PTS-1), a protein that transports Met-enk out of the brain. In alcohol addiction or physical dependence, PTS-1 activity is shut off, thus conserving brain levels of Met-enk. When drinking stops, PTS-1 recovers quickly (within hours) and so pumps Met-enk out of the brain. This drop in Met-enk may be the basis of alcohol withdrawal seizures. Inhibition of PTS-1 would conserve brain Met-enk and so prevent alcohol withdrawal seizures.

In a further example, the concentration of amyloid beta (Aβ) in the brain may be altered by modulation of a BBB efflux protein. Accumulation of Aβ in the brain is thought to play a causal role in Alzheimer's disease onset and pathology. The level of Aβ may be partly controlled by low density lipoprotein receptor related protein-1 (LRP-1). LRP-1 is thought to be the primary transporter involved in BBB-mediated efflux. Studies have shown that impaired vascular clearance from the brain may increase cerebral amyloid burden, and thus may increase the probability of developing AD pathology. Currently, no model exists for the validation of this hypothesis in vivo because deletion of the gene that encodes LRP-1 will produce embryonic lethality in mice. The hypothesis may however be tested by in vivo inhibition of LRP-1 in mice as contemplated by the present invention. After LRP-1 inhibition, Aβ concentrations in the brain as well as cognitive impairment may be quantified.

Yet another aspect of this invention contemplates identification of an efflux component of the PTS-6 system and its inhibition. Specifically, such component is beta-F1 ATPase, and an aspect of the invention relates to the use inhibitors of beta-F1 ATPase in combination with PACAP27 in neuroprotective methods. PACAP is promising as a CNS treatment because of its neuroprotective effects. However, the accumulation in the brain of intravenously administered PACAP38 and especially of PACAP27 is limited by the presence of efflux activity. Inhibition of the efflux component of PTS-6 would be expected to enhance the accumulation by brain of intravenously administered PACAP and so increase its therapeutic effects. To date, no peptide transporter for PACAP has been isolated from BBB tissue. The present invention represents the first isolation of a peptide transporter from BBB tissue and shows that beta-F1 ATPase is the PTS-6 efflux component for PACAP27. Inhibition of beta-F1 ATPase by antisense compounds increased blood-brain retention of PACAP27. The peptide transporter for PACAP38 can be identified and inhibited by an antisense oligonucleotide similarly according to this teaching. It is further understood that any peptide transporter of the BBB can be identified and inhibited by an oligonucleotide in a similar fashion.

Blood-Brain Barrier Influx Transporters

Another mechanism of BBB control involves BBB influx transporter proteins that conduct drugs from the blood to the CNS, thus increasing drug concentration in the CNS. A decrease in the concentration of such a transporter protein would subsequently decrease the amount of a drug that is a ligand for that transporter entering the CNS. Because the subcellular machinery synthesizing and catabolizing the transporter also has manipulable protein components, the level of the transporter can be either increased or decreased by targeting the proteins which on balance determine the transporter concentration. Examples of possible applications of this mechanism include: (a) decreasing an influx transporter protein so that a drug toxic to the CNS can now be administered in higher amounts to treat non-CNS diseases; (b) decreasing an influx transporter protein so that CNS side effects associated with certain drugs are lessened; and (c) increasing an influx transporter protein so that a drug which cannot enter the CNS effectively can now be used to target the CNS.

An illustrative example of increasing an influx transporter protein is represented by lysosomal storage diseases that affect the CNS. These congenital diseases are the result of genetic errors in which a vital protein enzyme is missing in the brain so that endogenous substances increase to toxic levels. Newborns express a protein transporter at the BBB that transports this enzyme into the CNS. Therefore, newborns treated systemically with this enzyme do not develop the symptoms of lysosomal storage disease in the CNS because the enzyme is able to enter the brain. With aging, however, production of this transporter falls to near zero and so treatment with enzyme is ineffectual. Reintroduction or enhanced production of this enzyme transporter at the BBB would allow older children and adults to be treated with enzyme, thus preventing toxicity and death from lysosomal storage diseases.

Another example illustrating the benefits of increasing an influx transporter protein is the use of L-dopa to treat Parkinson's disease. L-dopa is transported across the BBB but it is also rapidly cleared from the blood so that L-dopa must be administered at high doses and with a blocker of peripheral uptake and clearance. If the levels of the BBB influx transporter were increased, more L-dopa could be transported into the CNS. As a result, L-dopa could be administered at lower doses and without blockers of peripheral uptake.

Yet another example illustrating the benefits of increasing an influx transporter protein is illustrated by the use of insulin to treat CNS conditions. Insulin has many effects within the CNS, including the suppression of appetite (useful in the treatment of obesity), promoting brain growth, protection from insults such as stroke, and improving memory in patients with Alzheimer's disease. However, administration of insulin systemically produces hypoglycemia, which can be life-threatening. Insulin crosses the BBB in low amounts by way of a saturable transport system. Increasing this transporter protein would allow lower doses of insulin to be given systemically, so that therapeutic levels of insulin could be attained and/or maintained in the CNS while side effects, such as hypoglycemia, could be avoided or reduced.

An example in which opening of the BBB would be beneficial is in the treatment of brain cancers. Most drugs used to treat brain cancers cross the BBB poorly. Currently, a limited number of centers around the US (8) treat otherwise fatal brain cancers by opening the BBB using an aggressive technique of infusing hypertonic solutions directly into brain blood vessels. Opening the BBB by protein manipulation could work as well as hyperosmotic opening, be more widely available, offer more control as to duration and size of molecule for BBB opening, and be less toxic and safer.

An example in which closing of the BBB would be beneficial is in hypertensive encephalopathy. When blood pressure is extremely high, the BBB opens, which is toxic to brain. It was once thought that this opening was entirely due to pressure, but more recent work suggests that many of the substances that cause an elevation in blood pressure, such as angiotensin II, also act directly on the BBB to affect BBB proteins that control blood-brain barrier tightness. Blocking the opening induced by these substances could be accomplished by decreasing the production of their receptor sites at the BBB or inhibiting any of the subcellular protein-mediated steps though which the substances (e.g., angiotensin II) affect BBB tightness.

The present invention relates to compounds, particularly antisense oligonucleotides, for use in modulating the expression of one or more BBB proteins, thus modulating the passage of molecules across the BBB, and ultimately modulating the concentration of molecules in the CNS. In one embodiment, this is accomplished by providing oligonucleotides which specifically hybridize with one or more nucleic acid molecules, for example messenger RNA (mRNA), encoding BBB proteins.

Oligonucleotides have recently become accepted as drugs for the treatment of disease states in animals and man. For example, workers in the field have now identified antisense, triplex and other oligonucleotide therapeutic compositions which are capable of modulating expression of genes implicated in viral, fungal and metabolic diseases. Numerous antisense oligonucleotide drugs have been safely administered to humans and a number of clinical trials are presently underway. Efficacy has been demonstrated for several oligonucleotide drugs, directed to both viral and cellular gene targets. It is thus established that oligonucleotides can be useful therapeutics.

As used herein, the terms "target nucleic acid" and "nucleic acid molecule encoding a BBB protein" have been used for convenience to encompass DNA encoding a BBB protein, RNA (including pre-mRNA and mRNA or portions thereof) transcribed from such DNA, and also cDNA derived from such RNA. The hybridization of a compound with its target nucleic acid is generally referred to as "antisense". Consequently, the mechanism believed to be included in the practice of some embodiments is referred to herein as "antisense inhibition." Such antisense inhibition is typically based upon hydrogen bonding-based hybridization of oligonucleotide strands or segments such that at least one strand or segment is blocked, cleaved, degraded, or otherwise rendered inoperable. In this regard, it is presently common practice to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One result of such interference with target nucleic acid function is modulation of the expression of one or more BBB proteins.

An antisense compound is hybridizable when binding of the compound to the target nucleic acid interferes with the normal function of the target nucleic acid to cause a loss of activity, and it is specifically hybridizable when there is also a sufficient degree of complimentarily to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

"Specifically hybridizable" and "complementary" are terms which are used to indicate a sufficient degree of precise pairing or complimentarily over a sufficient number of nucleobases such that stable and specific binding occurs between the oligonucleotide and a target nucleic acid or related group of such nucleic acids, ideally to the exclusion of non-targeted nucleic acids.

The sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). For example, an antisense compound in which 18 of 20 nucleobases of the antisense compound are complementary to a target region, and would therefore specifically hybridize, would represent 90 percent complimentarity. In this example, the remaining non-complimentary nucleobases may be clustered or interspersed with complementary nucleobases and need not be contiguous to each other or to complementary nucleobases. As such, an antisense compound which is 18 nucleobases in length having 4 (four) non-complimentary nucleobases which are flanked by two regions of complete complimentarity with the target nucleic acid would have 77.8% overall complimentarity with the target nucleic acid and would thus fall within the scope of the described embodiments. Percent complimentarity of an antisense compound with a region of a target nucleic acid can be determined routinely using BLAST programs (basic local alignment search tools) and Power-BLAST programs known in the art (Altschul et al., J. Mol. Biol., 1990, 215, 403 410; Zhang and Madden, Genome Res., 1997, 7, 649 656).

Percent homology, sequence identity, or complimentarity can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482 489). In some embodiments, homology, sequence identity or complimentarity, between the oligomeric and target is between about 50% to about 60%. In further embodiments, homology, sequence identity or complimentarity, is between about 60% to about 70%. In yet further embodiments, homology, sequence identity or complimentarity, is between about 70% and about 80%. In yet further embodiments, homology, sequence identity or complimentarity, is between about 80% and about 90%. In yet further embodiments, homology, sequence identity or complimentarity, is about 90%, about 92%, about 94%, about 95%, about 96%, about 97%, about 98%, about 99% or about 100%.

Two or more antisense sequences may be contained in one molecule. Alternatively, two or more sequences each comprising an antisense molecule can be contained in one presentation.

The "Blood-brain barrier" ("BBB") in the context of this invention is defined as the brain vascular barrier (comprised of brain endothelial cells and other elements of the neurovascular unit generally defined as the collection of pericytes, astrocytes, microglia, and neurons and other cells, usually perivascular, which endow the brain vasculature with blood-brain barrier properties), the choroid plexus (comprised of ependymal cells, epithelial cells, and other cells which endow the choroid plexus with blood-brain barrier properties), the tanycytic barrier (comprised of tanycytes and other cells which endow the tanycytic layer between circumventricular organs and adjacent brain tissues with blood-brain barrier properties), and the specialized blood-barriers of the blood-retinal barrier, the meninges, the blood-nerve barriers, and the blood-labyrinth barrier of the inner ear, and the blood-spinal cord barrier.

"Hybridization" in the context of this invention means the pairing of complementary strands of oligomeric compounds. In the embodiments described herein, an exemplary mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

Terms such as "modulation" or "modulating" in the context of this invention, mean either inhibition or stimulation; i.e., either a decrease or increase in expression, function, or rate. Inhibition is often the form of modulation of expression and mRNA is often a target nucleic acid. Modulation can be measured in ways which are routine in the art including but not limited to Northern blot assay of mRNA expression, reverse transcriptase PCR, Western blot or ELISA assay of protein expression, immunoprecipitation assay of protein expression, ligand binding assays, and ligand transport assays.

"Oligomeric compound" in the context of this invention refers to a polymer or oligomer comprising a plurality of monomeric units.

"Oligonucleotide", in the context of this invention, refers to an oligomer or polymer of ribonucleic acid (RNA) or deoxyribonucleic acid (DNA) or mimetics, chimeras, analogs and homologs thereof. This term includes oligonucleotides composed of naturally-occurring nucleobases, sugars and covalent internucleoside (backbone) linkages as well as oligonucleotides having non-naturally-occurring portions which function similarly.

"Pharmaceutically acceptable salts" in the context of this invention refers to physiologically and pharmaceutically acceptable salts of the compounds described herein: i.e., salts that retain the desired biological activity of the parent compound and do not impart undesired toxicological effects thereto.

The phrase "stringent hybridization conditions" or "stringent conditions" in the context of this invention refers to conditions under which a compound will hybridize to its target sequence, but to a minimal number of other sequences. Stringent conditions are sequence-dependent and will be different in different circumstances and as described herein. "Stringent conditions" under which oligomeric compounds hybridize to a target sequence are determined by the nature and composition of the oligomeric compounds and the assays in which they are being investigated.

As used herein, antisense compounds include antisense oligomeric compounds, antisense oligonucleotides, siRNAs, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds may elicit the action of one or more enzymes or structural proteins to effect modulation of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H.

Activation of RNAse H, therefore, results in cleavage of the RNA target, thereby greatly enhancing the efficiency of oligonucleotide-mediated inhibition of gene expression. Similar roles have been postulated for other ribonucleases such as those in the RNAse III and ribonuclease L family of enzymes.

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Gerlach et al., Nature 328, 802-805, 1987; Forster and Symons, Cell, 49, 211-20, 1987). For example, a large number of ribozymes accelerate phosphoester transfer reactions with a high degree of specificity, often cleaving only one of several phosphoesters in an oligonucleotide substrate (Michel and Westhof, J Mol. Biol. 216, 585-610, 1990; Reinhold-Hurek and Shub, Nature, 357, 173-6, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, Gene, 82, 83-7, 1989). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., Proc Natl Acad Sci USA. 88, 10591-5, 1991; Sarver et al., Science 247, 1222-5, 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

While one form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, Caenorhabditis elegans (Guo and Kempheus, Cell, 1995, 81, 611 620). Montgomery et al. have shown that the primary interference effects of dsRNA are posttranscriptional (Montgomery et al., Proc. Natl. Acad. Sci. USA, 1998, 95, 15502 15507). The posttranscriptional antisense mechanism defined in Caenorhabditis elegans resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., Nature, 1998, 391, 806 811). Activation of these mechanisms targets mature, dsRNA-complementary mRNA for destruction. Recently, it has been shown that it is, in fact, the single-stranded RNA oligomers of antisense polarity of the dsRNAs which are the potent inducers of RNAi (Tijsterman et al., Science, 2002, 295, 694 697). The use of these double stranded RNA molecules (short interfering RNA or siRNA) for targeting and inhibiting the expression of BBB protein mRNA is also contemplated. These double stranded RNA molecules target regions similar to those targeted by antisense oligonucleotides and have similar effects. These double stranded RNA molecules are generally 19-21 base pairs in length, but may range between 8 and 50 nucleobases.

RNAi offers experimental advantages for study of gene function. These advantages include a very high specificity, ease of movement across cell membranes, and prolonged down-regulation of the targeted gene (Fire et al., Nature, 1998, 391, 806-811; Grishok et al., Science 2000, 287, 2494-7; Ketting et al., Cell, 1999, 99, 133-41; Lin and Avery et al., Nature, 1999, 402, 128-9; Montgomery et al., Proc. Natl. Acad. Sci. USA, 1998, 95, 15502-15507; Sharp and Zamore, Science, 2000, 287, 2431-3). It is generally accepted that RNAi acts post-transcriptionally, targeting RNA transcripts for degradation. It appears that both nuclear and cytoplasmic RNA can be targeted (Bosher and Labouesse, Nat Cell Biol., 2000 2, E31-6).

siRNAs must be designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., Proc. Natl. Acad. Sci. USA, 1998, 95, 15502-15507).

The making of siRNAs has been mainly through direct chemical synthesis; through processing of longer, double stranded RNAs through exposure to *Drosophila* embryo lysates; or through an in vitro system derived from S2 cells. Use of cell lysates or in vitro processing may further involve the subsequent isolation of the short, 21-23 nucleotide siRNAs from the lysate, etc., making the process somewhat cumbersome and expensive. Chemical synthesis proceeds by making two single-stranded RNA-oligomers followed by the annealing of the two single stranded oligomers into a double-stranded RNA. Methods of chemical synthesis are diverse. Non-limiting examples are provided in U.S. Pat. Nos. 5,889, 136, 4,415,723, and 4,458,066, expressly incorporated herein by reference, and in Wincott et al. (Nucleic Acids Res. 1995 23, 2677-84).

Several further modifications to siRNA sequences have been suggested in order to alter their stability or improve their effectiveness. It is suggested that synthetic complementary 21-mer RNAs having di-nucleotide overhangs (i.e., 19 complementary nucleotides +3' non-complementary dimers) may provide the greatest level of suppression. These protocols primarily use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

Chemically synthesized siRNAs are found to work optimally when they are in cell culture at concentrations of 25-100 nM, but concentrations of about 100 nM have achieved effective suppression of expression in mammalian cells. siRNAs have been effective in mammalian cell culture at about 100 nM. In several instances, however, lower concentrations of chemically synthesized siRNA have been used (Caplen, et al., Gene, 2000, 252, 95-105; Elbashir et al., Nature, 2001, 411, 494-498; Genes Dev. 2001, 15, 188-200).

WO 99/32619 and WO 01/68836 suggest that RNA for use in siRNA may be chemically or enzymatically synthesized. Both of these texts are incorporated herein in their entirety by reference. The enzymatic synthesis contemplated in these references is by a cellular RNA polymerase or a bacteriophage RNA polymerase (e.g., T3, T7, SP6) via the use and production of an expression construct as is known in the art. For example, see U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25mer lengths with the endogenous nuclease complex that converts long dsRNAs to siRNAs in vivo. They do not describe or present data for synthesizing and using in vitro transcribed 21-25mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Preferably, single-stranded RNA is enzymatically synthesized from the PCR products of a DNA template, preferably a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates are preferably attached to a solid surface. After transcription with RNA polymerase, the resulting dsRNA fragments may be used for detecting and/or assaying nucleic acid target sequences.

The production of siRNA molecules is described in a general sense in the examples provided below, but it will be appreciated that any desired siRNA targeted to BBB proteins may be synthesized by conventional oligonucleotide synthesis techniques. Once the sequence of the antisense strand is known, the complementary sense strand is synthesized based on base pairing. The sense and antisense strands are then combined to form the siRNA.

The antisense compounds also include modified compounds in which a different base is present at one or more of the nucleotide positions in the compound. For example, if the first nucleotide is an adenosine, modified compounds may be produced which contain thymidine, guanosine or cytidine at this position. This may be done at any of the positions of the antisense compound. These compounds are then tested using the methods described herein to determine their ability to modulate expression of one or more BBB protein.

While oligonucleotides comprise one form of antisense compound, other families of antisense compounds are contemplated as well, including but not limited to oligonucleotide analogs and mimetics such as those described herein. One having skill in the art armed with the antisense compounds illustrated herein will be able, without undue experimentation, to identify further antisense compounds.

In certain aspects of the invention, antibodies may find use as modulators of beta-F1 ATPase expression/function. As used herein, the term "antibody" is intended to refer broadly to any appropriate binding agent such as IgG, IgM, IgA, IgD and IgE. Generally, IgG and/or IgM are the most common antibodies in the physiological situation and are most easily made in a laboratory setting.

The term "antibody" also refers to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art.

Monoclonal antibodies (MAbs) are recognized to have certain advantages, e.g., reproducibility and large-scale production, and their use is generally accepted. The invention thus provides monoclonal antibodies of the human, murine, monkey, rat, hamster, rabbit and even chicken origin. Due to the ease of preparation and ready availability of reagents, murine monoclonal antibodies will often be useful therapeutically and for proof of concept.

Single-chain antibodies are described in U.S. Pat. Nos. 4,946,778 and 5,888,773, each of which are hereby incorporated by reference.

"Humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's dental disease are likewise known and such custom-tailored antibodies are also contemplated.

"Targeting" an antisense compound to a particular nucleic acid molecule can be a multistep process. The process usually begins with the identification of a target nucleic acid whose function is to be modulated. This target nucleic acid may be, for example, a cellular gene (or mRNA transcribed from the gene) whose expression is associated with a particular central nervous system disorder, disease state, or injury, or a nucleic acid molecule from an infectious agent. In the present invention, the target is a nucleic acid encoding a BBB protein; in other words, a gene encoding a BBB protein, or mRNA expressed from a BBB protein gene. Messenger RNA which encodes the BBB protein beta-F1 ATPase is presently the target. While the identity of certain targets nucleic acids are set forth herein, one of skill in the art will recognize that these serve only to illustrate and describe particular embodiments. Additional target nucleic acids may be identified by one having ordinary skill. The targeting process also includes determination of a region or regions within the nucleic acid sequence for the antisense interaction to occur such that modulation of gene expression will result. While the specific sequences of certain target regions are set forth herein, one of skill in the art will also recognize that these serve only to illustrate and describe particular embodiments. Additional target regions may be identified by one having ordinary skill in the art.

As used herein, the term "region" is defined as a portion of the target nucleic acid having at least one identifiable structure, function, or characteristic. Within regions of target nucleic acids are segments. "Segments" are defined as smaller or sub-portions of regions within a target nucleic acid.

The translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. As used herein, "start codon" and "translation initiation codon" refer to the codon or codons that are used in vivo to initiate translation of an mRNA transcribed from a gene encoding a BBB protein, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds described herein.

The open reading frame (ORF) or "coding region," which is known in the art to refer to the region between the translation initiation codon and the translation termination codon, is also a region which may be targeted effectively. A region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions may also be particularly useful in situations where aberrant splicing is implicated in disease, or where an overproduction of a particular splice product is implicated in disease. Aberrant fusion junctions due to rearrangements or deletions are also target sites. Messenger RNA transcripts produced via the process of splicing of two (or more) mRNAs from different gene sources are known as "fusion transcripts". It is also known that introns can be effectively targeted using antisense compounds targeted to, for example, DNA or pre-mRNA.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. The types of variants described herein are also target nucleic acids.

Once the target region or regions have been identified, oligonucleotides are chosen which are sufficiently complementary to the target, i.e., hybridize sufficiently well and with sufficient specificity, to give the desired modulation. Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein or proteins to the RNA may also be interfered with by antisense oligonucleotide hybridization to the RNA.

An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complimentarily to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

The locations on the target nucleic acid to which the antisense compounds hybridize are herein below referred to as "target segments." As used herein the term "target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain target segments are set forth herein, one of skill in the art will recognize that these serve only to illustrate and describe particular embodiments. Additional target segments may be identified by one having ordinary skill. Once one or more target regions, segments or sites have been identified, antisense compounds are chosen which are sufficiently complementary to the target, i.e., hybridize sufficiently well and with sufficient specificity, to give the desired effect.

In a further embodiment, the "target segments" identified herein may be employed in a screen for additional compounds that modulate the expression of BBB proteins. "Modulators" are those compounds that decrease or increase the expression of a nucleic acid molecule encoding a BBB protein, or the function of a BBB protein. When the modulator is a modulator of nucleic acid expression, the screening method comprises the steps of contacting a target segment of a nucleic acid molecule encoding a BBB protein with one or more candidate modulators, and selecting for one or more candidate modulators which decrease or increase the expression of a nucleic acid molecule encoding the BBB protein. Once it is shown that the candidate modulator or modulators are capable of modulating (e.g. either decreasing or increasing) the expression of a nucleic acid molecule encoding a BBB protein, the modulator may then be employed in further investigative studies of the function of the BBB protein. The target segments may be also be combined with their respective complementary antisense compounds to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et at., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The antisense compounds can also be applied in the areas of drug discovery and target validation. The use of the compounds and target segments identified herein in drug discovery efforts to elucidate relationships that exist between a BBB protein and a disease state, phenotype, or condition is also contemplated. These methods include detecting or modulating one or more BBB proteins comprising contacting a sample, tissue, cell, or organism with the compounds described herein, measuring the nucleic acid or protein level of a BBB protein and/or a related phenotypic or chemical endpoint at some time after treatment, and optionally comparing the measured value to a non-treated sample or sample treated with a further compound. These methods can also be performed in parallel or in combination with other experiments to determine the function of unknown genes for the process of target validation or to determine the validity of a particular gene product as a target for treatment or prevention of a particular disease, condition, or phenotype.

The compounds of the present invention can be utilized for diagnostics, therapeutics, prophylaxis and as research reagents and kits. For example, the specific hybridization exhibited by the oligonucleotides may be used for assays, purifications, cellular product preparations and in other methodologies which would be appreciated by persons of ordinary skill in the art. Furthermore, compounds able to inhibit gene expression with exquisite specificity are often used by those of ordinary skill to elucidate the function of particular genes or to distinguish between functions of various members of a biological pathway.

For use in kits and diagnostics, the compounds described herein, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

The antisense compounds described herein are useful for research and diagnostics, because these compounds hybridize to nucleic acids encoding BBB proteins. For example, oligonucleotides that are shown to hybridize with such specificity and under such conditions as disclosed herein as to be effective beta-F1 ATPase inhibitors will also be effective primers or probes under conditions favoring gene amplification or detection, respectively. Primers and probes are useful in methods requiring the specific detection of nucleic acid molecules encoding BBB proteins and in the amplification of said nucleic acid molecules for detection or for use in further studies of BBB proteins. Hybridization of the antisense oligonucleotides, particularly the primers and probes described herein, with a nucleic acid encoding and BBB protein can be detected by means known in the art. Such means may include conjugation of an enzyme to the oligonucleotide, radiolabeling of the oligonucleotide or any other suitable detection means. Kits using such detection means for detecting the level of BBB proteins in a sample may also be prepared.

The present invention is also suitable for detection of overexpression of a BBB protein in tissue or other samples from a patient. A number of assays may be formulated employing the present invention, which assays will commonly comprise contacting a tissue sample with an oligonucleotide of the invention under conditions selected to permit detection, and usually quantitation, of such detection. For example, radiolabeled oligonucleotides can be prepared by 32P labeling at the 5' end with polynucleotide kinase. (Sambrook et al., Molecular Cloning. A Laboratory Manual, Cold Spring Harbor Laboratory Press, 1989, Volume 2, pg. 10.59). Radiolabeled oligonucleotides are then contacted with tissue or cell samples or with RNA extracted from such samples. The sample is then washed to remove unbound oligonucleotide. Radioactivity remaining in the sample indicates bound oligonucleotide (which in turn indicates expression of the nucleic acids encoding a specific BBB protein) and can be quantitated using a scintillation counter or other routine means. Comparison to appropriate controls allows overexpression of a BBB protein to be determined. Radiolabeled oligonucleotide can also be used to perform autoradiography of tissues to determine the localization, distribution and quantitation of BBB protein overexpression for research, diagnostic and therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing a specific BBB protein. Quantitation of the silver grains permits BBB protein overexpression to be detected.

Analogous assays for fluorescent detection of BBB protein expression can be developed using oligonucleotides of the invention which are conjugated with fluorescein or other fluorescent tag instead of radiolabeling. Such conjugations are routinely accomplished during solid phase synthesis using fluorescently-labeled amidites or CPG (e.g., fluorescein-labeled amidites or CPG available from Glen Research, Sterling, Va. See 1993 Catalog of Products for DNA Research, Glen Research, Sterling, Va., pg. 21).

Expression of BBB proteins may also be measured in serum, adipose tissue, liver or any other body fluid, tissue or organ of the animal. Preferably, the cells contained within said fluids, tissues or organs being analyzed contain a nucleic acid molecule encoding a BBB protein and/or the BBB protein itself.

Each of these assay formats is known in the art. One of skill could easily adapt these known assays for detection of BBB protein expression in accordance with the teachings of the invention providing a novel and useful means to detect BBB protein expression.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or injury of the central nervous system is treated by administering a compound that modulates one or more BBB proteins in accordance with this invention. For example, in one non-limiting embodiment, the methods comprise the step of administering to the animal in need of treatment, a BBB protein inhibitor. The BBB protein inhibitor effectively inhibits the activity of the BBB protein or inhibits the expression of the BBB protein. By inhibiting the BBB protein certain drugs will not enter the CNS thereby limiting the effect that drug might have on the CNS. In other cases inhibiting the BBB protein will increase the consecration of a drug in the CNS thereby increasing the activity of the drug in the CNS or allowing for the dose of the drug to be lowered.

In another embodiment, the present invention employs oligonucleotides for use in antisense inhibition of the function of RNA and DNA encoding one or more BBB proteins. In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often used in place of native forms because of desirable properties such as, for example, enhanced cellular uptake, enhanced affinity for nucleic acid target and increased stability in the presence of nucleases. A discussion of antisense oligonucleotides and some desirable modifications can be found in De Mesmaeker et al., Acc. Chem. Res. 1995, 28, 366-374.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; however, the actual synthesis of the oligonucleotides is well within that known in the art. It is also known to use similar techniques to prepare other oligonucleotides such as the phosphorothioates and alkylated derivatives.

A nucleoside is a base-sugar combination. The base portion of the nucleoside is normally a heterocyclic base sometimes referred to as a "nucleobase" or simply a "base". The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are more common. In addition, linear compounds may have internal nucleobase complimentarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Specific examples of antisense compounds include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Modified oligonucleotide backbones containing a phosphorus atom therein include, for example, phosphorothioates, chiral phosphorothioates, phosphorodithioates, phosphotriesters, aminoalkylphosphotriaminoalkylphospho-triesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3' 5' linkages, 2' 5' linked analogs of these, and those having inverted polarity wherein one or more internucleotide linkages is a 3' to 3', 5' to 5' or 2' to 2' linkage.

Oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Other antisense compounds, e.g., oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497 1500.

Some embodiments are oligonucleotides with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—N($CH_3$)—$CH_2$—, —$CH_2$—N($CH_3$)—N($CH_3$) $H_2$— and —O—N($CH_3$)—$CH_2$—$CH_2$— [wherein the native phosphodiester backbone is represented as —O—P—$CH_2$—] of the above referenced U.S. Pat. No. 5,489,677, and the amide backbones of the above referenced U.S. Pat. No. 5,602,240. Also provided are oligonucleotides having morpholino backbone structures of the above-referenced U.S. Pat. No. 5,034,506.

Modified Sugars

Modified antisense compounds may also contain one or more substituted sugar moieties. antisense compounds, like oligonucleotides, comprising one of the following at the 2' position: OH; F; O-, S-, or N-alkyl; O-, S-, or N-alkenyl; O—, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486 504) i.e., an alkoxyalkoxy group. A further modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples herein below.

Other modifications include 2'-methoxy (2'-O—$CH_3$), 2'-aminopropoxy (2'-O$CH_2CH_2CH_2NH_2$), 2'-allyl (2'-$CH_2$CH=$CH_2$), 2'-O-allyl (2'-O—$CH_2$—CH=$CH_2$) and 2'-fluoro (2'-F). 2'-modification may be in the arabino (up) position or ribo (down) position. A 2'-arabino modification is 2'-F. Similar modifications may also be made at other positions on the oligonucleotide, particularly the 3' position of the sugar on the 3' terminal nucleotide or in 2' 5' linked oligonucleotides and the 5' position of 5' terminal nucleotide. Antisense compounds may also have sugar mimetics such as cyclobutyl moieties in place of the pentofuranosyl sugar. United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811;

5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

A further modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene ($-CH_2-$)$_n$ group bridging the 2' oxygen atom and the 4' carbon atom wherein n is 1 or 2. LNAs and preparation thereof are described in WO 98/39352 and WO 99/14226.

Antisense compounds may also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido [5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the compounds described herein. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2 degrees C. and are presently base substitutions, even more particularly when combined with 2'-O-methoxyethyl sugar modifications.

United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, 5,750,692, each of which is herein incorporated by reference.

Conjugates

Another modification of the antisense compounds involves chemically linking to the antisense compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of the compounds described herein. Examples of conjugate groups are disclosed in International Patent Application PCT/US92/09196, filed Oct. 23, 1992, and U.S. Pat. No. 6,287,860, the entire disclosures of which are incorporated herein by reference. Conjugate moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Antisense compounds may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide.

Other embodiments also include antisense compounds which are chimeric compounds. "Chimeric" antisense compounds or "chimeras" are antisense compounds, particularly oligonucleotides, which contain two or more chemically distinct regions, each made up of at least one monomer unit, i.e., a nucleotide in the case of an oligonucleotide compound. Chimeric antisense oligonucleotides are thus a form of antisense compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNAse H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAse L which cleaves both cellular and viral RNA. Cleavage of the RNA target can be routinely detected by gel electrophoresis and, if necessary, associated nucleic acid hybridization techniques known in the art.

Chimeric antisense compounds may be formed as composite structures of two or more oligonucleotides, modified oligonucleotides, oligonucleosides and/or oligonucleotide mimetics as described above. Such compounds have also been referred to in the art as hybrids or gapmers. United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The compounds described herein may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds described herein: i.e., salts that retain the desired biological activity of the parent compound and do not impart undesired toxicological effects thereto. For oligonucleotides, examples of pharmaceutically acceptable salts and their uses are further described in U.S. Pat. No. 6,287,860, which is incorporated herein in its entirety.

Another embodiment is pharmaceutical compositions and formulations which include the antisense compounds described herein. The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions may be formulated into any of many possible dosage forms such as, but not limited to, tablets, capsules, gel capsules, liquid syrups, soft gels, suppositories, and enemas. The compositions may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions include, but are not limited to, solutions, emulsions, foams and liposome-containing formulations. The pharmaceutical compositions and formulations may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are also contemplated. Emulsions and their uses are well known in the art and are further described in U.S. Pat. No. 6,287,860, which is incorporated herein in its entirety.

Formulations include liposomal formulations. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions may also include surfactants. The use of surfactants in drug products, formulations and in emulsions is well known in the art. Surfactants and their uses are further described in U.S. Pat. No. 6,287,860, which is incorporated herein in its entirety.

In one embodiment, various penetration enhancers are employed to affect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Formulations for topical administration include those in which the oligonucleotides are in admixture with a topical delivery agent such as lipids, liposomes, fatty acids, fatty acid esters, steroids, chelating agents and surfactants. Lipids and liposomes include those that are neutral (e.g. dioleoylphosphatidyl DOPE ethanolamine, dimyristoylphosphatidyl choline DMPC, distearoylphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides may be encapsulated within liposomes or may form complexes thereto, in particular to cationic liposomes. Alternatively, oligonucleotides may be complexed to lipids, in particular to cationic lipids. Fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Oral formulations are those in which oligonucleotides are administered in conjunction with one or more penetration enhancers, surfactants, and/or chelators. Surfactants include fatty acids and/or esters or salts thereof, bile acids and/or salts thereof. Bile acids/salts and fatty acids and their uses are further described in U.S. Pat. No. 6,287,860, which is incorporated herein in its entirety. Also provided are combinations of penetration enhancers, for example, fatty acids/salts in combination with bile acids/salts. A particularly combination is the sodium salt of lauric acid, capric acid and UDCA. Further penetration enhancers include polyoxyethylene-9-lauryl ether, polyoxyethylene-20-cetyl ether. Oligonucleotides may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. No. 09/108,673 (filed Jul. 1, 1998), Ser. No. 09/315,298 (filed May 20, 1999) and Ser. No. 10/071,822, filed Feb. 8, 2002, each of which is incorporated herein by reference in its entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

In another related embodiment, the compositions may contain one or more antisense compounds, particularly oligonucleotides, targeted to a first nucleic acid and one or more additional antisense compounds targeted to a second nucleic acid target. Alternatively, compositions may contain two or more antisense compounds targeted to different regions of the same nucleic acid target. Numerous examples of antisense compounds are known in the art. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state.

Identification of Beta-F1 ATPase as a BBB Transporter of PACAP and its Modulation Like many peptides, PACAP is pluripotent and has binding sites located throughout the CNS, but whose delivery to brain is complicated by the BBB. PACAP has a particularly complex relation with the BBB. The PACAP38 form is transported into brain and both the PACAP38 and PACAP27 forms are transported out of brain. This transporter activity at the BBB has been reified as PTS-6. Pharmacokinetic studies have suggested that PTS-6 is likely a family of transporters with one member transporting PACAP38 into brain and at least one other member transporting PACAP38 and PACAP27 in the brain-to-blood direction. Alternatively, a single transporter might exist which has different affinities for PACAP38 and PACAP27 depending on whether binding is occurring at the luminal (blood-side) or abluminal (brain-side) surface of the brain endothelial cell. Finally, a combination of these two possibilities could exit: multiple transporters but with overlapping affinities. Here, PACAP27 was used as a probe, thus increasing the chances of only detecting the efflux transporter.

I-PACAP27 is able to specifically bind to mouse brain microvessels by a saturable mechanism. This supports the conjecture that a site of transport of PACAP is at the vascular BBB, although it does not rule out the choroid plexus as an additional site where PACAP may also be transported. The binding of I-PACAP27 was time and temperature dependent and saturable with maximal specific binding occurring at 20 min. Binding was inhibited competitively above 30 ng of unlabeled PACAP27. The results for $B_{max}$ and $K_d$ show that PACAP27 binds at a single high affinity site. This is rather surprising as other work has suggested that the brain endothelial cell may also possess a binding site for PACAP unrelated to transport (Morley et al., Peptides 23, 589-599, 2002; Nonaka, et al., Exp. Neurol. 191, 137-144, 2005). It may be that the receptor is much less abundant and so was not detected under the conditions of this experiment.

Two classes of PACAP binding sites have been characterized in other tissues (Shioda, 2000; Rodriguez-Henche et al., Biochim. Biophys. Acta 1221, 193-198 1994; Salomon et al., Am J Physiology 264, E294-E300, 1993; Salano et al., Endocrinology 137, 2815-2822, 1996). Type-I binding sites characterized in the anterior pituitary and hypothalamus using I-PACAP27 as a radioligand exhibit a high affinity for PACAP38 and PACAP27 with a $K_d$ about 0.5 nM and a much lower affinity for VIP about $K_d>500$ nM. Based on displacement of I-PACAP27 binding, the receptor has a higher affinity for PACAP38 than for PACAP27. Type-II binding sites are abundant in various peripheral organs including the lung, duodenum, and thymus, and possess similar affinities for PACAP and VIP[5]. It has been reported that VIP and PACAP share a common receptor in human peripheral tissues such as prostate, liver, and small intestine as it does not discriminate among VIP, PACAP27, and PACAP38 (Knutsson and Edvinsson, Neuroreport 13, 507-509, 2002); Rodriguez-Henche et al., 1994; Salomon et al., 1993; Salano et al., 1996). Here, it was found that VIP did not inhibit binding of PACAP27 to brain endothelial cells. This ruled out the possibility that either of the two VPAC receptors could account for binding to brain endothelial cells. The relative ranking among the inhibitors used (FIG. 3) also raised questions about whether binding was to the type-I receptor. In total, these results indicated that the binding protein for I-PACAP27 at brain endothelial cells was not any of the known PACAP receptors.

Identification of the PACAP27 binding protein by mass spectrophotometry confirmed that it was not one of the previously identified receptors for PACAP. The identified protein, beta-F1 ATPase, co-localized with PACAP immunoactivity on freshly isolated brain endothelial cells. Beta-F1 ATPase has been shown to act as either a binding protein or a transporter in other tissues for a number of other ligands unrelated to PACAP. In other words, its function varies depending on the site in which it is expressed. Originally identified as an extra-membrane component of ATPase in mitochondria (ATP synthase beta subunit), it was subsequently found to be identical to the apolipoprotein A-1 receptor that transports high density lipoproteins at hepatocytes (Martinez et al., Nature 421, 75-79, 2003). It has also been found to be expressed by a number of other tissues, including neurons, where it acts as the receptor to enterostatin, a pentapeptide unrelated structurally to PACAP and involved in feeding (Park et al., Peptides 25, 2127-2133, 2004). Cultured brain endothelial cells, but not aortic endothelial cells, express and secrete this protein and expression is increased by cholesterol, insulin, and retinoic acid (Weiler-Guttler et al., J. Neurochem. 54, 444-450, 1990; Mockel et al., J. of Neurochem. 62, 788-798, 1994). However, the function of beta-F1 ATPase in brain endothelial cells was unknown. Interestingly, two other lipoprotein binding molecules have been found to act as efflux transporters for peptides. P-glycoprotein is a member of the ATP-binding cassette family, binds Apo A-1 and transports some of the small opiate peptides and the immunosuppressant peptide cyclosporin in the brain-to-blood direction (Begley, Current Pharmaceutical Design 10, 1295-1312, 2004). LDL receptor-related protein-1 acts as an efflux transporter for amyloid β protein (Deane et al., Neuron 43, 333-344, 2004).

Inhibition of an efflux system for a peptide would be expected to selectively increase the levels of the peptide in the brain after either the peripheral or central administration of the peptide. It is presently shown that both of these events happened in mice treated with a cocktail of antisenses directed against beta-F1 ATPase. A single injection of the cocktail mixture inhibited transport that lasted about 48 h. Efflux systems for iodide, the tetrapeptide Tyr-MIF-1, and opiate peptide β-endorphin were not affected. Lack of an effect shows that the antisense did not affect the activities of the inorganic ion efflux system, PTS-1, or P-glycoprotein (Davson and Hollingsworth, J. Physiol. (London) 233, 327-347, 1973); Banks and Kastin, Am. J. Physiol. 259, E1-E10, 1990; King et al., Nature Neuroscience 4, 221-222, 2001). Similarly, the antisense cocktail to beta-F1 ATPase increased brain uptake of intravenously administered PACAP27 whereas other antisenses were ineffective. These studies also showed that I-PACAP38 influx or efflux was not affected by the antisense cocktail, showing that beta-F1 ATPase acts as an efflux pump for PACAP27, but does not function as either the influx or efflux transporter for PACAP38. This is consistent with previous work showing that PACAP27 efflux was insensitive to LHRH, whereas PACAP38 efflux was LHRH sensitive. This previous work showing that PACAP38, but not PACAP27, efflux was sensitive to LHRH suggested that two different transporters, one LHRH sensitive and one LHRH-insensitive, handled these two peptides. The inability of beta-F1 ATPase to inhibit PACAP38 efflux while inhibiting PACAP27 efflux confirms that two separate efflux systems exist for these peptides.

ATPases (or ATP synthases) are membrane-bound enzyme complexes/ion transporters that combine ATP synthesis and/or hydrolysis with the transport of protons across a membrane. ATPases can harness the energy from a proton gradient, using the flux of ions across the membrane via the ATPase proton channel to drive the synthesis of ATP. Some ATPases work in reverse, using the energy from the hydrolysis of ATP to create a proton gradient. There are different types of ATPases, which can differ in function (ATP synthesis and/or hydrolysis), structure (F-, V- and A-ATPases contain rotary motors) and in the type of ions they transport.

The F1, V1, and A1 complexes of F-, V- and A-ATPases, respectively (sometimes called the A and B subunits in V- and A-ATPases), each contain α and β subunits. The F-ATPases (or F1F0-ATPases), V-ATPases (or V1V0-ATPases) and A-ATPases (or A1A0-ATPases) are composed of two linked complexes: the F1, V1 or A1 complex contains the catalytic core that synthesizes/hydrolyses ATP, and the F0, V0 or A0 complex that forms the membrane-spanning pore. The F-, V- and A-ATPases all contain rotary motors, one that drives proton translocation across the membrane and one that drives ATP synthesis/hydrolysis.

In F-ATPases, there are three copies each of the α and β subunits that form the catalytic core of the F1 complex, while the remaining F1 subunits (γ, δ and ε) form part of the stalks. There is a substrate-binding site on each of the α and β subunits, those on the β subunits being catalytic, while those on the α subunits are regulatory. The α and β subunits form a cylinder that is attached to the central stalk. The α/β subunits undergo a sequence of conformational changes leading to the formation of ATP from ADP, which are induced by the rotation of the γ subunit, itself being driven by the movement of protons through the F0 complex C subunit.

The α/A and β/B subunits can each be divided into three regions, or domains, centered around the ATP-binding pocket, and based on structure and function, where the central region is the nucleotide-binding domain. This entry represents the C-terminal domain of the α/A /β/B subunits, which forms a left-handed superhelix composed of 4-5 individual helices. The C-terminal domain can vary between the α and β subunits, and between different ATPases.

The accession number for beta-F1 ATPase is X03559 and was first reported by Ohta and Kagawa J. Biochem. 99, 135-41 (1986) (incorporated herein by reference).'

One aspect of the present invention contemplates inhibitors of beta-F1 ATPase expression and/or function. As used herein to describe the regulatory effect that a compound has on the expression of a gene, the term "inhibition" means that the compound reduces the expression of one or more genes to some degree compared with its expression under the same conditions, but without the presence of the compound. Inhibitory compounds commonly demonstrate concentration dependant activity, wherein increased concentrations of such compounds demonstrate higher levels of inhibition. When the terms "inhibitory effective amount" are used herein with respect to an inhibitory compound, what is meant is an amount of an inhibitory compound that inhibits the expression or activity of a gene to a measurable degree. Such inhibitory effective amount may reduce the level of expression/activity by at least about 25%; at least about 50%; at least about 75%; and at least about 80%, or more.

PACAP27 is a core subregion of PACAP that stimulates adenylate cyclase to a greater extent than does vasoactive intestinal peptide (VIP). VIP and PACAP belong to the largest family of regulatory peptides, which comprises several other prominent neuroendocrine peptides including secretin (the first peptide hormone that has been identified), glucagon, and growth hormone-releasing hormone. The primary structures of VIP and PACAP are conserved across vertebrates, suggesting that these peptides have important functions. Indeed, VIP and PACAP appear to be implicated in a large array of physiological processes such as development; growth; endocrine, cardiovascular, respiratory, reproductive and digestive functions; immune responses; and circadian rhythms. The beneficial influence of VIP and PACAP agonists and antagonists in various pathological states including heart failure, ischemia, asthma, impotence, and cancer has motivated the development of novel selective VIP or PACAP ligands, such as PACAP 27, that can be used as antihypertensive, neuroprotective, bronchodilatory, vasodilatory, and/or antiproliferative drugs. Potential PACAP 27 therapies include treatment of central nervous system injury or disorders, such as neuroAIDS complex, Alzheimer's disease, Parkinson's disease or ischemic brain injury.

Another aspect of the present invention is the use of an inhibitor of beta-F1 ATPase in combination with PACAP therapeutics. Thus, one may provide to the patient a PACAP therapy in combination with an inhibitor of beta-F1 ATPase. Combinations may be achieved by administration of a single composition or pharmacological formulation that includes both agents, or by contacting the cell with two distinct compositions or formulations, at the same time. Alternatively, the therapy using an inhibitor may precede or follow administration of the PACAP agent(s) by intervals ranging from minutes to weeks. In embodiments where the inhibitor and PACAP are applied separately, one would generally ensure that a significant period of time did not expire between the times of each delivery, such that the inhibitor could retain activity at a time when the PACAP reaches the target tissue. In such instances, it is contemplated that one would typically administer both modalities within about 12-24 hours of each other and, more preferably, within about 6-12 hours of each other.

It also is conceivable that more than one administration of either an inhibitor or the PACAP will be desired. In this regard, various combinations may be employed. By way of illustration, where the inhibitor is "A" and the PACAP is "B," the following permutations based on 3 and 4 total administrations are exemplary: A/B/A B/A/B B/B/A A/A/B B/A/A A/B/B B/B/B/A B/B/A/B A/A/B/B A/B/A/B A/B/B/A B/B/ A/A B/A/B/A B/A/A/B B/B/A/A A/A/A/B B/A/A/A A/B/ A/A A/A/B/A A/B/B/B B/A/B/B B/B/A/B Other combinations are likewise contemplated.

Modulation of BBB transporter LRP-1 and its Effect on Aβ and
Physiological Activity Alzheimer's disease (AD) is the most common cause of dementia among people over the age of 65 Hebert, et al., Arch Neurol 60, 1119-1122, 2003). It is a progressive disease characterized by extensive cortical and hippocampal neurodegeneration. The clinical symptoms of AD positively correlate with the degree of neuronal loss, therefore, early indications of AD pathology are short term memory loss and mild confusion, while later AD is associated with severe disability. On a microscopic level, the AD brain is distinguished by the presence of amyloid plaques. Plaques are insoluble extracellular deposits that contain a variety of aggregated molecules with the main component being amyloid beta protein (Aβ) (Selkoe, Trends Cell Biol 8, 447-453, 1998).

Aβ is produced when the amyloid precursor protein (APP) is cleaved by the β- and γ-secretase enzymes. Because the cleavage site for γ-secretase is variable, Aβ can be between 39 to 43 amino acids. The most common Aβ isoform is 40 amino acids long ($A\beta_{40}$) (Selkoe, Rev Neurosci 17, 489-517,1994). The 42 amino acid isoform ($A\beta_{42}$), however, demonstrates a higher degree of neurotoxicity, a characteristic that may be due to its propensity to form soluble and insoluble aggregates (Gravina. et al. J Biol Chem 270, 7013-7016, 1995; Iwatsubo et al. Neuron 13, 45-53,1994; Jaeger & Banks, Front Biosci 9, 1720-1727, 2004). Previous studies have shown that deposits of Aβ in the brain parenchyma of AD patients consist of mainly $A\beta_{42}$, therefore, this isoform is thought to play a major role in AD pathology (Masters et al. Proc Natl Acad Sci USA 82, 4245-4249, 1985).

AD has a rare (<1% of all cases) autosomal dominant form (early onset or familial AD; FAD) that typically occurs by age 60. FAD is caused by inheritance of at least one of a series of missense mutations all of which can result in increased production of $A\beta_{42}$ (Bertram & Tanzi, Pharmacol Res 50, 385-396, 2004). Although most animal models of AD are based on FAD mutations (Hock & Lamb, Trends Genet. 17, S7-S12, 2001)., the majority of AD cases (>99%) occur sporadically after the age of 60 (late onset AD, LOAD). Unlike FAD, LOAD is not associated with overproduction of Aβ. It is, however, associated with the presence of plaques containing the $A\beta_{42}$ protein, suggesting that this type of AD could be caused by altered Aβ clearance. In the past, degradation by neprylisin, insulin-degrading enzyme and endothelin-converting enzyme was thought to be the primary mechanism for Aβ removal from the brain (Eckman, et al., J Biol Chem 278, 2081-2084, 2003). Recently, attention has shifted to the role of the blood-brain barrier (BBB) in brain clearance of Aβ. According to the neurovascular hypothesis of AD, dysfunction of brain endothelial cells of the BBB could directly contribute to AD(Zlokovic, Trends Neurosci 28, 202-208, 2005). Specifically, if BBB-mediated clearance of Aβ was impaired, this would result in its accumulation in the brain and eventual poisoning of the neuronal environment.

Previous research has indicated that the low density lipoprotein receptor-related protein-1 (LRP-1) functions as a BBB clearance (or efflux) transporter for Aβ. Animal models indicate that levels of LRP-1 may naturally decline with age. For example, immunocytochemistry of brain microvessels from young (2 months) and old (9 months) C57BL/6 wild-type mice revealed that there is a 42% reduction in LRP-1 positive vessels in aged mice (Shibata et al. J Clin Invest 106, 1489-1499, 2000). Furthermore, a post-mortem study of human AD patients indicates that LRP-1 levels are more closely associated with pathology. Specifically, researchers found that LRP-1 is approximately two-fold lower in AD brains compared to that of their age-matched controls (Kang et al. J Clin Invest 106, 1159-1166, 1998). Currently, no animal model exists for the study of the role of LRP-1 in AD because LRP-1 knock-out mice die at day 13.5 during embryonic development (Willnow, et al., Proc Natl Acad Sci USA 92, 4537-4541, 1995). In the present disclosure, antisense oligodeoxynucleotides were used to alter expression of LRP-1 in mice so that the neurovascular hypothesis could be directly tested in vivo. It is shown herein that dysfunction of LRP-1, a BBB efflux transporter for Aβ, can result in reduced brain efflux of $^{131}$I-AP$_{42}$, impaired learning ability in the T-maze, impaired recognition memory for a novel object, and increased brain levels of Aβ$_{42}$ in mice. The results are another demonstration that modulation of a BBB transporter by antisense technology leads to differential compound levels in the brain leading to the anticipated physiological effects.

Also anticipated is the modulation of P-glycoprotein expression, a protein known to exist in the BBB, using antisense oligonucleotides delivered into the periphery by means know in the art including but not limited to intraperitoneally, intravenously, intramuscular, and subcutaneous methods. King et al., (Nature Neuroscience 4, 268-274, 2001) demonstrated reduction of the rat P-glycoprotein expression in the brain using the oligonucleotide 5'-GGACTAAATGCTTTC-CTTTGTGACAG-3' (SEQ ID NO 16) via intracranial introduction of the oligonucleotide. It would be useful to identify identical sequences in the mouse and human for both murine disease model studies, safety studies and clinical treatment. However, there is not human and mouse oligonucleotide sequence that extensively matches the given rat sequence. The sense sequence of the preferred region of homology that exists among all three species is 5'-AGCATTTAGTC(or T)C (or T or A)A(or G)TTTT(or C)AGAGTCTTC-3'. This sequence serves as a template for the generation of antisense molecules, potential sense strands of which for the generation of antisense molecules are given as SEQ ID NOs 17-40.

In one aspect, the present invention provides a method of treating a disease or injury in a patient in need of such treatment, said method comprising administering to said patient an agent that inhibits a blood-brain barrier protein.

In further embodiments, said blood-brain barrier protein is a transporter protein.

In further embodiments, said blood-brain barrier protein is selected from the group consisting of P-glycoprotein, beta-F1 ATPase, low density lipoprotein receptor related protein-1 (LRP-1), organic ion pumps, peptide transporters, protein transporters, transporters for macronutrients, transporters for micronutrients, those involved in mechanisms for immune and stem cell transport, tight junction and vesicular related proteins, transporters which can transport drugs or therapeutics, and transporters involved in mechanisms that result in viral, pathogen, and toxin transport.

In further embodiments, said blood-brain barrier protein is beta-F1 ATPase.

In other embodiments, said blood-brain barrier protein is P-glycoprotein.

In other embodiments, said blood-brain barrier protein is low density lipoprotein receptor related protein-1 (LRP-1).

In further embodiments, said agent is selected from the group consisting of an antisense compound, a siRNA, a small molecule organopharmaceutical, a ribozyme, a mAb and a peptide.

In further embodiments, said agent is an antisense compound.

In certain embodiments, said antisense compound is selected from the group consisting of SEQ ID NO.s 1-5,7,8, and 10-15, or is an antisense molecule to any one of SEQ ID No.s 17-40.

In certain embodiments, said agent passes through the blood brain barrier of said patient.

In certain embodiments, said agent increases the central nervous system concentration of an endogenous central nervous system compound.

In certain embodiments, said agent increases the central nervous system concentration of said drug.

In certain embodiments, said agent decreases the efflux of said drug from the central nervous system of said patient.

In further embodiments, said disease or injury is of the central nervous system.

In further embodiments, said disease or injury is selected from the group consisting of neuroAIDS complex, Alzheimer' disease, Parkinson's disease, ischemic brain injury, traumatic brain injury, thrombotic stroke, hemorrhagic stroke, epilepsy, enzymatic deficiencies, and cancer.

In further embodiments, said disease or injury is ischemic brain injury, or traumatic brain injury.

In further embodiments, said drug is PACAP27.

In further embodiments, said disease is cancer.

In further embodiments, said drug is a chemotherapeutic drug.

In further embodiments, said drug is PACAP38.

In certain embodiments, the agent is administered in conjunction with a therapeutically effective amount of a therapeutic drug.

In further embodiments, the administration of said agent reduces the amount of said drug required to be therapeutically effective.

In further embodiments, the administration of said agent reduces the systemic side effects of said drug.

In certain embodiments, said agent is administered systemically, orally, nasally, intravenously, subcutaneously, intramuscularly, or by continuous infusion.

In further embodiments, said agent is administered nasally, intravenously, subcutaneously, or intramuscularly.

In another aspect, the present invention provides a method of treating a disease of the central nervous system of a patient in need thereof comprising administering to said patient an agent that inhibits a protein produced by the neural vascular unit.

In another aspect, the present invention provides a method of improving the efficacy of a therapeutic drug in a patient in need thereof, comprising administering said therapeutic drug in conjunction with an agent that inhibits a blood-brain barrier protein to said patient.

In certain embodiments, said blood-brain barrier protein is beta-F1 ATPase.

In other embodiments, said blood-brain barrier protein is P-glycoprotein.

In other embodiments, said blood-brain barrier protein is low density lipoprotein receptor related protein-1 (LRP-1).

In certain embodiments, said agent is selected from the group consisting of an antisense compound, a siRNA, a small molecule organopharmaceutical, a ribozyme, a mAb and a peptide.

In further embodiments, said agent is an antisense compound.

In other embodiments, said drug is selected from the group consisting of oncological agents and CNS-active agents.

In certain embodiments, wherein said drug is administered at sub cMax doses.

In further embodiments, said drug is PACAP27.

In further embodiments, said drug is PACAP38.

In another aspect, the present invention provides a method of increasing a therapeutic drug concentration in the central nervous system of a patient in need thereof comprising administering said therapeutic drug in conjunction with an agent that inhibits a blood-brain barrier protein.

In further embodiments, said blood-brain barrier protein is beta-F1 ATPase.

In other embodiments, said blood-brain barrier protein is P-glycoprotein.

In other embodiments, said blood-brain barrier protein is LRP-1.

In further embodiments, said agent is selected from the group consisting of an antisense compound, a siRNA, a small molecule organopharmaceutical, a ribozyme, a mAb and a peptide.

In further embodiments, said agent is an antisense compound.

In further embodiments, said drug is selected from the group consisting of oncological agents and CNS-active agents.

In certain embodiments, said drug is PACAP27.

In other embodiments, said drug is PACAP38.

In another aspect, the present invention provides a method of decreasing the efflux of a therapeutic drug from the central nervous system of a patient in need thereof comprising administering said therapeutic drug in conjunction with an agent that inhibits a blood-brain barrier protein.

In further embodiments, said blood-brain barrier protein is beta-F1 ATPase.

In other embodiments, said blood-brain barrier protein is P-glycoprotein.

In other embodiments, said blood-brain barrier protein is LRP-1.

In further embodiments, said agent is selected from the group consisting of an antisense compound, a siRNA, a small molecule organopharmaceutical, a ribozyme, a mAb and a peptide.

In further embodiments, said agent is an antisense compound.

In further embodiments, said drug is selected from the group consisting of oncological agents and CNS-active agents.

In further embodiments, said drug is PACAP27.

In further embodiments, said drug is PACAP38.

In another aspect, the present invention provides a method of reducing the systemic side effects of a drug administered to a patient, comprising administering said drug in conjunction with an agent that inhibits a blood-brain barrier protein.

In other embodiments, said blood-brain barrier protein is P-glycoprotein.

In further embodiments, said blood-brain barrier protein is beta-F1 ATPase.

In other embodiments, said blood-brain barrier protein is LRP-1.

In further embodiments, said agent is selected from the group consisting of an antisense compound, a siRNA, a small molecule organopharmaceutical, a ribozyme, a mAb and a peptide.

In further embodiments, said agent is an antisense compound.

In further embodiments, said drug is selected from the group consisting of oncological agents and CNS-active agents.

In further embodiments, said drug is PACAP27.

In further embodiments, said drug is PACAP38.

In another aspect, the present invention provides a method of modulating the transport of a drug out of the CNS of a patient in need thereof by inhibiting beta-F1 ATPase.

In another aspect, the present invention provides a method of modulating the transport of a drug out of the CNS of a patient in need thereof by inhibiting LRP-1.

In another aspect, the present invention provides a method of modulating the transport of a drug out of the CNS of a patient in need thereof by inhibiting P-glycoprotein.

In further embodiments, said inhibition is accomplished by administering an agent selected from the group consisting of an antisense compound, a siRNA, a small molecule organopharmaceutical, a ribozyme, a mAb and a peptide.

In further embodiments, said agent is an antisense compound.

In further embodiments, said drug is selected from the group consisting of oncological agents and CNS-active agents.

In further embodiments, said drug is PACAP27.

In further embodiments, said drug is PACAP38.

In another aspect, the present invention provides an antisense compound to a nucleic acid molecule encoding beta-F1 ATPase.

In further embodiments, the antisense molecule is 1-50 nucleobases in length and targeted to nucleobases of a nucleic acid molecule encoding a human beta-F1 ATPase.

In another aspect, the present invention provides an antisense compound to a nucleic acid molecule encoding human P-glycoprotein.

In further embodiments, the antisense molecule is 1-50 nucleobases in length and targeted to nucleobases of a nucleic acid molecule encoding a human P-glycoprotein.

In another aspect, the present invention provides an antisense compound to a nucleic acid molecule selected from the group consisting of SEQ ID NO.s 17-40.

In another aspect, the present invention provides an antisense compound to a nucleic acid molecule encoding human LRP-1.

In another aspect, the present invention provides a pharmaceutical composition comprising an antisense compound as provided herein and a pharmaceutically acceptable carrier or diluent.

In certain embodiments, the pharmaceutical composition further comprises a colloidal dispersion system.

In further embodiments, the antisense compound is an antisense oligonucleotide.

In certain embodiments, the pharmaceutical composition further comprises therapeutic drug.

In certain embodiments, the pharmaceutical composition further comprises PACAP27.

In certain embodiments, the pharmaceutical composition further comprises PACAP38.

In certain embodiments, the pharmaceutical composition further comprises chemotherapeutic agent for the treatment of cancer.

While embodiments have been discussed herein, the following examples are meant to be illustrative and not limiting. Each of the references, GenBank accession numbers, and the like recited in the present application is incorporated herein by reference in its entirety.

EXAMPLE 1

Identification and Modulation of the beta-F1 ATPase in the BBB

Materials and Methods

Radioactive Labeling. Iodination of 5.0 µg of PACAP27 (Bachem, Torrance, Calif.) with $^{131}$I was performed by the lactoperoxidase method. Iodinated PACAP27 (PACAP27) was purified on a C18 column by RP-HPLC. Incorporation of $^{131}$I as determined by acid precipitation was >95% and specific activity was about 1.82 mCi/mg.

Brain Microvessel Isolation. Cerebral microvessels were isolated from mice by a modification of a method described by Gerhart et al. (Brain Res. Bull. 21, 785-793, 1988). All reagent volumes were proportionally adjusted for the quantity of tissue processed and unless otherwise noted, all reagents were of cell culture quality from Sigma Chemical Company (St. Louis, Mo.). All glassware was precoated with lactated Ringer's solution containing 1% bovine serum albumin to minimize sticking and to maximize recovery of microvessels. Male CD-1 mice from our in-house colony weighing 25-40 g were anesthetized with urethane (0.5 g/kg) before decapitation. This and all other animal studies were done under protocols approved by the VA animal care and use committee, and in accordance with IACUC guidelines. For each microvessel isolation procedure, whole brains from 10 mice were dissected from surrounding structures, the pituitary and the pineal glands discarded, and the remainder placed in stock buffer (25 mM HEPES, 1% dextran in minimum essential medium (Gibco Laboratories, Grand Island, N.Y.) pH 7.4) on ice. The tissue was homogenized with 10 strokes in a glass tissue grinder with a teflon pestle. The homogenate was then filtered through a series of nylon mesh membranes (300 μm, followed by 2×100 μm; Spectrum Scientific Corp., Houston, Tex.), mixed with an equal volume of 40% dextran in stock buffer and centrifuged at 5000 g for 15 min at 4° C. The myelin layer was carefully removed. The pellet was resuspended in stock buffer and filtered through a 25 micron (μm) nylon mesh membrane (Bio-Design, Carmel, N.Y.). The microvessels were washed from the surface of the nylon mesh with stock buffer four times, collected, and centrifuged at 5000 g for 15 min at 4° C. The purity and quantity of each preparation was routinely checked by light microscopy.

Binding Study. Freshly isolated microvessels (30 μg protein) were resuspended in 45 μl of incubation buffer (129 mM NaCl, 2.5 mM KCl, 7.4 mM Na$_2$HPO$_4$, 1.3 mM KH$_2$PO$_4$, 0.63 mM CaCl$_2$, 0.74 mM MgSO$_4$, 5.3 mM glucose, 0.1 mM ascorbic acid, pH 7.4) containing 1% bovine serum albumin (BSA). Microvessel protein levels were determined with the Biorad DC protein assay kit (Hercules, Calif.). Incubation buffer, PACAP27 (4 μl of 0.8 nM), and any additives as indicated below were mixed with the 45 μl suspension of cells to a final volume of 60 μl (to give a final PACAP27 concentration of 53 pM) and incubated for 2.5 min at room temperature unless otherwise specified. At the end of incubation, samples were assayed for protein-bound radioactivity by vacuum filtration through Gelman Sciences glass microfiber filters (Ann Arbor, Mich.) pretreated with 0.5% polyethyleneimine. Filters were washed three times with 4 ml of incubation buffer at 4° C. The radioactivity trapped on the filters was measured using a gamma-counter. Nonspecific binding was determined in the absence of microvessels and under the above conditions was 20% of the total binding (TB). The specific binding was calculated as total binding minus nonspecific binding and expressed as a percentage. All experiments were performed in triplicate on at least three occasions and the results reported as means with their standard errors.

Inhibition of Specific Binding of PACAP27. Self-inhibition was tested by adding varying amounts of unlabeled PACAP27. The percent of specific binding was calculated by taking the % TB for microvessels incubated with 0.8 nM PACAP27 as 100% and without microvessel incubation as 0%. An n of 3 was used per concentration. The fmol specifically bound was calculated by dividing the percent of specific binding by 100 and multiplying by the pM (PACAP27 and any unlabeled PACAP27 combined) of the incubation solution and by the volume. This was plotted against the nM in the media and the relation fitted to a one-site hyperbolic binding model.

Inhibition of I-PACAP27 Binding by PACAP Related Peptides. The effects of 50 nM of unlabeled PACAP27, PACAP38, the PACAP antagonists PACAP 6-27 and PACAP 6-38 (Bachem, Torrance, Calif.), and VIP (Sigma, St. Louis, Mo.) on PACAP27 specific binding was determined. Results were expressed as percent of control.

Isolation of PACAP27 Transporter (PTS-6). Microvessels prepared from 10 male CD-1 mice were lysed in water for 2 h at 4° C. and centrifuged to obtain the membrane pellet. I-PACAP27 ($10^5$ cpm) and the membrane fraction were incubated for 20 min in a volume of 20 μl of incubation buffer at room temperature. Disuccinimidyl suberate at a concentration of 0.05 M was used to crosslink the I-PACAP27 to membrane binding sites by incubating for 15 min at room temperature. The cross-linked membranes were then subjected to hydrophobic fractionation using the MEM-PER kit (Pierce, Rockford, Ill.). The hydrophobic fraction was loaded in duplicate onto a 10% Bis/Tris denaturing gel. One half of the gel was subjected to Western transfer to a nylon membrane and stained with Coomasie blue. The other half of the gel was air-dried and subjected to autoradiography. After visualization of the radioactive bands, the autoradiogram was aligned to the Coomasie stained membrane and the corresponding band was cut out. The 55 kDa band was sent for protein identification to the Taplin Mass Spectrometry Facility (Harvard Medical School).

Effects of Antisense Oligonucleotides to ATP Synthase beta Subunit on Brain-to-Blood Efflux. Three non-overlapping regions of the mouse ATP synthase beta subunit were used to construct three enzymatically resistant phosphorothioate oligonucleotide antisense molecules (Midland Certified Reagent Company, Inc, Midland, Tex.):

```
an 18-mer to the 144-9 region:
5'-(_P=S)TCCAATGACATTCATGAT-3';     (SEQ ID NO: 1)

a 15-mer to 328-332 region:
5'-(_P=S)CTGGTAGCCTACAGC-3';        (SEQ ID NO: 2)
and a 17-mer to the 249-353/4 region:
5'-(_P=S)ATCGATCCCTTCTTGGT-3'.      (SEQ ID NO: 3)
```

The effect of these antisense oligonucleotides on PTS-6 efflux activity was determined after both their i.c.v. and i.v. administration.

To test the effectiveness of PTS-6 antisense oligonucleotides after their icv administration, two month old male CD-1 mice kept on a 12/12 hour light/dark cycle with food and water freely available were anesthetized on the day of study with 0.15 ml of 40% urethane. The scalp was removed and a hole made into the lateral ventricle, 1.0 mm lateral and 1.0 mm posterior to the bregma, with a 26 gauge needle with a tubing guard which kept the depth of the holes constant (3.0-3.5 mm). Mice received an i.c.v. injection of 1.0 ul lactated Ringer's solution with 1% BSA containing 100 ng of each of the three antisense oligonucleotides. Immediately (t=0) or at varying times (0.5, 2, 4, 8, 18, 24, 36, 48, or 72 h) after the antisense injection, mice received a second icv injection of 1.0 μl lactated Ringer's solution with 1% BSA containing $1.5(10^5)$ cpm of I-PACAP27. Mice were decapitated 10 min after the i.c.v. injection of I-PACAP27, the brains removed, and the level of residual radioactivity in brain determined by counting in a gamma counter. Mice which had been killed by an overdose of urethane were used to determine the level of residual radioactivity in brain in the total absence of transport (R) and mice which did not receive antisense were used to determine the level of residual activity in unimpaired transport (N). The percent of transport (% T) was calculated with the equation:

$$\% T = 100(R-A)/(R-N)$$

where A is the residual activity in brain in the antisense treated mice and N is the residual activity in mice not treated with antisense.

Specificity of the i.c.v. administered antisense oligonucleotides for I-PACAP27 efflux was tested by determining their effects on efflux of the PTS-1 ligand Tyr-MIF-1, the P-glycoprotein ligand β-endorphin, free iodine, which is a ligand for a perchlorate-sensitive active transporter and on PACAP38. Mice received an icv injection of lactated Ringer's solution with 1% BSA either containing or not containing (control) the three oligonucleotide antisenses. After 24 h, the mice received a second icv injection containing radioactive PACAP38, Tyr-MIF-1, β-endorphin, or free iodine, were decapitated 10 min later, and the level of residual activity in brain determined in a gamma counter. For comparison, I-PACAP27 transport was also studied 24 h after the i.c.v. injections. Results were expressed as the percent of the injected dose remaining in brain (% Inj).

To test the effectiveness of PTS-6 antisenses after their intravenous administration, two month old male CD-1 mice kept on a 12/12 hour light/dark cycle with food and water freely available were given an injection by tail vein of 0.9% saline with or without 10 μg/mouse of each of the three antisenses. To determine the specificity of the PTS-6 antisense on I-PACAP27 efflux, three other antisenses were also injected iv. These were:

a 10-mer directed against the methionine enkephalin region of preproenkephalin:

```
(5'-(_P=S)TCATGAAGCC-3'    (SEQ ID NO: 4))
```

(Banks et al., Peptides 27, 784-796, 2006);

a 42-mer directed at the amyloid β mid-region of amyloid precursor protein:

```
                                         (SEQ ID NO: 5))
(5'-(_P=S)GGCGCCTTTGTTCGAACCCACATCTTCAGCAAAGAACACC
AG-3'
```

(Kumar et al., Peptides 21, 1769-1775, 2000); and a random 40-mer:

```
                                         (SEQ ID NO: 6))
(5'-(_P=S)GATCACGTACACATCGACACCAGTCGCCATGACTGAGC
TT.
```

After 24 h, the mice were anesthetized with urethane and both jugular veins exposed. The thorax was opened, the descending thoracic aorta clamped, both jugular veins severed, and lactated Ringer's solution containing I-PACAP27 (250,000 cpm/ml) perfused through the left ventricle of the heart at the rate of 2 ml/min. $^{131}$I-PACAP38 (hereafter referred to as I-PACAP38) was perfused in some mice treated with PTS-6 antisense. After 5 min, the perfusion was stopped and 20 ml of lactated Ringer's solution was infused through the left ventricle of the heart to wash out the vascular space of the brain. The level of radioactivity was determined in the brain and in an aliquot of the perfusion fluid and results expressed as the brain/perfusion ratio in units of μl/g.

Co-localization of beta-F1 ATPase and PACAP27 Binding to Brain Microvessels. Microvessels prepared from 10 male, 8-week old CD-1 mice were resuspended in 100 μl of incubation buffer containing 1% BSA. The microvessels were divided into a control group and an experimental group of 25 μl each. PACAP27 (2.5 μg) was added to the experimental group and the volume in both tubes was increased to a total of 30 μl using the aforementioned incubation buffer. The microvessels were then incubated for 20 min at room temperature with gentle mixing and tapping. Disuccinimidyl suberate (1.5 μl) at a concentration of 0.05 M was used to crosslink PACAP27 to membrane binding sites by incubating for 10 min at room temperature. The cross linked membranes were then washed in 1 ml aliquots of the incubation buffer by inverting the tubes several times and centrifuging at 4000 rpm for 3 min at 4° C. The supernatant was carefully removed and the pellet washed three more times with incubation buffer. The washed and pelleted microvessels were resuspended in 100 μl of incubation buffer in preparation for electron microscopy analysis.

The treated microvessels were re-suspended and 25 μl was applied to each etched ring on glass slides (Gold Seal Products) which had been coated with poly-L-lysine solution (Sigma-Aldrich) and the microvessels were allowed to settle and attach to the slide. After 60 minutes the microvessels were fixed by adding 25:1 of 4% formaldehyde in PBS to each ring for 10 min. The preparations were then washed by adding PBS to each ring. To minimize loss of microvessels during this wash and subsequent steps 50-100 μl of solution was applied to one side of the etched ring via a pipette while simultaneously removing an equivalent volume from the opposite side of the ring with a second pipette. After washing several times with PBS the preparations were blocked with 3% bovine serum albumin (BSA) in PBS for 30 min and then rinsed briefly in 0.1% BSA in PBS. The microvessels were then incubated with a solution of anti-PACAP antibody and anti-transporter antibody (diluted 1:200 and 1:1000 respectively) in 0.1% BSA in PBS for 16 hr in a humidified sealed container at 4° C. Following washing with 0.1% BSA in PBS they were incubated in a solution of goat anti-rabbit IgG rhodamine red™-X and donkey anti-mouse IgG Alexa Fluor® 488 (1:500 and 1:750 respectively; both from Molecular Probes) for 1.5 hr in a sealed humidified container at RT. The microvessels were then washed several times with PBS and mounted in Fluorosave (Calbiochem) mounting medium. The preparations were examined with a BioRad MRC1024 confocal microscope and digital images processed and merged using Confocal Assistant Software. Negative controls consisted of omitting the PACAP27 in the initial incubations, using normal rabbit and normal mouse IgG as primary antibodies and leaving out the secondary antibody. Immunostaining for beta-F1 ATPase and PACAP co-localized on isolated brain microvessels which comprise the vascular BBB.

Statistics. Means are reported with their n and standard errors. Two groups were compared by Student's t-test. More than two groups were compared by analysis of variance (ANOVA) followed by Newman-Keuls post-test.

First, the in vitro BBB model of brain microvessels isolated from mouse brain were used to characterize I-PACAP27 binding. FIG. 1A shows the relation between incubation time and the percent specific binding of I-PACAP27 to mouse brain microvessels in the range of 1.0 to 20 min (n=3/time). Nonspecific binding was 10-20% of total binding. Specific binding reached a maximum by about 20 min. Results fitted to a one site binding hyperbolic model showed that 50% of maximal binding occurred by 3∀1.2 min. Based on this, further studies were conducted at 2.5 min incubation times. Specific binding was temperature dependent (FIG. 1B; n=3). A statistically significant difference occurred among the groups [F(2,6)=15.10, p<0.05] and specific binding of I-PACAP27 at 4° C. was significantly less compared to 25° C. and 37° C. (p<0.05). The effect of pH on I-PACAP27 binding was studied (FIG. 1C; n=3). When the percent specific binding was plotted against pH, the results suggested either a parabolic curve with its peak at pH 7.36 or a bimodal curve. ANOVA [F(6,14)=6.39, p<0.005] followed by the range test, however, showed only the pH 6.1 value differed from the values for 7.2, 7.7, and 8.1. Subsequent experiments were conducted at pH 7.4 at room temperature for 2.5 min incubation time.

FIG. 2A shows the self-inhibition of PACAP27 binding by increasing concentrations of unlabeled PACAP27 (1-100 ng/tube; n=2-3/concentration) in the mouse brain microvessels. The results are expressed with the specific binding at 53 pM of PACAP27 set to 100% and nonspecific binding at 0% and each data point represents 2-3 replicates. An inverse relation existed between the log concentration of unlabeled PACAP27 and specific binding (n=6, r=0.982, p<0.001, slope=−28.1, Y intercept=72.9). Based on the results in FIG. 2A, an expanded dose response curve of 9 concentrations (0.5-180 nM with repeats at the 20 and 180 nM concentrations; n=3/concentration) was used to measure Kd and Bmax (FIG. 2B). The binding data were analyzed for best fit comparing a one site and two site hyperbolic binding model with the Prism program. The results indicated a one-site model produced the better fit with a dissociation constant (Kd) of 38.56∇8.94 nM and binding maximum (Bmax) of 87.48∇8.69 fmol.

To determine the specificity of the PACAP binding site, mouse brain endothelial cells were incubated with PACAP27 in the presence of 50 nM concentration of one of the two naturally occurring forms, PACAP27 and PACAP38, one of two PACAP antagonists, PACAP(6-27) and PACAP(6-38), or VIP; n=6/group. ANOVA showed a statistically significant effect among the groups shown in FIG. 3: F(5,30)=11.94, p<0.0001). The binding of PACAP27 to cells was not affected by VIP. The displacing affinity of the PACAP-related peptides were not statistically different, but had an arithmetic hierarchy of PACAP38>PACAP27>PACAP(6-38)>PACAP(6-27) for inhibiting PACAP27 binding to brain microvessels.

Autoradiography of I-PACAP27 cross linked to isolated microvessel membranes showed a prominent band at 55 kDa. Analysis by mass spectrophotometry showed this protein to be ATP synthase beta subunit, also known as β-F1 ATPase. Subsequent mass spectrophotometery confirmed this band to be beta-F1 ATPase.

A single injection containing the three antisenses administered icv as a cocktail produced an inhibition in the transport of icv administered I-PACAP27 that began within 30 min of administration and lasted at least 24 h (FIG. 4A): F(10,54)=8.74, p<0.001, n=6-7/group. The icv antisense cocktail as assessed by t-test had no effects on the ligands of three other BBB efflux systems (FIG. 4B, n=8/group for 1 and β-endorphin and n=14 for Tyr-MIF-1) nor for I-PACAP38 (n=17), but did produce a significant inhibition in I-PACAP27 efflux (t=4.5; p<0.005, n=4/group), where all ligands were also administered icv 24 h after the cocktail.

Inhibition of the efflux system should allow an increased retention by brain of PACAP27 presented to the brain through its vasculature. A single injection of the antisense cocktail by tail vein 24 h before study produced a four-fold increase in the uptake of I-PACAP27 (FIG. 4C), but not I-PACAP38, delivered by brain perfusion. The antisenses directed against pre-proenkephalin, amyloid precursor protein, or the random 42-mer produced no statistically significant effect on uptake of I-PACAP27.

Co-localization of PACAP27 and beta-F1 ATPase is shown in FIGS. 5A-F. FIGS. 5A-C show a capillary with exogenous PACAP27 added and FIGS. 5D-F show a control capillary in which PACAP27 was not added. FIGS. 5A and 5D show beta-F1 ATPase immunoactivity (green), FIGS. 5B and 5E show PACAP27 immunoactivity (red) and FIGS. 5C and 5F show co-localization. As expected, no PACAP27 immunoactivity was seen (FIGS. 5E and 5F) when PACAP27 was not preincubated. FIG. 5C shows that PACAP27 and beta-F1 ATPase immunoactivities co-localize.

The vascular BBB binds I-PACAP27 at a single, unique site. This protein is the PACAP27 efflux component of PTS-6 from brain endothelial cells. The identified protein, beta-F1 ATPase, acts as a lipoprotein transporter or peptide receptor at other cell types and is known to be expressed by brain endothelial cells. Beta-F1 ATPase immunoactivity co-localized on brain endothelial cells with PACAP27. Inhibition of beta-F1 ATPase with specific antisenses reduced efflux of PACAP27 but not other substances including PACAP38 from brain and greatly increased influx into brain.

All of the compositions and methods disclosed and claimed herein can be made and executed without undue experimentation in light of the present disclosure. While the compositions and methods of this invention have been described in terms of embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 2

Modulation of Aβ by Inhibition of LRP-1 Expression

Materials and Methods

Animals: Male CD-1 mice (>8 wks old; weighing 30-35 g) were used (Charles River, Wilmington, Mass.) in all experiments. Unless otherwise stated, animals were housed in groups of four in plastic cages with sawdust bedding. Food and water were available ad libitum. The mice were maintained in a temperature-controlled (19-23° C.) room on a 12:12 h light-dark cycle (lights on at 0600 h) with experiments conducted during the light phase. All procedures were in accordance with the NIH Guidelines for the Care and Use of Laboratory Animals and were approved by the Veterans Affairs—Saint Louis Animal Care Committee Synthesis of PS-ODNs: PS-ODNs were synthesized by the Midland Certified Reagent Company (Midland, Tex.). The sequences of the three PS-ODNs used in these studies are as follows:

```
19 mer (Anti-LRP1):
5'-(_P=S)TGATTTGGTCTCTGCAGGC-3',;    [SEQ ID NO: 7]
```

23 mer (Anti-LRP1):
5'-(_P=S)GTGTGGGCCGATGCAAACAGCAG-3';[SEQ ID NO: 8]
and 21 mer (Random):
5'-(_P=S)GAGAAGGTTGTGTGATCTTCA.. [SEQ ID 9]

The 23 mer (nt 442-418) was designed to bind to the translation start site and the 19 mer (nt 559-541) to an LRP-1 coding region. The National Center for Biotechnology Information (NCBI) GenBank accession number used to design these PS-ODNs was NM_008512. In the majority of experiments, the 19 mer and 23 mer PS-ODNs were administered simultaneously in equal amounts (ex. 5 μg of 19 mer+5 μg of 23 mer=10 μg total antisense), and is referred to as the cocktail. A 21 mer PS-ODN was designed for use as a control sequence ("random") by randomly picking letters from the two sequences used to construct the 19 mer and 23 mer PS-ODNs and is the average length of the two PS-ODNs that comprise the cocktail. A check of the NCBI mouse nucleotide Basic Alignment Search Tool (BLAST) database showed that this random antisense did not share sequence homology with any mouse genes. The lyophilized PS-ODNs were dissolved in 0.9% NaCl at a concentration of 1 mg/ml and stored at −70° C. until use.

Reagents: Lyophilized 42 amino acid murine amyloid beta ($A\beta_{42}$; purchased from Bachem AG, Switzerland) was solubilized at a concentration of 1 mg/ml in a solution of 0.1% $NH_4OH$ and stored at −70° C. until use. All other reagents were purchased from Sigma (Sigma-Aldrich, St. Louis, Mo.) unless otherwise specified.

Iodination ($A\beta_{42}$ and RAP): Murine $A\beta_{42}$ was radioactively labeled with the chloramine T method[30]. Chloramine T and sodium metabisulfite were dissolved at concentrations of 1 mg/ml and 10 mg/ml, respectively, in 0.25 M chloride-free sodium phosphate buffer (PB) containing 0.25 M $NaH_2PO_4$+0.25 M $Na_2HPO_4$, pH=7.5. The reaction mixture for the iodination procedure consisted of the following: 2 mCi of $^{131}I$ (PerkinElmer, Boston, Mass.), 5 μg of peptide (either $A\beta_{42}$ or RAP), and 10 μl of chloramine T. After a 60 s incubation at room temperature, 10 μl of sodium metabisulfite was added to terminate the reaction. The iodinated material ($A\beta_{42}$) was purified by filtration on a G-10 Sephadex column that had previously been washed with 5.0 ml of PB. Material from the column was eluted with 100 μl aliquots of PB. The level of radioactivity in each aliquot was determined by counting 1 μl of each fraction in a Wallac Wizard gamma counter (EG & G Wallac, Turku, Finland). The two fractions that corresponded to the monoiodinated compound were identified by elution position and peak in radioactivity. The integrity of the radioactive label for these two fractions was confirmed by precipitation with 30% trichloroacetic acid (TCA). Results of the TCA precipitation indicated that radioactive incorporation was greater than 95%. Following iodination, $^{131}I$-Aβ (hearafter referred to as I-$A\beta_{42}$) was stored at −70° C. and used within 48 h of radiolabelling.

Label with $^{32}P$(PS-ODNs): This method has been described previously (Banks et al. Peptides 27, 784-796, 2006). Briefly, PS-ODNs were end-labeled by mixing 1-10 μg of PS-ODN with 1.5 μl of 10× kinase buffer, 1.5 μl of T4 Polynucleotide Kinase (New England Biolabs, Ipswich, Mass.) and 10 μl of [$\gamma^{32}P$] ATP (Perkin Elmer, Boston, Mass.). Next, the mixture was incubated in a 37° C. water bath for 45 min. After incubation, the kinase was heat inactivated by incubating the sample in a heat block set to 65° C. for 5 min. Labeled oligonucleotide (P-Olg) was removed from the reaction mixture by ethanol precipitation followed by centrifugation. For the initial ethanol precipitation, the labeled PS-ODN was mixed with 80 μl of distilled water ($dH_2O$), 10 μl of 3 M Na-acetate (pH=5.0), 2-5 μl of Pellet Paint Co-Precipitant (Novagen, Madison, Wis.) and 300 μl of cold ethanol. This mixture was then subjected to an overnight incubation in a −70° C. freezer. The next day, P-Olg was separated from the mixture by centrifugation at 13,000 rpm for 20 min. After removing the supernatant, the pellet (containing the P-Olg) was resuspended in 500 μl of cold ethanol and subjected to a second centrifugation at 13,000 rpm for 15 min. This centrifugation step was repeated an additional three times to remove any remaining unreacted radioactivity. After the final wash, the pellet was resuspended in 100 μl of $dH_2O$ and the level of radioactivity was determined by counting 1 μl of the sample in a Wallac scintillation counter (EG & G Wallac, Turku, Finland). After radiolabelling with $^{32}P$, both P-Olgs (P-19 mer or P-23 mer) were stored at −70° C. and used within 48 h.

Methods for Acute Antisense Administration Studies

Isolation of mouse brain microvascular endothelial cells (BMECs): BMECs were isolated using a modified method of Szabó et al. (Neurobiology 5, 1-16 (1997). In brief, cerebral cortices from 8-week-old CD-1 mice were isolated, cleaned of meninges, and minced. The homogenate was digested with collagenase type II (1 mg/mL) and DNase I (30 U/mL) in Dulbecco's Modified Eagle Media (DMEM) [containing 100 units/mL penicillin, 100 μg/mL streptomycin, 50 μg/mL gentamicin and 2 mM GlutaMAX-I (Invitrogen, Carlsbad, Calif.)] at 37° C. for 40 min. After digestion, 20% bovine serum albumin (BSA) dissolved in DMEM was added. The sample was then centrifuged at 1,000×g for 20 min, the supernatant containing the neurons and glial cells was removed, and the pellet containing the microvessels further digested at 37° C. for 30 min with collagenase/dispase at a concentration of 1 mg/mL (Roche, Mannheim, Germany) and DNase I (30 U/mL dissolved in DMEM). After the second enzyme digestion, we then layered the pellet on a 33% Percoll (Amersham Biosciences, Piscataway, N.J.) gradient and centrifuged at 1,000×g for 10 min to separate the microvessels. To create the Percoll gradient, 33% Percoll solution (8 mL Percoll, 14.4 mL phosphate buffered saline; PBS, 0.8 mL plasma derived serum; PDS, and 0.8 mL 10×PBS) was centrifuged at 20,300×g for 1 h, prior to this step. After the centrifugation, a layer of microvessels was formed in the middle of the Percoll gradient, above the red blood cell layer. Microvessels were washed by resuspension in DMEM followed by centrifugation at 1,000×g for 10 min. The microvessel pellet was then dissolved in DMEM and the mix was seeded on culture dishes previously coated with a coating buffer (0.05 mg/mL fibronectin, 0.05 mg/mL collagen 1 and 0.1 mg/mL collagen IV) and allowed to dry. The freshly seeded cells were incubated at 37° C. for 24 h with a humidified atmosphere of 5% $CO_2$/95% air in a 1:1 mixture of DMEM and Ham's F12 Nutrient Mixture (DMEM/F-12) that had been supplemented with 20% plasma-derived bovine serum (Quad Five, Ryegate, MT), 100 units/mL penicillin, 100 μg/mL streptomycin, 50 μg/mL gentamicin, 2 mM GlutaMAX-I and 1 ng/mL basic fibroblast growth factor (bFGF). By the next day, the BMECs had migrated from the isolated capillaries and started to form a continuous monolayer. To eliminate all contaminating cells (mainly pericytes and glial cells), BMECs were treated with puromycin (4 μg/mL) for the first 2 days of culture (Perriere et al. J Neurochem 93, 279-289, 2005). After 2 days, the puromycin was removed and culture media was changed every other day. After 7 days of culture, BMECs had reached 80-90% confluency.

Culture of BMECs on Transwell inserts: BMECs were seeded ($4 \times 10^4$ cells/insert) on a fibronectin-collagen IV (0.1 and 0.5 mg/mL, respectively)-coated polyester membrane (0.33 cm$^2$, 0.4 Mm pore size) that was contained inside of a Transwell-Clear insert (Costar, Corning, N.Y.) and the inserts placed (one per well) in 24-well culture plates (Costar). These cells were cultured in DMEM/F-12 media that was supplemented with 20% plasma-derived bovine serum (PDS), 100 units/mL penicillin, 100 µg/mL streptomycin, 50 µg/mL gentamicin, 2 mM GlutaMAX-I, 1 ng/mL bFGF and 500 nM hydrocortisone. Cultures were maintained at 37° C. with a humidified atmosphere of 5% $CO_2$/95% air until the BMEC monolayers reached confluency (a process that took around 3 days). After the cells became confluent, the integrity of the BMEC monolayers was tested by measuring transendothelial electrical resistance (TEER). TEER measurements were taken before the experiments using an EVOM Epithelial Tissue Voltohmmeter equipped with an STX-2 electrode (World Precision Instruments, Sarasota, Fla.).

Transport of I-A$\beta_{42}$ in BMEC cultures: For the transendothelial transport experiments, the media was first removed from all wells and then the BMECs were washed with a physiological buffer (141 mM NaCl, 4.0 mM KCl, 2.8 mM CaCl$_2$, 1.0 mM MgSO$_4$, 1.0 mM NaH$_2$PO$_4$, 10 mM HEPES, 10 mM D-glucose, pH 7.4) containing 1% BSA. Physiological buffer was added to the luminal chamber (0.1 mL) and abluminal chamber (0.6 mL) of the Transwell insert. For the purpose of this experiment, I-A$\beta$42 ($1 \times 10^6$ cpm/mL) was loaded into the abluminal chamber and the luminal chamber served as the collecting chamber. The sampling volume for the luminal chamber was 90 µL.

To quantify I-A$\beta$42 efflux, samples were removed from the collecting chamber at various time points (10, 20, 40 and 60 min) and, after their removal, they were immediately replaced with an equal volume of fresh physiological buffer (supplemented with 1% BSA). All samples were then mixed with 30% TCA (for a final concentration 15%) and centrifuged at 5,400×g for 15 min at 4° C. The amount of radioactivity in the TCA precipitate was determined in a gamma counter. The permeability coefficient and clearance of TCA-precipitable I-A$\beta_{42}$ was calculated according to the method described by Dehouck et al (J Neurochem 58, 1790-1797, 1992). Clearance was expressed as microliters (µL) of radioactive tracer diffusing from the abluminal to luminal chamber and was calculated from the initial level of radioactivity in the abluminal chamber and final level of radioactivity in the collecting (or luminal) chamber. This relation is represented by the following formula:

$$\text{Clearance (µL)} = [C]_C \times V_C / [C]_L,$$

where $[C]_L$ is the initial level of radioactivity in the abluminal chamber (in cpm/µL), $[C]_C$ is the level of radioactivity in the luminal chamber (in cpm/µL) at any given time, and $V_C$ is the volume of the collecting chamber (in µL). During the initial 60 min period of the experiment, the clearance volume increased linearly with time.

When the volume cleared from the abluminal chamber was plotted versus time, the slope of the clearance curve was estimated by linear regression analysis. Below, the slope of the clearance curve for the BMEC monolayers is denoted as PS$_{app}$, where PS is the permeability-surface area product (in µL/min). The slope of the clearance curve with a control membrane (without BMECs) is denoted by PS$_{membrane}$. The actual PS value for the BMEC monolayers (PS$_{trans}$) was then calculated from the following formula:

$$1/PS_{app} = 1/PS_{membrane} + 1/PS_{trans}$$

After their calculation with this formula, the PS$_{trans}$ values were then divided by the surface area of the Transwell inserts (0.33 cm$^2$) to generate the permeability coefficient (P$_{trans}$, in cm/min).

The saturability of I-A$\beta_{42}$ efflux was measured by adding unlabeled A$\beta_{42}$ (1 µg/mL) to the loading chamber with the radiolabeled protein ($1 \times 10^6$ cpm/mL). When the effect of antisense cocktail on I-A$\beta$42 efflux was examined, either the antisense cocktail or control random antisense was dissolved in serum-free DMEM/F12 media. Cells were washed with serum-free medium and then exposed for 24 h to 1 µg/mL of cocktail or random antisense added into the luminal side of the chamber.

Isolation of mouse brain microvessels (MBMs): Mouse brain microvessels (MBMs) were isolated by a modification of a method of Gerhart et al (Brain Res Bull 21, 785-793, 1998). All glassware was pre-coated with phosphate buffered saline (PBS) supplemented with 1% BSA (1% BSA/PBS). This was done to minimize adhesion and to maximize recovery of microvessels. Briefly, ten to twelve cerebral cortices from adult male CD-1 mice were collected and the meninges removed. They were homogenized on ice in 5 mL of cold stock buffer (25 mM HEPES, 1% dextran and 1 envelope of Minimum Essential Medium (Invitrogen), pH 7.4). The homogenate was then filtered through a series of nylon mesh membranes (300 µm, then twice through 100 µm; Spectrum, Houston, Tex.), mixed with an equal volume of 40% dextran in stock buffer, and centrifuged at 3,000×g for 30 min at 4° C. The supernatant along with the lipid layer was removed and the pellet was then resuspended in stock buffer. This suspension was passed through a 25 µm nylon mesh membrane (Bio-Design, Carmel, N.Y.). The microvessels on the surface of the membrane were washed with stock buffer four times, collected from the membrane, and then centrifuged at 3,000×g for 30 min at 4° C. After centrifugation, the supernatant was discarded and the microvessel pellets were resuspended in incubation buffer (129 mM NaCl, 2.5 mM KCl, 7.4 mM Na$_2$PO$_4$, 1.3 mM KH$_2$PO$_4$, 0.63 mM CaCl$_2$, 0.74 mM MgSO$_4$, 5.3 mM glucose, 0.1 mM ascorbic acid, pH 7.4) until further use.

Immunohistochemistry of LRP-1 in isolated MBMs: Isolated MBMs were treated with either incubation buffer, random antisense, or antisense cocktail (10 µg/mL) in incubation buffer for 24 h. Microvessels were dropped onto glass slides and heat-fixed at 95° C. for 10 min. After fixation with 3.7% formaldehyde for 10 min at room temperature, they were permeabilized with 0.3% Triton X-100 in 1% BSA/PBS for 15 min at room temperature. Slides were treated with 10 µg/mL anti-LRP-1 antibody (H-80; Santa Cruz biotechnology, Santa Cruz, Calif.) in 1% BSA/PBS for an overnight incubation at 4° C. The next morning, they were washed once with PBS, three times with balanced salt solution (130 mM NaCl, 5.4 mM KCl, 1.8 mM CaCl$_2$, 4 mM MgCl$_2$, 20 mM HEPES, 5.5 mM glucose, pH 7.4) and once with PBS. After these wash steps, they were then incubated with 20 µg/mL Alexa Fluor 488-conjugated anti-rabbit IgG (Invitrogen) in 1% BSA/PBS for 1 h at room temperature. After washing, microvessels were covered with Vectashield Hard Set mounting medium (Vector Laboratories, Burlingame, Calif.) and coverslips were applied. Fluorescence was detected with Zeiss Axiovert 40 CFL fluorescent microscope (Carl Zeiss, Inc., Thornwood, N.Y.). Images were obtained from 5-6 microvessels in each group and mean fluorescent intensity was quantified using Image J analysis software (National Institute of Health, USA).

Calculation of Ki and exposure time: Multiple-time regression analysis was used to determine the rate of uptake of P-Olg from blood to brain (Blasberg et al., J Cereb Blood Flow Metab 3, 8-32, 1983; Morley et al., Neurobiol Learn Mem 78, 125-138, 2002; Banks et al. Diabetes 53, 1253-1260, 2004). For this analysis, the brain/serum ratios for time points ranging from 2 to 30 min after i.v. injection was plotted against their respective exposure times (Expt). Expt is used instead of real time because this value corrects for the clearance of the injected substance from the blood. Without this correction, the influx rate would be overestimated. In this graph of brain/serum ratios vs. their respective exposure times, the slope of the linear portion of the line represents the unidirectional influx constant (Ki), while the y-intercept represents the initial volume of distribution (Vi) in the brain at t=0. Expt will be calculated using the following formula:

$$Expt = [\int_0^t C_p(t)dt]/C_p t,$$

where t is time, $C_p$ represents the level of radioactivity in the serum and $C_p t$ is the level of radioactivity in the serum at time t.

Calculation of the percent of injected dose taken up per gram of tissue: For the purpose of these studies, mice were injected iv (into the jugular vein) with P-19 mer or P-23 mer ($5 \times 10^5$ cpm/200 µl of Lactated Ringer's solution (Baxter Healthcare Corporation, Deerfiled, Ill.) supplemented with 1% BSA). At various time points (2 min, 5 min, 7.5 min, 10 min, 15 min, 20 min, 25 min and 30 min) after injection, the brain or liver was removed, weighed and the level of radioactivity was quantified in a gamma counter. To determine the level of radioactivity in the serum, whole blood was collected from the carotid artery and centrifuged at 5000×g for 15 min in order to separate serum. Serum levels of radioactivity were determined by counting 50 µl of serum in a gamma counter.

The % of the injected dose taken up by each gram of either whole brain, brain region (hippocampus or frontal cortex) or liver tissue (% Inj dose/g brain) was calculated using the following formula:

$$\% \, Inj \, dose/g \, brain = 100(Am/Cpt - Vi)Cpt/Inj,$$

where Am/Cpt represents the brain/serum ratio at time t, and Inj is the mean dose injected i.v. Subtracting Vi from the tissue/serum ratio corrects for P-Olg in the vascular space of the whole tissue. This will remove the vascular component so that the quantities expressed represent only the P-Olg that has been taken up by tissue. The values for % Inj dose/g brain will be plotted against their respective time points (min).

Measuring saturability of brain uptake for cocktail ODNs: To determine if brain uptake of each individual P-Olg was saturable, 10 µg/mouse of unlabeled cocktail PS-ODN (either 19 mer or 23 mer) was included in the i.v. injection of either P-19 mer or P-23 mer at a dose of $5 \times 10^5$ cpm/200 µl of Lactated Ringer's solution supplemented with 1% BSA [LR-BSA]). Brain and serum samples were collected 30 min after i.v. injection. Results were expressed as brain/serum ratios.

Capillary depletion: This method was performed to determine the distribution of the iv cocktail PS-ODNs between brain tissue and the brain capillaries(Triguero et al., J Neurochem 54, 1882-1888, 1990; Gutierrez et al., J Neuroimmunol 47, 169-176, 1993). In these studies, mice received an iv injection of either P-19 mer or P-23 mer at a dose of $5 \times 10^5$ cpm/200 µl LR-BSA into the jugular vein. Washout of the vascular space was performed to remove any substances that were intravascular or loosely adhered to the capillary lumen of the brain microvasculature. This method of washing out the vascular space has been shown to remove more than 95% of the blood from the brain.

Mice were anesthetized with 40% urethane and, at 30 min after i.v. injection of P-Olg into the jugular vein, the abdomen was opened and arterial blood was collected from the abdominal aorta. Next, the thorax was opened with a midline sternal incision and the descending thoracic aorta was clamped to cut off the circulation to the lower body. Both jugular veins were severed and an 18-gauge needle connected to a 20 ml syringe containing lactated Ringers (LR) solution was inserted into the left ventricle of the heart. All 20 ml of LR were infused into the mouse heart over a period of 1-2 min. This washes out the vascular space of the brain and drains out the severed jugular veins. The brain was then removed, weighed, and placed in a glass homogenizer containing 0.8 ml of physiologic buffer (10 mM HEPES, 141 mM NaCl, 4 mM KCl, 2.8 mM $CaCl_2$, 1 mM $MgSO_4$, 1 mM $NaH_2PO_4$ and 10 mM D-glucose; this buffer was then adjusted to pH=7.4). After 10 strokes with the pedestal, a quantity of 1.6 ml of the physiologic buffer containing 26% dextran was added to the homogenate. Next, the homogenate was vortexed and homogenized a second time (3 strokes). All homogenization steps were performed at 4° C. on ice. The homogenate was then centrifuged at 5400×g for 15 min at 4° C. in a Beckman centrifuge with a swinging bucket rotor. After centrifugation, the supernatant containing the brain parenchyma was separated from the pellet (containing the brain microvasculature) and the level of radioactivity was determined with a Beckman scintillation counter.

Results from the capillary depletion experiments were expressed as the volume of distribution in the brain or capillaries for the injected substance. Volume of distribution ($V_D$) values were expressed as tissue (parenchyma or capillary)/serum ratios and were calculated for both fractions using the following formula:

$$V_D = (cpm/gram \, of \, tissue)/(cpm/ml \, of \, serum)$$

Statistical analysis was performed using Student's t-test.

Determination of mean regional brain uptake of cocktail PS-ODNs: Mean regional uptake into the hippocampus (HPC) and frontal cortex (FC) was determined for each individual cocktail PS-ODN. For the purpose of this study, mice were administered iv P-Olg, either 19 mer or 23 mer ($5 \times 10^5$ cpm/200 µl LR-BSA), into the jugular vein. Brains were removed and arterial blood was collected from the carotid artery at various time points (2, 5, 7.5, 10, 15, 20, 25 and 30 min) after administration. The whole blood was centrifuged at 5,000×g for 15 min and serum collected. The level of radioactivity was determined in the serum and brain with a scintillation counter. These values were used to calculate the % of the injected dose taken up per gram of brain region (% Inj/g Brain Region).

Results of these studies were expressed as the total mean regional uptake of each P-Olg over time from 2-30 min. Statistical significance was determined by two-way analysis of variance (ANOVA) followed by a Bonferroni post-test.

Acute effects of iv antisense: In studies in which mice were treated acutely with iv antisense cocktail, mice received an injection into the tail vein of cocktail (7 µg/100 µl saline) or saline (0.9% NaCl). The effects of antisense treatment on brain efflux of I-$A\beta_{42}$ (5,000 cpm/µl LR-BSA) at either 4, 12, or 24 h was then determined.

For these studies, I-$A\beta_{42}$ was administered by intracerebroventricular (icv) injection. Brains were collected at 0 and 10 min and the level of radioactivity was quantified with a gamma counter. The data collected from these studies was reported as the negative slope (-Slope) because this value represents the actual rate of I-A$\beta_{42}$ efflux. This value was determined from a graph created with multiple measures at the two time points (0 and 10 min). After the log of the mean % of the injected dose of radioactivity (amount detected/amount injected*100=% Inj Dose) in each brain was plotted against time (min), linear regression was used to create a line between these two points. The slope of this line is reported since this value represents the rate of efflux for the substance within the first 10 min after icv administration.

Quantitative real-time PCR for LRP-1 and RAGE mRNA: RNA was isolated from hemibrain homogenates of mice treated with repeated iv saline, random, or cocktail antisense (7 µg/100 µl) using the Qiagen RNeasy Lipid tissue mini kit protocol. Total cDNA was produced by reverse transcription using the Applied Biosystems Taqman reverse transcription system of 0.2 µl of purified RNA, 3 µl 10×RT buffer, 6.6 µl MgCl$_2$, 6 µl 2.5 mM dNTPs, 1.5 µl random hexamers, 0.6 µl Rnase inhibitor, and 0.75 µl Multiscribe RT. Samples were incubated for 10 min at 25° C., 30 min at 48° C., and 5 min at 95° C. Quantitative real-time PCR was performed in a Applied Biosystems 7300 Real-Time PCR System. Amplification was carried out in 25 µl reaction mixtures containing 1 µl of template cDNA, 0.5 µl of each 5 mm primer, 12.5 µl 2×SYBR green mastermix, and 10.5 µl PCR water. Cycling conditions were one cycle at 95° C. for 10 min, followed by 50 cycles of 95° C. for 15 s, and 60° C. for 1 min followed by one cycle at 95° C. for 15 s, 60° C. for 15 s and 95° C. for 15 s. Primers for quanitative real-time PCR were made using Primer 3 software (Whitehead Institute for Biomedical Research) and primer efficiency was between 95-105%. Sequences were as follows: RAGE forward 5'-ccctgagacgg-gactcttta (SEQ ID NO: 10), reverse 5'-gttggataggggctgtgttc (SEQ ID: 11); LRP-1 forward 5'-agtccacatgttcccatccg (SEQ ID NO: 12), reverse 5'-agagccaaggaaggaaagc (SEQ ID NO: 13) and Beta Actin forward 5'-ttcctccctggagaagag (SEQ ID NO: 14), reverse 5'-tgccacaggattccatac (SEQ ID:15). The relative amount of gene copies was extrapolated using the comparative Ct method with beta actin as a normalizer and Stratagene mouse standard RNA as a calibrator.

In vivo brain-to-blood efflux rate of icv antisense: A standard method was used to quantify brain-to-blood efflux rates (Banks et al., Neuroscience 121, 487-492, 2003; Jaeger et al., Proc Natl Acad Sci USA 102, 12495-12500, 2005). First, mice were anesthetized with an i.p. injection of 40% urethane. After the scalp was removed, a hole was made through the cranium (1.0 mm lateral and 0.5 mm posterior to bregma) with a 26-gauge needle. All of the needle except 2.5 to 3.0 mm of the tip was covered by PE-10 tubing. This ensured that the needle did not penetrate the floor of the ventricle. Injections were made into the lateral ventricle (icv) with a 1.0 µl Hamilton syringe.

In experiments in which brain efflux of the cocktail PS-ODNs were determined, each P-Olg (either P-19 mer or P-23 mer) was studied separately. A P-Olg (5×10$^3$ cpm/µl) was administered by icv injection. Mice were then decapitated at 2, 5, and 20 min after injection and the brain was removed. The amount of radioactivity present in the brain was measured by a scintillation counter. The amount of radioactivity in the brain at t=0 was estimated in mice overdosed with urethane. These mice were killed and 15 min later injected with radioactive material. Brains from these mice were removed 10 min after injection. The log of the mean % of the injected dose of radioactivity (amount detected/amount injected*100=% Inj Dose) in each brain was plotted against time (min) and linear regression analysis was used to create a line between these time points.

For studies in which the -Slope is reported, this value was determined from a graph created with two time points (0 and 10 min) as described above. After the log of the mean % of the injected dose of radioactivity (amount detected/amount injected*100=% Inj Dose) in each brain was plotted against time (min), linear regression was used to create a line between the multiple values at these two points.

In some experiments, mice received two icv injections (antisense cocktail or saline icv and, at t=30 min or t=24 h, icv I-A$\beta$4$_2$). In these cases, the dose of antisense given was 200 ng/µl LR-BSA and the dose of I-A$\beta_{42}$ given was 5×10$^3$ cpm/µl LR-BSA.

In the specificity experiment, mice received two icv injections. The first injection consisted of either antisense cocktail, random antisense, antisense directed against the amyloid precursor protein (APP), antisense directed against preproenkephalin (PPE) or saline at a dose of 1.0 µl LR-BSA. At t=24 h, I-A$\beta$4$_2$ was given icv at a dose of 5×10$^3$ cpm/µl LR-BSA. Neuronal cells have been shown to metabolize A$\beta$ in vitro by an LRP-dependent mechanism, however, the rate of this degradation is 50 to 100-fold slower than BBB efflux of A$\beta$ in vivo(Shibata et al., 2000). Because of this, all data collected on the effects of acute centrally administered antisense cocktail on I-A$\beta_{42}$ efflux was collected within 0-20 min after icv administration of I-A$\beta_{42}$.

Methods for Chronic Antisense Administration Studies

Chronic icv infusion of antisense: For chronic icv administration of antisense cocktail, random antisense, or saline, mice were implanted with Alzet mini-osmotic pumps (DURECT Corporation, Cupertino, Calif.). These pumps were adapted for central nervous system (CNS) delivery of compound by use of a brain infusion assembly kit (Alzet Brain Infusion Kit 3; DURECT). This kit provides a small length of catheter tubing used to attach the mini-osmotic pump to a brain infusion cannula which is used for site-specific delivery of drug.

After filling the pumps with drug, the fully assembled brain infusion apparatus was then primed overnight by incubation at 37° C. in a beaker of sterile saline (0.9% NaCl). Prior to implantation, mice were anesthetized with Isoflurane (Webster Veterinary Supply, Sterling, Mass.) and secured in a stereotaxic apparatus (David Kopf Instruments, Tujunga, Calif.). A subcutaneous (sc) pocket was then created from the scalp incision to the midscapular region on the back of the mouse by inserting a hemostat under the skin and then opening and closing the hemostat twice. This created a small tunnel under the skin into which the osmotic pump was inserted.

A midline sagittal incision was made in the scalp to expose the skull and a hole was drilled through the skull to reveal the site of cannula implantation. The icv stereotaxic coordinates, determined from a mouse brain atlas (Slotnick & Leonard. A stereotaxic atlas of the albino mouse forebrain. U.S. Department of Health, Washington D.C. (1975), were 0.5 mm posterior to the bregma, 1.0 mm to the right of the central suture, and 2.0 mm deep. The brain cannula was stereotaxically inserted into the lateral ventricle with the aid of an electrode holder (Stoelting Company, Wood Dale, Ill.). Following implantation, the cannula was then secured to the skull with orthodontic resin (powder and liquid mixed 1:2, both from Densply International Inc., Milford, Del.). The resin was allowed to harden and afterwards the scalp wound was closed with silk braided 4-0 (1.5 metric) sterile, nonabsorbable Ethicon suture (Ethicon Inc., Piscataway, N.J.) attached to a ⅜ circle, reverse cutting edge stainless steel (size 20) surgical needle (Miltex Inc, York, Pa.). The animal was then removed from the stereotaxic apparatus and placed in a clean cage. During recovery, all animals were housed individually with food and water available ad libitum. One week after pump implantation, mice were tested for learning ability in the active avoidance T-Maze, levels of Aβ were measured by ELISA and efflux of I-Aβ$_{42}$ was assessed (as described above).

For the purpose of these studies, mice were infused with either 0.9% NaCl (saline), random antisense, or antisense cocktail. The cocktail and random antisense PS-ODNs were dissolved in sterile saline and pumps were filled to infuse a concentration of either 100 ng/0.5 µl for one week.

Brain homogenization and LRP-1 isolation: After a 1 wk icv infusion of either saline, random or antisense cocktail (100 ng/h), brains were removed, weighed, and a 5× volume of extraction buffer A (1 M Tris HCl, 5 M NaCl, 0.5 M EDTA, 0.5 M EGTA, 100 mM NaVO$_4$, and Protease Inhibitor Cocktail; Sigma) was added. Homogenization was carried out with a Polytron Bench Top Homogenizer (Kinematica, Switzerland) at setting 22. Afterwards, samples were centrifuged (1,000×g) for 10 min at 4° C. The supernatant was removed and centrifuged a second time (21,460×g) for 40 min at 4° C. This second spin separates the cytosolic protein (in supernatant) from the membrane protein (in pellet). The small subunit of LRP-1 is located in the cytosolic fraction.

In order to extract the large subunit of LRP-1 from the membrane fraction, the pellet was resuspended in 1 ml of extraction buffer B (buffer A+0.5% Triton X-100), agitated for 1 h on ice, and subjected to centrifugation (21,460×g) for 40 min at 4° C. The supernatant collected from this sample contains the large subunit of LRP-1.

For all samples, protein levels were quantified with a BCA Protein Assay Kit (Pierce Biotechnology, Rockford, Ill.).

Western blot for LRP-1: Protein samples from whole brain homogenates from mice infused for 1 wk (100 ng/h) were separated in either NuPAGE Novex 3-8% Tris-Acetate or NuPAGE Novex 4-12% Bis-Tris precast gels (Invitrogen, Carlsbad, Calif.). After electrophoresis, protein was transferred from the gel onto a nitrocellulose membrane (0.45 µm Pore Size). Upon completion of the transfer, the membrane was washed in Tris-buffered saline (10 mM Tris.HCl+150 mM NaCl; pH=8.0) that was supplemented with 0.05% Tween 20 (TBS-T). After the wash, the membrane was blocked for 1 h at room temperature in a solution of 5% Blotto non-fat dry milk (Santa Cruz Biotechnology) dissolved in TBS-T (5% milk solution). After the blocking step, the primary antibody was added for an overnight incubation at 4° C. The following morning, the secondary antibody was diluted in the 5% milk solution and applied to the membrane for 1 h at room temperature. Following this, the membrane was washed and a 1:1 solution of Supersignal West Pico Stable Peroxide Solution and Supersignal West Pico Luminol/Enhancer Solution (Pierce, Rockford, Ill.) was added. Any bands present on the membrane were visualized by exposure to BioMax XAR Scientific Imaging Film (Kodak) and optical density was quantified using Image J analysis software.

Antibodies for Western blot: The following antibodies were purchased from Santa Cruz Biotechnology: the primary anti-LRP-1 antibody (for large subunit) was a rabbit polyclonal IgG (H-80, 1:200), the primary actin antibody was a rabbit polyclonal IgG (sc-1616R, 1:5,000) and the secondary antibodies were a goat anti-rabbit IgG conjugated to horseradish peroxidase (HRP) (sc-2004, 1:10,000) and a goat anti-mouse IgG conjugated to HRP (sc-2005; 1:10,000). The primary anti-LRP-1 antibody (for small subunit) was a mouse monoclonal IgG purchased from Calbiochem (5A6, 1:1,000).

Aβ extraction from brain: Total Aβ was extracted from hemibrains treated with antisense cocktail, random antisense, and saline treated animals (100 ng/0.5 µl/h one week infusion). Right hemibrains were placed in cold extraction buffer (50 mM NaCl, 0.2% diethylamine (DEA) and 1× Protease Inhibitor Cocktail, Sigma) was added at a concentration of 1 mL buffer/200 mg tissue. Samples were then homogenized (PowerMax AHS 200, VWR), and the homogenate centrifuged at 100,000×g for 30 min. The supernatant (which contained Aβ) was removed and a 10% volume of neutralization buffer (1.0 M Tris-HCl, pH=6.2) was added prior to storage at −80° C.

Aβ ELISA: Details of two-site sandwich ELISA procedures and antibodies for rodent Aβ have been published (Ramsden et al. J Neurochem 87, 1052-1055, 2003; Das et al. J Neurosci 23, 8532-8538, 2003; Kukar et al. Nat Med 11, 545-550, 2005). Carboxy-terminal specific antibody 13.1.1 was used for the detection of Aβ$_{40}$, and 2.1.3 was used for Aβ$_{42}$; rodent specific amino-terminal antibody (32.4.1) was used for both forms. Capture antibody was added (1.0 µg/well, in standard PBS, pH=7.4) to each of the inner wells of a Immunolon 96-well HBX Plate. Plates were blocked with blocking buffer [PBS, 1% Block Ace™ (Serotec), 1% bovine serum albumin (BSA), 0.05% NaN$_3$, pH=7.4]. Next, 50 µL of AC buffer [0.02 M sodium phosphate buffer (pH=7), 0.4 M NaCl, 2 mM EDTA, 0.4% Block Ace™, 0.2% BSA, 0.05% CHAPS, and 0.05% NaN$_3$] was added to prevent wells from drying while loading. Synthetic peptide standards (Chemicon) were prepared in neutralized extraction buffer. Standards and samples were loaded at least in duplicate at a quantity of 100 µL per well. After overnight capture at 4° C., plates were washed extensively with PBST (PBS+0.05% Tween-20) and 100 ng/well of HRP-conjugated antibody 13.1.1, in buffer D [0.02 M sodium phosphate, 0.0002% thimerosal, 2 mM EDTA, 0.4 M NaCl and 1% BSA, pH=7.0], was added to each well. After a second overnight incubation, plates were again washed extensively with PBST, and developed with TMB reagent (Kirkegaard & Perry Laboratories). The reaction was stopped with 6% o-phosphoric acid and read at 450 nm using a BioTek multiwell plate reader.

Active avoidance T-maze: This behavioral test has been described previously (Diano et al. Nat Neurosci 9, 381-388, 2006; Jaeger et al., Peptides 23, 1683-1688, 2002). Here, it was used to assess spatial learning in cocktail, random antisense and saline treated animals (100 ng/h one week infusion). Mice were trained to avoid footshock in the T-maze. The T-maze apparatus consisted of a black, plastic alley (46 cm long) with a start box at one end and two goal boxes (17.5 cm long) at the opposite end. The maze had a depth of 12.5 cm and width of 9.8 cm throughout. The floor of the maze consists of stainless steel rods. The start box of the maze was separated from the alley by a plastic guillotine door that prevented the mouse from entering the alley before the training started.

A training trial began when a mouse was placed into the start box and the guillotine door was raised. When the door was raised, a 65 db warning buzzer (conditioned stimulus) sounded simultaneously. After 5 s in the maze, 0.35 mA of footshock (unconditioned stimulus) was applied from a Coulbourn Instruments scrambled grid floor shocker (model E 13-08). The first goal box the mouse entered on the first trial was designated as the incorrect choice. At the end of each trial, the mouse was removed from the goal box and returned to its home cage. Following a 45 s intertrial interval, a new trial began by placing the mouse in the start box and raising the guillotine door. As the door is raised, the warning buzzer sounds and, 5 s later, the mouse received footshock if it remained in the start compartment or entered the incorrect goal box. Specifically, entry into the correct goal box terminated the buzzer and the footshock. Training continued until the mouse learned to run to the end of the start alley and enter the correct goal box in less than 5 s, thereby avoiding footshock. All mice were trained until they made their first avoidance of footshock. We trained to this criterion to avoid overtraining the mice, a situation that would make the test less sensitive to subtle differences in learning ability. The acquisition test scores for the T-maze were expressed as the mean trials until first footshock avoidance was made.

Open field activity: Locomotor activity was evaluated in cocktail, random antisense, and saline treated animals (100 ng/h one week infusion). Testing began by placing the mouse in a circular open field arena that was 45 cm in diameter with clear, plexiglass sides that were 30 cm high. Mice were given one trial each in which they were allowed to freely explore the open field for 15 min. A testing session started when the mouse was placed in the arena on the side, facing the wall. The distance each mouse traveled during the session was recorded in centimeters using a Polytrak recording system (San Diego Instruments, San Diego, Calif.). The mean distance traveled for each treatment group was expressed as the percent of the control group.

Recognition of a novel object: This method has been described previously(Jaeger et al., 2002). Briefly, recognition memory for a novel object was assessed in cocktail and random antisense treated animals (100 ng/h two week infusion). Prior to testing, mice were habituated for three consecutive days to the testing apparatus (a 58×66×11 cm white, plastic box). During habituation, each mouse was allowed to freely explore the testing apparatus for 5 min. On the first day of training, mice were placed in the testing apparatus for 5 min and allowed to explore a pair of identical objects (Objects A and B; both were 7×6.3×5.1 cm). On the second day of training, one of the original objects was replaced with a new, or novel, object (Object C; 8.2×3.8×7.4 cm). Mice were placed in the testing apparatus for 5 min and the amount of time each mouse spent sniffing or touching the novel object was recorded by an observer. Results from this study were expressed as the percent of time spent investigating the novel object.

Statistics: Statistical differences between two groups were determined using Student's t-test with Dunnets post test. In experiments with three or more means, either a one-way analysis of variance (ANOVA) or a two-way ANOVA was used to test for statistical significance followed by a Newman-Keuls or a Bonferroni multiple comparison post-test, respectively. All statistical analyses were carried out using Graph Pad Prism Software (Graph Pad, San Diego, Calif.).

Effects of Cocktail on I-A$\beta_{42}$ Efflux in Brain Microvascular Endothelial Cell (BMEC) Cultures We first tested the effectiveness of the cocktail in primary mouse BMEC cultures, an in vitro model of the BBB. As this model can become undifferentiated from the BBB phenotype, we first verified the presence of LRP-1. Results in FIG. 7a show that 1 μg/mL of A$\beta_{42}$ added to the abluminal chamber of the Transwell insert significantly ($p<0.01$) inhibited abluminal-to-luminal transport of A$\beta$ that had been radioactively labeled with $I^{131}$ (I-A$\beta_{42}$). This demonstrates the presence of a saturable efflux transporter for I-A$\beta_{42}$ in the BMEC cultures.

In FIG. 7b, BMEC cultures were treated with either random or cocktail antisense for 24 h at a concentration of either 1 μg/mL or 10 μg/mL. A two-way analysis of variance (ANOVA) revealed that treatment with the cocktail had a significant effect ($F_{1,46}=8.92$, $p<0.01$) and that, compared to random treated cultures, cocktail treated BMECs showed a significant decrease in I-A$\beta_{42}$ efflux ($p<0.05$) with no difference between the doses. These results show that treatment with the cocktail can produce a functional decrease in I-A$\beta_{42}$ efflux in vitro.

Effect of Cocktail on LRP-1 Expression in Isolated MBMs

Immunohistochemistry was used to verify that the cocktail could reduce LRP-1 protein expression in the brain microvasculature. For this study, we used isolated mouse brain microvessels (MBMs) which, unlike cultured BMECs, do not dedifferentiate[20].

FIGS. 7c-h show phase contrast (Figs. c, e and g) and immunofluorescence (Figs. d, f and h) micrographs of isolated MBMs that were treated with either incubation buffer, random or antisense cocktail (10 μg/mL) for 24 h. (*** these should project okay in gray scale) Treatment with cocktail was associated with decreased immunofluorescence, indicating reduced LRP-1. FIG. 7i shows the mean fluorescent intensity for each treatment group. Analysis by one-way ANOVA revealed that MBMs treated with cocktail demonstrated significantly less ($F_{2,11}=6.20$, $p<0.05$) fluorescent intensity (66.5%) compared to buffer and random antisense treated MBMs (100% and 111.14%, respectively).

CNS Pharmacokinetics of iv Cocktail PS-ODNs

We next wanted to determine the route of administration that would produce the most significant reduction in LRP-1 function in vivo. After acute intravenous (iv; jugular) administration, both of the PS-ODNs from the cocktail exhibited significant brain uptake (FIG. 7a-b). The rate of uptake for the P-19 mer (FIG. 7a) and the P-23 mer (FIG. 7b) was 0.18 μl/g-min and 0.20 μl/g-min, respectively. Co-administration of unlabeled PS-ODN significantly reduced uptake of the P-23 mer (FIG. 8d), but not the P-19 mer (FIG. 7c). Capillary depletion was conducted to determine the distribution of the individual cocktail PS-ODNs between brain capillaries and brain extravascular tissue (FIG. 7e-f). These studies were conducted with vascular washout, a treatment that removes radioactive PS-ODN reversibly bound to the capillary lumen. This allowed us to distinguish between material sequestered by or transported through the BBB (Triguero et al., J Neurochem 54, 1882-1888, 1990). For both the P-19 mer and the P-23 mer, although significantly more radioactivity was detected in the brain parenchyma ($p<0.001$), both P-Olgs were detected in the target tissue, the brain capillaries. A one-way ANOVA of mean regional uptake for the P-19 mer (FIG. 8g) and P-23 mer (FIG. 7h) showed that, for both PS-ODNs, there were significant regional differences in brain uptake ($F_{2,56}=1190$, $p<0.001$ and $F=F_{2,56}=18080$, $p<0.0001$ respectively). Results show that the 19 mer had a higher uptake in the frontal cortex whereas both antisenses showed high uptake into the hippocampus.

Functional Effect of Acute iv Cocktail on Brain Efflux of I-A$\beta_{42}$

Results presented in FIG. 9a are from experiments in which mice were treated with iv (tail vein) cocktail or saline and, at various time points afterwards, I-A$\beta_{42}$ by icv injection to determine efflux. Results of these studies showed that 12 h after iv cocktail there was a significant decrease in I-A$\beta_{42}$ efflux compared to saline treated mice ($p<0.001$). This roughly corresponds with the half-life of LRP-1 in human glioblastoma cells, reported as about 8-10 h(Bu et al., J Biol Chem 47, 29874-29882, 1994). 24 h after a single injection of iv cocktail, we saw a rebound in I-Aβ42 efflux.

The results that are plotted against the right Y-axis of FIG. 9a were obtained from mice that were treated with two iv injections of cocktail 12 h apart with mice studied 12 h after last injection (24 h after the first injection). The repeated injections of iv cocktail produced a profound decrease in I-A$β_{42}$ efflux. Compared to saline treated mice, mice treated with cocktail demonstrated only 0.87% efflux. FIGS. 9b-c show that this decrease in I-A$β_{42}$ efflux is specific for LRP-1 since repeated injections with the cocktail were associated with a significant decrease in brain mRNA for LRP-1 ($F_{2,6}$=6.61, p<0.05) but not for the blood-to-brain transporter for Aβ, the receptor for advanced glycated end products (RAGE).

Pharmacokinetics of iv Cocktail PS-ODNs for the Liver

When we conducted further studies to determine the degree of non-target tissue uptake, results revealed that both of the iv cocktail PS-ODNs were taken up into the liver in significant quantities. Table 1 compares the percent of the iv injected dose taken up per gram of brain or liver for each of the cocktail PS-ODNs. For these studies, the PS-ODNs were delivered iv and relative uptake into the brain and liver (from 5-30 min) were studied.

At t=30 min, liver uptake for each of the iv PS-ODNS was nearly 100 times greater than brain uptake. These results indicated that iv injection of our PS-ODNs would not allow us to target our cocktail to a specific tissue and would therefore increase our risk of obtaining a false positive. Because we eventually wanted to administer our cocktail by chronic delivery so that we could assess the effects of reduced LRP-1 on cognitive ability in mice, we concluded that peripheral administration of the cocktail would not be an ideal route for chronic administration since uptake of our cocktail ODNs into the liver over an extended period of time could produce hepatotoxicity.

CNS Pharmacokinetics of icv Cocktail PS-ODNs

The other possible route for BBB delivery was by administration directly into the brain, therefore, we next examined the pharmacokinetics of the cocktail PS-ODNs following acute intracerebroventricular (icv) injection (FIG. 9). Initial results indicated that, for the first 20 min after icv administration, neither the P-19 mer (FIG. 9a) nor the P-23 mer (FIG. 9b) showed appreciable efflux from the brain with half-lives of 231.5 min and 47.8 min, respectively. Since both of the PS-ODNs remain sequestered in the brain after icv injection, we concluded that central administration was not likely to produce effects in peripheral tissues.

Functional Effects of Acute icv Cocktail on Brain Efflux of I-A$β_{42}$

FIG. 9c shows the effects of icv cocktail on I-A$β_{42}$ brain efflux. In this experiment, mice were treated with icv cocktail or saline and, either 30 min or 24 h later, administered I-A$β_{42}$. At t=30 min, there was no effect on I-A$β_{42}$ efflux. At 24 h, however, cocktail treated mice demonstrated significantly decreased brain efflux of I-A$β_{42}$ ($F_{2,38}$=10.32, p<0.001). As a negative control, transport of two other peptides previously shown to be effluxed from the brain, the 27 amino acid form of the pituitary adenylate cyclase activating peptide (PACAP-27) and the melanocyte stimulating hormone inhibitory factor 1 (Tyr-MIF-1), were measured 24 h after either icv saline or cocktail. Results showed that efflux of these peptides were not significantly affected (data not shown).

Specificity of icv Cocktail-Mediated Effects on Brain Efflux of I-Aβ

To confirm the specificity of the icv cocktail, we treated mice with either saline, random, cocktail, a 42 mer antisense directed against APP or a 19 mer antisense directed against preproenkephalin (PPE) and, at t=24 h, measured brain efflux of I-A$β_{42}$ (FIG. 9d). Results indicate that icv cocktail significantly decreased I-Aβ42 efflux compared to saline (p<0.001) and random (p<0.05) antisense treated mice ($F_{2,44}$=7.65, p<0.01). Mice receiving either the 42 mer APP antisense or the 19 mer PPE antisense, however, demonstrated a significant increase ($F_{3,62}$=18.26, p<0.0001) in efflux of I-A$β_{42}$.

Effects of Chronic icv Cocktail on Brain Efflux of I-A$β_{42}$ and Brain Levels of Endogenous Mouse Aβ

In the following studies, mice were infused chronically with icv cocktail to produce a sustained decrease in LRP-1 expression. FIG. 10a shows I-A$β_{42}$ efflux in mice treated with saline, random and cocktail antisense. Results indicate that, mice receiving a 1 wk infusion of antisense cocktail (100 ng/h) demonstrate significantly less I-A$β_{42}$ efflux when compared to saline (p<0.001) and random (p<0.01) antisense treated mice ($F_{2,39}$=14.90, p<0.001).

To determine if the icv cocktail infusion (1 wk; 100 ng/h) altered brain levels of endogenous mouse Aβ, we used an ELISA to quantify brain levels of either A$β_{40}$ (FIG. 10b) or A$β_{42}$ (FIG. 10c). Results of these studies showed that cocktail treated mice demonstrated significantly higher levels of A$β_{42}$ compared to both saline (p<0.05) and random (p<0.01) treated mice ($F_{2,13}$=7.97, p<0.01). Although brain levels of A$β_{40}$, showed a similar trend, the results did not reach statistical significance due to the high levels of variability in the samples.

Effects of Chronic icv Cocktail on Learning Ability in the T-Maze and Recognition Memory for a Novel Object The T-Maze is an auditory-cued active avoidance paradigm that involves training the mouse to avoid a negative stimulus (electric footshock). Because permanent and temporary inactivation of the hippocampus can impair acquisition scores in the T-Maze, this paradigm is considered a test of hippocampal-mediated learning. Testing in the T-maze revealed that cocktail treated mice exhibited a higher mean acquisition score (FIG. 10d) than both the saline and random antisense treated mice ($F_{2,39}$=7.163, p<0.01). This indicates that cocktail treated mice required significantly more trials in the maze before they learned to avoid footshock. To determine if this impairment in learning ability correlated with decreased LRP-1 expression, we conducted Western blots on brain homogenates isolated from the mice tested in the T-maze. FIGS. 11g-h show the results obtained for the small subunit (85 kDa) and the large subunit (515 kDa) of LRP-1. Quantification of the optical density for these bands indicated that, compared to random treated mice, cocktail treated mice showed a significant decrease in the band intensity for the small subunit of LRP-1 (FIG. 11g; p<0.05). Band intensity for the large subunit of LRP-1, however, did not significantly differ between the two treatment groups (FIG. 10h). Quantification of the optical density for actin levels showed that they did not change, indicating that equal amounts of protein were loaded into the wells (data not shown).

Although the T-Maze is designed to assess spatial learning, it relies on the assumption that the treatment groups do not differ in motor ability. Therefore, general locomotor activity was measured in an open-field test. Assessment of activity level in an open field (FIG. 10e), demonstrated that there was no difference between the three treatment groups, indicating that the differences in acquisition scores were not due to altered locomotor ability.

Cocktail and random treated mice (2 wk icv infusion; 100 ng/h) were also assessed for recognition memory in the novel object recognition task (FIG. 11f). After three days of habituation to the testing apparatus (a white opaque box) with no objects present, the mice were then exposed to a series of objects for two days. On day one, mice were allowed to explore two identical objects (A and B) for 5 min. For all mice, total exploration time was similar (data not shown). On day two, object A was replaced with a novel, or new, object (C) and total time spent investigating the new object was recorded. Results showed that mice treated with the random antisense spent a majority of their time investigating the new object (C), indicating memory of the object (B) from the previous day. Cocktail treated mice, however, spent significantly ($p<0.05$) less time investigating the novel object. This indicates that treatment with the cocktail was associated with impairment in recognition memory for the previously explored object (B).

EXAMPLE 3

Modulation of Beta-F1-ATPase Affects Disease and Injury

Example 1 demonstrated that the beta-F1 ATPase was localized in the BBB and that a cocktail of three antisense molecules delivered to the periphery affected the expression of this protein in the BBB. Moreover, this antisense treatment resulted in the specific modulation of efflux of PACAP27 from the brain. As previously mentioned, PACAP is known to have neuroprotective effects in various models of stroke. Therefore, it was of interest to determine the effects of the beta-F1 ATPase modulating antisense cocktail on animal models of stroke. In addition the effect of this cocktail was evaluated in a model of Alzheimer's Disease.

Materials and Methods

Permanent Middle Cerebral Artery Occlusion (pMCAO) Model: PTS-6 antisenses (10:g/mouse of each of the three antisenses) or saline (200:1) were injected via the jugular vein 24 h before pMCAO. Mice were anesthetized with 2.0% sevoflurane in N2O/O2, after which they were subjected to pMCAO by the intraluminal filament technique by use of a monofilament nylon suture as previously described 37. PACAP27 (5 nmol/kg, 200:1) or saline were injected into the jugular vein immediately after pMCAO. Four groups were studied:
  saline-preinjection+saline-postinjection (saline-saline);
  saline-preinjection+PACAP27 postinjection (saline-PACAP27);
  PTS-6 antisenses-preinjection+saline-postinjection (antisensesaline);
  PTS-6 antisenses-preinjection+PACAP27-postinjection (PTS-6 AS-PACAP27).

The neurological score was evaluated at 2 h after pMCAO as followed by the established neurological scoring system 38: (0=normal; 1=consistent forelimb asymmetry but no apparent problem in ambulation; 2=asymmetry in ambulation and reduced resistance to lateral push; 3=circling movement and/or seizures; and 4 morbidly ill and near death.) Twenty-four hours after pMCAO, the brains were removed and were sliced into four 2-mm coronal sections using a mouse brain matrix. Brain slices were then stained with 2% 2,3,5-triphenyltetrazolium chloride (TTC; Wako, Tokyo, Japan) at 37 C for 30 min. The infarct areas were measured using NIH Image software and the infarct volumes were calculated by integration of the infarct areas.

Measurement of Cerebral Blood Flow

Cerebral blood flow (CBF) was measured with a laser Doppler perfusion imager (PeriScan PIM2; PERIMED, Stockholm, Sweden). This noninvasive procedure provides a measurement of blood perfusion in superficial blood vessels of the brain without craniotomy. Mice were anesthetized with sodium pentobarbital sodium (60 mg/kg body wt). Additional doses were given as needed to maintain anesthesia. The skull was exposed by reflecting the scalp and fixing it with cutting tape. The image of 30×30 mm area which covered the skull was obtained. The perfusion index values (a global indicator of blood velocity and perfusion) were expressed in units of volts, and the velocity/perfusion images were set to have a user-defined color scale ranging from 0 (showing black) to 10 (showing red) volts. Short and long term effects of intravenous infusions of PTS-6 antisenses on CBF were determined by measuring CBF before i.v. injection and at 10 minutes and 24 hours after injection. To evaluate CBF during MCAO in PTS-6 antisense and saline treated groups, scans were performed at 24 hours after injection (preMCAO) as baseline. The CBF was measured every 5 min during MCAO up to 30 min. For each evaluation, we generated a mean perfusion index for the elliptic region of interest on both cortex regions over the site supplied by the proximal segment of the MCA. Blood flow values were expressed as a percentage of the CBF baseline values.

Acquisition in the T-maze Foot Shock Avoidance

The effects on acquisition (learning) of iv PACAP27 and PTS-6 antisenses were tested in 12 mo. old SAMP8 mice in the T-maze. The SAMP8 is a spontaneous mutant that develops age-related, amyloid-beta protein-mediated cognitive impairments. The T-maze is a hippocampal dependent learning task in which the animal must integrate multiple cues in a novel environment to learn a new task according to methodology which has been previously described. A start box located at the bottom of the start alley is separated from the alley by a plastic guillotine door, which prevents movement down the alley until training begins. An electrifiable stainless steel rod floor runs throughout the maze to deliver a scrambled foot shock. The guillotine door is raised and a buzzer sounds simultaneously; 5 seconds later foot shock is applied. The goal box that is entered on the first trial is designated "incorrect" and the foot shock continued until the mouse enters the other goal box, which in all subsequent trials is designated as "correct" for that particular mouse. At the end of each trial, the mouse is returned to its home cage until the next trial. The intertribal interval is 30 seconds with a foot shock intensity of 0.35 mA. The buzzer intensity is 55 dB. Mice were trained until they made 1 avoidance. Mice were given the antisenses (10 μg/mouse of each of the three antisenses in 200:1) or saline 48 h before training by tail vein injection. They were then given PACAP27 (0.5 nmol/kg in 200:1/mouse) or saline 24 h before training by tail vein injection.

Results:

To evaluate the effect of the PTS-6 antisenses and PACAP on ischemia in the mouse, the neurological deficit score, the mortality, and the infarct volume after pMCAO were determined. Two-way ANOVA for neurological deficit score (FIG. 11A) with +/−PACAP as one independent variable and +/−antisense as the other showed a significant effect [$F(1,88)=4.87$, $p<0.05$] for the antisense treatment, but no effect of PACAP treatment or interaction. Newman-Keuls found no significant effects. Representative images of the anterior surface of a series of four TTC-stained coronal sections are shown in FIG. 11B. Two-way ANOVA for infarct volume showed a significant effect [$F(1,74)=9.09$, $p<0.005$] for treatment with antisense, but not for PACAP or interaction (FIG. 11C). Newman-Keuls post test showed the saline-saline group to be significantly different from the saline-antisense and the PACAP-antisense treated groups ($p<0.05$). A decrease in mortality from 20% (6 deaths out of 30 mice) for saline-saline treated mice to 10% (2 deaths out of 20 mice) for PACAP-Antisense treated mice 24 hours after ischemia was not significant by Fisher's exact test with 2 sided p value. To rule out the possibility that the PTS-6 antisenses exerted their effects on ischemia by altering cerebral blood perfusion, we performed laser doppler perfusion imaging studies. The CBF mean value for cortex at 10 min and 24 h after i.v. injection of the antisenses were not significantly changed between PTS6 antisenses and the saline injected group (n=6) Moreover, during MCAO up to 30 min, the CBF value on contralateral side or ipsilateral side of cortex were also not different between these groups (n=3-4). The antisense treatment did not alter cerebral blood flow in either the stroked side or the contralateral side.

We also tested the effect of PTS-6 antisenses and PACAP on learning in 12 mo old SAMP8 mice, an animal model of Alzheimer's disease 16. The two-way ANOVA showed a statistical effect for antisense [$F(1,27)=43.4$, $p<<0.01$], but not for PACAP or interaction (FIG. 12D). Newman-Keuls showed that mice given antisense+PACAP learned more quickly than control mice or mice given saline or only PACAP ($p<0.01$).

TABLE 1

Table 1 - Comparison of pharmacokinetics of iv P-Olg for target and non-target tissues in vivo. Percentage of P-19 mer (A, C) and P-23 mer (B, D) taken top by each gram of liver or brain from 0 to 30 min after iv injection. n = number/group.

|  | Brain (n) | Liver (n) |
|---|---|---|
| P-19 mer | | |
| 5 min | 0.042 (2) | 447 (3) |
| 10 min | 0.079 (3) | 5.54 (3) |
| 30 min | 0.116 (3) | 10.43 (3) |
| P23 mer | | |
| 5 min | 0.010 (3) | 2.71 (3) |
| 10 min | 0.044 (3) | 5.33 (3) |
| 30 min | 0.052 (3) | 7.67 (3) |

What is claimed is:

1. A method of inhibiting P-glycoprotein in a patient comprising administering to said patient a phosphorothioate antisense molecule that hybridizes to a P-glycoprotein nucleic acid, wherein said antisense molecule is selected from the group consisting of SEQ ID NOS: 17, 18, 19 20, 21, 35, 36 37, 38, 39 and 40.

2. The method as recited in claim 1, wherein the antisense molecule is administered in conjunction with a drug.

3. The method as recited in claim 2, wherein said antisense molecule is administered systemically, orally, nasally, intravenously, subcutaneously, intramuscularly, or by continuous infusion.

* * * * *

UNITED STATES PATENT AND TRADEMARK OFFICE
CERTIFICATE OF CORRECTION

PATENT NO.         : 8,466,118 B2
APPLICATION NO.    : 12/597458
DATED              : June 18, 2013
INVENTOR(S)        : William A. Banks et al.

It is certified that error appears in the above-identified patent and that said Letters Patent is hereby corrected as shown below:

In the Specification

Column 1, line 12, delete "International" and insert --National-- therefor.

Column 1, line 14, delete "Instutute" and insert --Institute-- therefor.

Column 1, line 15, delete "right" and insert --rights-- therefor.

In the Claims

Claim 1, column 71, line 35, delete "19 20" and insert --19, 20-- therefor.

Claim 1, column 71, line 35, delete "36 37" and insert --36, 37-- therefor.

Signed and Sealed this
Twenty-sixth Day of November, 2013

Margaret A. Focarino
*Commissioner for Patents of the United States Patent and Trademark Office*

UNITED STATES PATENT AND TRADEMARK OFFICE
CERTIFICATE OF CORRECTION

| | | |
|---|---|---|
| PATENT NO. | : 8,466,118 B2 | Page 1 of 1 |
| APPLICATION NO. | : 12/597458 | |
| DATED | : June 18, 2013 | |
| INVENTOR(S) | : Banks et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 416 days.

Signed and Sealed this
Eighteenth Day of November, 2014

Michelle K. Lee
*Deputy Director of the United States Patent and Trademark Office*